US012569360B2

(12) United States Patent
Mayberry et al.

(10) Patent No.: US 12,569,360 B2
(45) Date of Patent: Mar. 10, 2026

(54) APPARATUS AND METHOD OF PLACEMENT OF A GRAFT OR GRAFT SYSTEM

(71) Applicant: Endologix LLC, Irvine, CA (US)

(72) Inventors: Kevin Mayberry, Mission Viejo, CA (US); Craig Welk, Laguna Niguel, CA (US); Richard Monetti, San Clemente, CA (US)

(73) Assignee: Endologix LLC, Irvine, CA (US)

( * ) Notice: Subject to any disclaimer, the term of this patent is extended or adjusted under 35 U.S.C. 154(b) by 0 days.

(21) Appl. No.: 18/430,373

(22) Filed: Feb. 1, 2024

(65) Prior Publication Data

US 2024/0164924 A1     May 23, 2024

Related U.S. Application Data

(60) Continuation of application No. 17/882,378, filed on Aug. 5, 2022, now abandoned, which is a
(Continued)

(51) Int. Cl.
*A61F 2/954* (2013.01)
*A61F 2/07* (2013.01)
(Continued)

(52) U.S. Cl.
CPC ............... *A61F 2/954* (2013.01); *A61F 2/07* (2013.01); *A61F 2/97* (2013.01);
(Continued)

(58) Field of Classification Search
CPC .... A61F 2/954; A61F 2/07; A61F 2/97; A61F 2/89; A61F 2002/061; A61F 2002/065;
(Continued)

(56) References Cited

U.S. PATENT DOCUMENTS

| | | | |
|---|---|---|---|
| 2,127,903 | A | 8/1938 | Bowen |
| 2,437,542 | A | 3/1948 | Krippendorf |

(Continued)

FOREIGN PATENT DOCUMENTS

| | | |
|---|---|---|
| CA | 2220141 | 11/1996 |
| CA | 2133630 | 1/1999 |

(Continued)

OTHER PUBLICATIONS

US 6,413,270 B1, 07/2002, Thornton et al. (withdrawn)
(Continued)

*Primary Examiner* — Jing Rui Ou
(74) *Attorney, Agent, or Firm* — Foley & Lardner LLP

(57) ABSTRACT

A fenestrated graft deployment system, with a delivery catheter having a catheter body. An endoluminal prosthesis having a main graft body, the main graft body having a lumen therethrough and a first opening laterally through a wall of the main graft body. A first guidewire prepositioned within the delivery catheter extending through at least a portion of the catheter body into a main lumen of the endoluminal prosthesis and through the first opening in the wall of the prosthesis when the delivery catheter is in a predeployed configuration. A first fenestration alignment device is configured to extend through at least a portion of the delivery catheter and is configured to be axially moveable relative to the first guidewire. The first fenestration alignment device has an end portion having an outside perimeter configured such that when an end portion of the fenestration alignment device moves toward the first opening of said main graft body the outside perimeter of the first opening is smaller than the outside perimeter of the first fenestration alignment device and prevents it from passing through the first opening and causes the main graft body adjacent to the first opening to move with the end of the first
(Continued)

fenestration alignment device to act as alignment tool to allow an operator to align the first opening in the side of the endoluminal prosthesis with an ostium of a target branch vessel into which said first opening is to extend and act as a guide and seal for a subsequently delivered branch graft endoluminal prosthesis.

13 Claims, 30 Drawing Sheets

Related U.S. Application Data continuation of application No. 15/414,499, filed on Jan. 24, 2017, now Pat. No. 11,406,518, which is a division of application No. 13/287,907, filed on Nov. 2, 2011, now abandoned.

(60) Provisional application No. 61/409,504, filed on Nov. 2, 2010.

(51) Int. Cl.
| | | |
|---|---|---|
| *A61F 2/97* | (2013.01) |
| *A61F 2/06* | (2013.01) |
| *A61F 2/82* | (2013.01) |
| *A61F 2/89* | (2013.01) |

(52) U.S. Cl.
CPC ... *A61F 2002/061* (2013.01); *A61F 2002/065* (2013.01); *A61F 2002/075* (2013.01); *A61F 2002/821* (2013.01); *A61F 2/89* (2013.01); *A61F 2220/0075* (2013.01); *A61F 2250/0008* (2013.01)

(58) Field of Classification Search
CPC .......... A61F 2002/075; A61F 2002/821; A61F 2220/0075; A61F 2250/0008
See application file for complete search history.

(56) References Cited

U.S. PATENT DOCUMENTS

| | | | |
|---|---|---|---|
| 2,845,959 | A | 8/1958 | Sidebotham |
| 2,990,605 | A | 7/1961 | Demsyk |
| 3,029,819 | A | 4/1962 | Starks |
| 3,096,560 | A | 7/1963 | Liebig |
| 3,805,301 | A | 4/1974 | Liebig |
| 3,994,149 | A | 11/1976 | Dahlman |
| 4,362,156 | A | 12/1982 | Feller, Jr. et al. |
| 4,473,087 | A | 9/1984 | Schiff |
| 4,497,074 | A | 2/1985 | Ray et al. |
| 4,501,263 | A | 2/1985 | Harbuck |
| 4,503,568 | A | 3/1985 | Madras |
| 4,512,338 | A | 4/1985 | Balko et al. |
| 4,525,157 | A | 6/1985 | Vaillancourt |
| 4,562,596 | A | 1/1986 | Kornberg |
| 4,580,568 | A | 4/1986 | Gianturco |
| 4,592,754 | A | 6/1986 | Gupte et al. |
| 4,617,932 | A | 10/1986 | Kornberg |
| 4,756,307 | A | 7/1988 | Crownshield |
| 4,795,465 | A | 1/1989 | Marten |
| 4,800,882 | A | 1/1989 | Gianturco |
| 4,816,028 | A | 3/1989 | Kapadia et al. |
| 4,840,940 | A | 6/1989 | Sottiural |
| 4,856,516 | A | 8/1989 | Hillstead |
| 4,878,906 | A | 11/1989 | Lindemann et al. |
| 4,907,338 | A | 3/1990 | Gianturco |
| 4,922,905 | A | 5/1990 | Strecker |
| 4,981,478 | A | 1/1991 | Evard et al. |
| 4,981,947 | A | 1/1991 | Tomagou et al. |
| 4,994,071 | A | 2/1991 | MacGregor |
| 4,994,089 | A | 2/1991 | Ritchrt et al. |
| 5,019,090 | A | 5/1991 | Pinchuk |
| 5,035,706 | A | 7/1991 | Giantureo et al. |
| 5,064,435 | A | 11/1991 | Porter |
| 5,071,425 | A | 12/1991 | Gifford et al. |
| 5,078,726 | A | 1/1992 | Kreamer |
| 5,100,424 | A | 3/1992 | Jang et al. |
| 5,104,399 | A | 4/1992 | Lazarus |
| 5,108,424 | A | 4/1992 | Hoffman, Jr. et al. |
| 5,116,349 | A | 5/1992 | Aranyi |
| 5,123,917 | A | 6/1992 | Lee |
| 5,133,732 | A | 7/1992 | Wiktor |
| 5,135,535 | A | 8/1992 | Kramer |
| 5,135,536 | A | 8/1992 | Hillstead |
| 5,151,105 | A | 9/1992 | Kwan-Gett |
| 5,156,619 | A | 10/1992 | Ehrenfeld |
| 5,158,545 | A | 10/1992 | Trudell et al. |
| 5,178,634 | A | 1/1993 | Martinez |
| 5,197,976 | A | 3/1993 | Herweck et al. |
| 5,201,757 | A | 4/1993 | Heyn et al. |
| 5,211,658 | A | 5/1993 | Clouse |
| 5,246,452 | A | 9/1993 | Sinnott |
| 5,256,141 | A | 10/1993 | Gancheff et al. |
| 5,275,622 | A | 1/1994 | Lazarus et al. |
| 5,282,478 | A | 2/1994 | Fleischhaker et al. |
| 5,282,824 | A | 2/1994 | Gianturco |
| 5,282,860 | A | 2/1994 | Matsuno et al. |
| 5,304,200 | A | 4/1994 | Spaulding |
| 5,314,444 | A | 5/1994 | Gianturco |
| 5,314,472 | A | 5/1994 | Fontaine |
| 5,316,023 | A | 5/1994 | Palmaz et al. |
| 5,320,602 | A | 6/1994 | Karpell |
| 5,330,500 | A | 7/1994 | Song |
| 5,342,387 | A | 8/1994 | Summers |
| 5,354,308 | A | 10/1994 | Simon et al. |
| 5,360,443 | A | 11/1994 | Barone et al. |
| 5,366,504 | A | 11/1994 | Andersen et al. |
| 5,370,683 | A | 12/1994 | Fontaine |
| 5,387,235 | A | 2/1995 | Chuter |
| 5,397,355 | A | 3/1995 | Marin et al. |
| 5,403,341 | A | 4/1995 | Solar |
| 5,405,377 | A | 4/1995 | Cragg |
| 5,405,378 | A | 4/1995 | Strecker |
| 5,414,664 | A | 5/1995 | Lin et al. |
| 5,415,178 | A | 5/1995 | Hsi et al. |
| 5,415,664 | A | 5/1995 | Pinchuk |
| 5,423,886 | A | 6/1995 | Arru et al. |
| 5,425,765 | A | 6/1995 | Tiefenbrun et al. |
| 5,443,477 | A | 8/1995 | Marin et al. |
| 5,443,498 | A | 8/1995 | Fontaine |
| 5,443,500 | A | 8/1995 | Sigwart |
| 5,453,090 | A | 9/1995 | Martinez et al. |
| 5,458,615 | A | 10/1995 | Klemm et al. |
| 5,462,530 | A | 10/1995 | Jang |
| 5,464,449 | A | 11/1995 | Ryan et al. |
| 5,464,450 | A | 11/1995 | Buscemi et al. |
| 5,484,444 | A | 1/1996 | Braunschweiler et al. |
| 5,489,295 | A | 2/1996 | Piplani et al. |
| 5,496,385 | A | 3/1996 | Sgro |
| 5,507,768 | A | 4/1996 | Lau et al. |
| 5,507,769 | A | 4/1996 | Marin et al. |
| 5,507,771 | A | 4/1996 | Gianturco |
| 5,507,787 | A | 4/1996 | Maeda et al. |
| 5,522,880 | A | 6/1996 | Barone et al. |
| 5,522,881 | A | 6/1996 | Lentz |
| 5,522,883 | A | 6/1996 | Slater et al. |
| 5,523,092 | A | 6/1996 | Slater et al. |
| 5,545,118 | A | 8/1996 | Romanauskas |
| 5,545,211 | A | 8/1996 | An et al. |
| 5,549,635 | A | 8/1996 | Solar |
| 5,554,181 | A | 9/1996 | Das |
| 5,562,697 | A | 10/1996 | Christiansen |
| 5,562,724 | A | 10/1996 | Vorwerk et al. |
| 5,562,726 | A | 10/1996 | Chuter |
| 5,562,728 | A | 10/1996 | Lazarus et al. |
| 5,571,169 | A | 11/1996 | Plaia et al. |
| 5,571,172 | A | 11/1996 | Chin |
| 5,571,173 | A | 11/1996 | Parodi |
| 5,575,816 | A | 11/1996 | Rudnick et al. |
| 5,575,818 | A | 11/1996 | Pinchuk |
| 5,578,071 | A | 11/1996 | Parodi |

(56) References Cited

U.S. PATENT DOCUMENTS

| | | | |
|---|---|---|---|
| 5,578,072 A | 11/1996 | Barone et al. |
| 5,591,195 A | 1/1997 | Taheri et al. |
| 5,591,197 A | 1/1997 | Orth et al. |
| 5,591,198 A | 1/1997 | Boyle et al. |
| 5,591,226 A | 1/1997 | Trerotola et al. |
| 5,591,229 A | 1/1997 | Parodi |
| 5,591,230 A | 1/1997 | Horn et al. |
| 5,593,417 A | 1/1997 | Rhodes |
| 5,604,435 A | 2/1997 | Foo et al. |
| 5,607,445 A | 3/1997 | Summers |
| 5,609,625 A | 3/1997 | Piplani et al. |
| 5,609,627 A | 3/1997 | Goicoechea et al. |
| 5,609,628 A | 3/1997 | Keranen |
| 5,628,783 A | 5/1997 | Quiachon et al. |
| 5,628,786 A | 5/1997 | Banas et al. |
| 5,628,788 A | 5/1997 | Pinchuk |
| 5,630,829 A | 5/1997 | Lauterjung |
| 5,630,830 A | 5/1997 | Verbeek |
| 5,632,763 A | 5/1997 | Glastra |
| 5,632,772 A | 5/1997 | Alcime et al. |
| 5,639,278 A | 6/1997 | Dereume et al. |
| 5,641,373 A | 6/1997 | Shannon et al. |
| 5,643,171 A | 7/1997 | Bradshaw et al. |
| 5,643,278 A | 7/1997 | Wijay |
| 5,643,339 A | 7/1997 | Kavteladze et al. |
| 5,647,857 A | 7/1997 | Anderson et al. |
| 5,649,952 A | 7/1997 | Lam |
| 5,651,174 A | 7/1997 | Schwartz et al. |
| 5,653,727 A | 8/1997 | Wiktor |
| 5,653,743 A | 8/1997 | Martin |
| 5,653,746 A | 8/1997 | Schmitt |
| 5,653,747 A | 8/1997 | Dereume |
| 5,662,580 A | 9/1997 | Bradshaw et al. |
| 5,662,614 A | 9/1997 | Edoga |
| 5,662,675 A | 9/1997 | Polanskyj Stockert et al. |
| 5,662,700 A | 9/1997 | Lazarus |
| 5,662,701 A | 9/1997 | Plala et al. |
| 5,662,702 A | 9/1997 | Keranen |
| 5,662,703 A | 9/1997 | Yurek et al. |
| 5,665,115 A | 9/1997 | Cragg |
| 5,665,117 A | 9/1997 | Rhodes |
| 5,666,968 A | 9/1997 | Imran et al. |
| 5,669,880 A | 9/1997 | Solar |
| 5,669,924 A | 9/1997 | Shaknovich |
| 5,669,934 A | 9/1997 | Sawyer |
| 5,674,241 A | 10/1997 | Bley et al. |
| 5,674,276 A | 10/1997 | Andersen et al. |
| 5,676,685 A | 10/1997 | Razaivi |
| 5,676,696 A | 10/1997 | Marcade |
| 5,676,697 A | 10/1997 | McDonald |
| 5,679,400 A | 10/1997 | Tuch |
| 5,681,345 A | 10/1997 | Tuteneuer |
| 5,681,348 A | 10/1997 | Orth et al. |
| 5,683,448 A | 11/1997 | Cragg |
| 5,683,449 A | 11/1997 | Marcade |
| 5,683,450 A | 11/1997 | Goicoechea et al. |
| 5,683,451 A | 11/1997 | Lenker et al. |
| 5,683,453 A | 11/1997 | Paimaz |
| 5,683,462 A | 11/1997 | Barone et al. |
| 5,690,642 A | 11/1997 | Osborne et al. |
| 5,690,643 A | 11/1997 | Wijay |
| 5,690,644 A | 11/1997 | Yurek et al. |
| 5,690,671 A | 11/1997 | McGurk et al. |
| 5,693,066 A | 12/1997 | Rupp et al. |
| 5,693,084 A | 12/1997 | Chuter |
| 5,693,087 A | 12/1997 | Parodi |
| 5,693,088 A | 12/1997 | Goicoechea et al. |
| 5,695,516 A | 12/1997 | Fischell et al. |
| 5,695,517 A | 12/1997 | Marin et al. |
| 5,697,948 A | 12/1997 | Marin et al. |
| 5,697,971 A | 12/1997 | Fischell et al. |
| 5,709,703 A | 1/1998 | Lukic et al. |
| 5,713,917 A | 2/1998 | Leonhardt |
| 5,716,365 A | 2/1998 | Goicoechea et al. |
| 5,716,393 A | 2/1998 | Lindenberg et al. |
| 5,718,724 A | 2/1998 | Goicoechea et al. |
| 5,718,973 A | 2/1998 | Lewis et al. |
| 5,720,735 A | 2/1998 | Dorros |
| 5,720,776 A | 2/1998 | Chuter et al. |
| 5,723,004 A | 3/1998 | Dereume et al. |
| 5,733,325 A | 3/1998 | Robinson et al. |
| 5,746,778 A | 5/1998 | Smith et al. |
| 5,749,880 A | 5/1998 | Banas et al. |
| 5,755,735 A | 5/1998 | Richter et al. |
| 5,755,770 A | 5/1998 | Ravenscroft |
| 5,755,771 A | 5/1998 | Penn et al. |
| 5,755,777 A | 5/1998 | Chuter |
| 5,765,682 A | 6/1998 | Bley et al. |
| 5,766,203 A | 6/1998 | Imran et al. |
| 5,769,885 A | 6/1998 | Quiachon et al. |
| 5,769,887 A | 6/1998 | Brown et al. |
| 5,782,855 A | 7/1998 | Lau et al. |
| 5,782,909 A | 7/1998 | Quiachon et al. |
| 5,800,456 A | 9/1998 | Maeda et al. |
| 5,800,508 A | 9/1998 | Goicoechea et al. |
| 5,800,526 A | 9/1998 | Anderson et al. |
| 5,810,836 A | 9/1998 | Hussein et al. |
| 5,817,100 A | 10/1998 | Igaki |
| 5,823,198 A | 10/1998 | Jones et al. |
| 5,824,037 A | 10/1998 | Fogarty et al. |
| 5,824,039 A | 10/1998 | Piplani et al. |
| 5,824,040 A | 10/1998 | Cox et al. |
| 5,824,053 A | 10/1998 | Khosravi et al. |
| 5,843,160 A | 12/1998 | Rhodes |
| 5,843,162 A | 12/1998 | Inoue |
| 5,843,164 A | 12/1998 | Frantzen et al. |
| 5,843,167 A | 12/1998 | Dwyer et al. |
| 5,851,228 A | 12/1998 | Pinheiro |
| 5,855,599 A | 1/1999 | Wan |
| 5,855,600 A | 1/1999 | Alt |
| 5,860,998 A | 1/1999 | Robinson et al. |
| 5,867,432 A | 2/1999 | Toda |
| 5,868,783 A | 2/1999 | Tower |
| 5,871,536 A | 2/1999 | Lazarus |
| 5,873,906 A | 2/1999 | Lau et al. |
| 5,879,321 A | 3/1999 | Hill |
| 5,879,366 A | 3/1999 | Shaw et al. |
| 5,891,193 A | 4/1999 | Robinson et al. |
| 5,893,887 A | 4/1999 | Jayaraman |
| 5,893,888 A | 4/1999 | Hanson et al. |
| 5,902,334 A | 5/1999 | Dwyer et al. |
| 5,906,640 A | 5/1999 | Penn et al. |
| 5,906,641 A | 5/1999 | Thompson et al. |
| 5,916,263 A | 6/1999 | Goicoceha et al. |
| 5,919,225 A | 7/1999 | Lau et al. |
| 5,925,075 A | 7/1999 | Myers et al. |
| 5,928,248 A | 7/1999 | Acker |
| 5,935,161 A | 8/1999 | Robinson et al. |
| 5,938,696 A | 8/1999 | Goicoechea et al. |
| 5,948,017 A | 9/1999 | Taheri |
| 5,948,018 A | 9/1999 | Dereume et al. |
| 5,957,929 A | 9/1999 | Brenneman |
| 5,957,973 A | 9/1999 | Quiachon et al. |
| 5,961,546 A | 10/1999 | Robinson et al. |
| 5,961,548 A | 10/1999 | Shmulewitz |
| 5,980,514 A | 11/1999 | Kupiecki et al. |
| 5,984,929 A | 11/1999 | Bashiri et al. |
| 5,984,955 A | 11/1999 | Wisselink |
| 5,989,242 A | 11/1999 | Saadat et al. |
| 5,993,489 A | 11/1999 | Lewis et al. |
| 6,001,125 A | 12/1999 | Golds et al. |
| 6,004,347 A | 12/1999 | McNamara |
| 6,004,348 A | 12/1999 | Banas et al. |
| 6,017,363 A | 1/2000 | Hojeibane |
| 6,027,508 A | 2/2000 | Ren et al. |
| 6,027,520 A | 2/2000 | Tsugita et al. |
| 6,027,779 A | 2/2000 | Campbell et al. |
| 6,027,811 A | 2/2000 | Campbell et al. |
| 6,030,415 A | 2/2000 | Chuter |
| 6,033,434 A | 3/2000 | Borghi |
| 6,039,749 A | 3/2000 | Marin et al. |
| 6,039,755 A | 3/2000 | Edwin et al. |
| 6,039,758 A | 3/2000 | Quiachon et al. |
| 6,045,557 A | 4/2000 | White et al. |

(56) References Cited

U.S. PATENT DOCUMENTS

| | | |
|---|---|---|
| 6,051,020 A | 4/2000 | Goicoechea et al. |
| 6,053,940 A | 4/2000 | Wijay |
| 6,056,722 A | 5/2000 | Jayaraman |
| 6,059,813 A | 5/2000 | Vrba et al. |
| 6,059,824 A | 5/2000 | Taheri |
| 6,063,092 A | 5/2000 | Shin |
| 6,063,113 A | 5/2000 | Kavteladze et al. |
| 6,068,654 A | 5/2000 | Berg et al. |
| 6,070,589 A | 6/2000 | Keith et al. |
| 6,074,398 A | 6/2000 | Leschinsky |
| 6,077,296 A | 6/2000 | Shokoohi et al. |
| 6,077,297 A | 6/2000 | Robinson et al. |
| 6,086,611 A | 7/2000 | Duffy et al. |
| 6,090,128 A | 7/2000 | Douglas |
| 6,090,135 A | 7/2000 | Plaia et al. |
| 6,093,194 A | 7/2000 | Mikus et al. |
| 6,093,203 A | 7/2000 | Uflacker |
| 6,096,027 A | 8/2000 | Layne |
| 6,106,548 A | 8/2000 | Reubin et al. |
| 6,117,167 A | 9/2000 | Goicoechea et al. |
| 6,123,722 A | 9/2000 | Fogarty et al. |
| 6,123,723 A | 9/2000 | Konya et al. |
| 6,126,685 A | 10/2000 | Lenker et al. |
| 6,129,756 A | 10/2000 | Kugler et al. |
| 6,136,008 A | 10/2000 | Johnson et al. |
| 6,143,002 A | 11/2000 | Vietmeier |
| 6,143,016 A | 11/2000 | Bleam et al. |
| 6,146,389 A | 11/2000 | Geitz |
| 6,146,415 A | 11/2000 | Fitz |
| 6,149,681 A | 11/2000 | Houser et al. |
| 6,152,944 A | 11/2000 | Holman et al. |
| 6,156,063 A | 12/2000 | Douglas |
| 6,162,237 A | 12/2000 | Chan |
| 6,165,195 A | 12/2000 | Wilson et al. |
| 6,165,214 A | 12/2000 | Lazarus |
| 6,168,610 B1 | 1/2001 | Marin et al. |
| 6,171,281 B1 | 1/2001 | Zhang |
| 6,183,481 B1 | 2/2001 | Lee et al. |
| 6,183,509 B1 | 2/2001 | Dibie |
| 6,187,015 B1 | 2/2001 | Brenneman |
| 6,187,033 B1 | 2/2001 | Schmitt et al. |
| 6,187,036 B1 | 2/2001 | Shaolian et al. |
| 6,192,944 B1 | 2/2001 | Greenhalgh |
| 6,193,726 B1 | 2/2001 | Vanney |
| 6,193,745 B1 | 2/2001 | Fogarty et al. |
| 6,197,049 B1 | 3/2001 | Shaolian et al. |
| 6,203,785 B1 | 3/2001 | Edwin et al. |
| 6,210,429 B1 | 4/2001 | Vardi et al. |
| 6,221,090 B1 | 4/2001 | Wilson |
| 6,221,098 B1 | 4/2001 | Wilson |
| 6,221,102 B1 | 4/2001 | Baker et al. |
| 6,224,609 B1 | 5/2001 | Ressemann et al. |
| 6,224,627 B1 | 5/2001 | Armstrong et al. |
| 6,231,563 B1 | 5/2001 | White et al. |
| 6,235,051 B1 | 5/2001 | Murphy |
| 6,254,609 B1 | 7/2001 | Vrba et al. |
| 6,254,628 B1 | 7/2001 | Wallace et al. |
| 6,261,316 B1 | 7/2001 | Shaolian et al. |
| 6,264,682 B1 | 7/2001 | Wilson et al. |
| 6,273,909 B1 | 8/2001 | Kugler et al. |
| 6,280,465 B1 | 8/2001 | Cryer |
| 6,280,467 B1 | 8/2001 | Leonhardt |
| 6,280,486 B1 | 8/2001 | Kugler et al. |
| 6,283,991 B1 | 9/2001 | Cox et al. |
| 6,287,329 B1 | 9/2001 | Duering et al. |
| 6,296,622 B1 | 10/2001 | Kurz et al. |
| 6,312,406 B1 | 11/2001 | Jayaraman |
| 6,325,826 B1 | 12/2001 | Vardi et al. |
| 6,331,184 B1 | 12/2001 | Abrams |
| 6,331,190 B1 | 12/2001 | Shokoohi et al. |
| 6,334,867 B1 | 1/2002 | Anson |
| 6,344,056 B1 | 2/2002 | Dendashtian |
| 6,346,118 B1 | 2/2002 | Baker et al. |
| 6,348,066 B1 | 2/2002 | Pinchuk et al. |
| 6,350,278 B1 | 2/2002 | Lenker et al. |
| 6,352,553 B1 | 3/2002 | Van der Burg et al. |
| 6,352,554 B2 | 3/2002 | De Paulis |
| 6,352,561 B1 | 3/2002 | Leopold et al. |
| 6,355,060 B1 | 3/2002 | Lenker et al. |
| 6,361,544 B1 | 3/2002 | Wilson et al. |
| 6,361,555 B1 | 3/2002 | Wilson |
| 6,361,557 B1 | 3/2002 | Gittings et al. |
| 6,361,559 B1 | 3/2002 | Houser et al. |
| 6,361,637 B2 | 3/2002 | Martin et al. |
| 6,383,213 B2 | 5/2002 | Wilson et al. |
| 6,387,120 B2 | 5/2002 | Wilson et al. |
| 6,395,017 B1 | 5/2002 | Dwyer et al. |
| 6,395,018 B1 | 5/2002 | Castaneda |
| 6,395,019 B2 | 5/2002 | Chobotov |
| 6,398,807 B1 | 6/2002 | Chouinard et al. |
| 6,409,750 B1 | 6/2002 | Hyodoh et al. |
| 6,409,757 B1 | 6/2002 | Trout, III et al. |
| 6,416,474 B1 | 7/2002 | Penner et al. |
| 6,416,542 B1 | 7/2002 | Marcade et al. |
| 6,425,765 B1 | 7/2002 | Irwin, III |
| 6,428,565 B1 | 8/2002 | Wisselink |
| 6,428,567 B2 | 8/2002 | Wilson et al. |
| 6,432,130 B1 | 8/2002 | Hanson |
| 6,432,131 B1 | 8/2002 | Ravenscroft |
| 6,432,134 B1 | 8/2002 | Anson et al. |
| 6,436,135 B1 | 8/2002 | Goldfarb |
| 6,440,161 B1 | 8/2002 | Madrid et al. |
| 6,447,540 B1 | 9/2002 | Fontaine et al. |
| 6,458,152 B1 | 10/2002 | Khosravi et al. |
| 6,464,721 B1 | 10/2002 | Marcade et al. |
| 6,475,166 B1 | 11/2002 | Escano |
| 6,475,170 B1 | 11/2002 | Doron et al. |
| 6,482,211 B1 | 11/2002 | Choi |
| 6,485,513 B1 | 11/2002 | Fan |
| 6,491,719 B1 | 12/2002 | Fogrty et al. |
| 6,500,182 B2 | 12/2002 | Foster |
| 6,500,202 B1 | 12/2002 | Shaolian et al. |
| 6,508,833 B2 | 1/2003 | Pavonick et al. |
| 6,508,835 B1 | 1/2003 | Shaolian et al. |
| 6,508,836 B2 | 1/2003 | Wilson et al. |
| 6,511,325 B1 | 1/2003 | Lalka et al. |
| 6,514,281 B1 | 2/2003 | Blaeser et al. |
| 6,514,282 B1 | 2/2003 | Inoue |
| 6,517,572 B2 | 2/2003 | Kugler et al. |
| 6,517,573 B1 | 2/2003 | Pollock et al. |
| 6,520,988 B1 | 2/2003 | Colombo et al. |
| 6,524,335 B1 | 2/2003 | Hartley et al. |
| 6,524,336 B1 | 2/2003 | Papazolgou et al. |
| 6,533,811 B1 | 3/2003 | Ryan et al. |
| 6,544,278 B1 | 4/2003 | Vrba et al. |
| 6,551,350 B1 | 4/2003 | Thornton et al. |
| 6,558,396 B1 | 5/2003 | Inoue |
| 6,562,063 B1 | 5/2003 | Euteneurer et al. |
| 6,565,596 B1 | 5/2003 | White et al. |
| 6,565,597 B1 | 5/2003 | Fearnot et al. |
| RE38,146 E | 6/2003 | Palmaz et al. |
| 6,572,645 B2 | 6/2003 | Leonhardt |
| 6,576,005 B1 | 6/2003 | Geitz |
| 6,576,009 B2 | 6/2003 | Ryan et al. |
| 6,579,308 B1 | 6/2003 | Jansen et al. |
| 6,579,312 B2 | 6/2003 | Wilson et al. |
| 6,582,394 B1 | 6/2003 | Reiss et al. |
| 6,582,460 B1 | 6/2003 | Cryer |
| 6,585,758 B1 | 7/2003 | Chouinard et al. |
| 6,592,548 B2 | 7/2003 | Jayaraman |
| 6,592,614 B2 | 7/2003 | Lenker et al. |
| 6,592,615 B1 | 7/2003 | Marcade et al. |
| 6,599,315 B2 | 7/2003 | Wilson |
| 6,607,552 B1 | 8/2003 | Hanson |
| 6,613,073 B1 | 9/2003 | White et al. |
| 6,616,675 B1 | 9/2003 | Evard et al. |
| 6,646,242 B1 | 11/2003 | Quinn |
| 6,652,567 B1 | 11/2003 | Deaton |
| 6,652,579 B1 | 11/2003 | Cox et al. |
| 6,656,213 B2 | 12/2003 | Solem |
| 6,660,033 B1 | 12/2003 | Marcade et al. |
| 6,663,665 B2 | 12/2003 | Shaolian et al. |
| 6,669,718 B2 | 12/2003 | Besselink |
| 6,692,483 B2 | 2/2004 | Vardi et al. |

(56) References Cited

U.S. PATENT DOCUMENTS

| | | | |
|---|---|---|---|
| 6,695,875 | B2 | 2/2004 | Stelter et al. |
| 6,702,843 | B1 | 3/2004 | Brown et al. |
| 6,706,062 | B2 | 3/2004 | Vardi et al. |
| 6,723,116 | B2 | 4/2004 | Taheri |
| 6,733,523 | B2 | 5/2004 | Shaolian et al. |
| 6,740,101 | B2 | 5/2004 | Houser et al. |
| 6,761,733 | B2 | 7/2004 | Chobotov et al. |
| 6,767,359 | B2 | 7/2004 | Weadock |
| 6,773,457 | B2 | 8/2004 | Ivancev et al. |
| 6,790,224 | B2 | 9/2004 | Gerberding |
| 6,793,671 | B2 | 9/2004 | Wall |
| 6,800,085 | B2 | 10/2004 | Duane et al. |
| 6,802,859 | B1 | 10/2004 | Pazienza et al. |
| 6,811,566 | B1 | 11/2004 | Penn et al. |
| 6,814,752 | B1 | 11/2004 | Chuter |
| 6,818,014 | B2 | 11/2004 | Brown et al. |
| 6,821,292 | B2 | 11/2004 | Pazienza et al. |
| 6,827,706 | B2 | 12/2004 | Parodi |
| 6,827,726 | B2 | 12/2004 | Parodi |
| 6,833,003 | B2 | 12/2004 | Jones et al. |
| 6,835,203 | B1 | 12/2004 | Vardi et al. |
| 6,840,950 | B2 | 1/2005 | Standford et al. |
| 6,858,038 | B2 | 2/2005 | Heuser |
| 6,875,229 | B2 | 4/2005 | Wilson et al. |
| 6,887,249 | B1 | 5/2005 | Houser et al. |
| 6,887,251 | B1 | 5/2005 | Suval |
| 6,889,026 | B2 | 5/2005 | Schlageter et al. |
| 6,896,699 | B2 | 5/2005 | Wilson et al. |
| 6,899,727 | B2 | 5/2005 | Armstrong et al. |
| 6,899,728 | B1 | 5/2005 | Phillips et al. |
| 6,905,505 | B2 | 6/2005 | Nash et al. |
| 6,908,477 | B2 | 6/2005 | McGuckin |
| 6,918,925 | B2 | 7/2005 | Tehrani |
| 6,923,829 | B2 | 8/2005 | Boyle et al. |
| 6,928,279 | B2 | 8/2005 | Seligmann et al. |
| 6,929,661 | B2 | 8/2005 | Bolduc et al. |
| 6,932,837 | B2 | 8/2005 | Amplatz et al. |
| 6,939,368 | B2 | 9/2005 | Simso |
| 6,939,371 | B2 | 9/2005 | Kugler et al. |
| 6,939,377 | B2 | 9/2005 | Jayaraman et al. |
| 6,942,691 | B1 | 9/2005 | Chuter |
| 6,942,692 | B2 | 9/2005 | Landau et al. |
| 6,942,693 | B2 | 9/2005 | Chouinard et al. |
| 6,948,017 | B2 | 9/2005 | Carpenter et al. |
| 6,953,475 | B2 | 10/2005 | Shaolian et al. |
| 6,955,679 | B1 | 10/2005 | Hendricksen et al. |
| 6,955,688 | B2 | 10/2005 | Wilson et al. |
| 6,960,217 | B2 | 11/2005 | Bolduc |
| 6,962,602 | B2 | 11/2005 | Vardi |
| 6,974,471 | B2 | 12/2005 | Van Schie et al. |
| 6,981,982 | B2 | 1/2006 | Armstrong et al. |
| 6,984,244 | B2 | 1/2006 | Perez et al. |
| 6,989,024 | B2 | 1/2006 | Hebert et al. |
| 6,989,028 | B2 | 1/2006 | Richter et al. |
| 6,994,721 | B2 | 2/2006 | Israel |
| 6,994,722 | B2 | 2/2006 | DiCarlo |
| 7,004,926 | B2 | 2/2006 | Navia et al. |
| 7,004,964 | B2 | 2/2006 | Thompson et al. |
| 7,004,967 | B2 | 2/2006 | Chouinard et al. |
| 7,014,653 | B2 | 3/2006 | Ouriel et al. |
| 7,025,779 | B2 | 4/2006 | Elliott |
| 7,029,494 | B2 | 4/2006 | Soun et al. |
| 7,029,496 | B2 | 4/2006 | Rakos et al. |
| 7,074,235 | B1 | 7/2006 | Roy |
| 7,074,236 | B2 | 7/2006 | Rabkin et al. |
| 7,105,015 | B2 | 9/2006 | Goshgarian |
| 7,105,017 | B2 | 9/2006 | Kerr |
| 7,105,020 | B2 | 9/2006 | Greenberg et al. |
| 7,118,583 | B2 | 10/2006 | Davidson et al. |
| 7,122,051 | B1 | 10/2006 | Dallara et al. |
| 7,122,052 | B2 | 10/2006 | Greenhalgh |
| 7,125,464 | B2 | 10/2006 | Chobotov et al. |
| 7,131,991 | B2 | 11/2006 | Zarins et al. |
| 7,144,422 | B1 | 12/2006 | Rao |
| 7,160,318 | B2 | 1/2007 | Greenberg et al. |
| 7,162,302 | B2 | 1/2007 | Wang et al. |
| 7,163,715 | B1 | 1/2007 | Kramer |
| 7,175,651 | B2 | 2/2007 | Kerr |
| 7,175,657 | B2 | 2/2007 | Khan et al. |
| 7,175,662 | B2 | 2/2007 | Cook et al. |
| 7,189,256 | B2 | 3/2007 | Smith |
| 7,189,257 | B2 | 3/2007 | Schmitt et al. |
| 7,195,648 | B2 | 3/2007 | Jones et al. |
| 7,201,770 | B2 | 4/2007 | Johnson et al. |
| 7,220,274 | B1 | 5/2007 | Quinn |
| 7,220,275 | B2 | 5/2007 | Davidson et al. |
| 7,229,472 | B2 | 6/2007 | DePalma et al. |
| 7,232,449 | B2 | 6/2007 | Sharkawy et al. |
| 7,235,095 | B2 | 6/2007 | Haverkost et al. |
| 7,237,552 | B2 | 7/2007 | Khera et al. |
| 7,241,300 | B2 | 7/2007 | Sharkawy et al. |
| 7,244,444 | B2 | 7/2007 | Bates |
| 7,261,733 | B1 | 8/2007 | Brown et al. |
| 7,264,631 | B2 | 9/2007 | DeCarlo |
| 7,264,632 | B2 | 9/2007 | Wright et al. |
| 7,267,685 | B2 | 9/2007 | Butaric et al. |
| 7,270,675 | B2 | 9/2007 | Chun et al. |
| 7,285,130 | B2 | 10/2007 | Austin |
| 7,294,145 | B2 | 11/2007 | Ward |
| 7,300,460 | B2 | 11/2007 | Levine et al. |
| 7,306,623 | B2 | 12/2007 | Watson |
| 7,309,351 | B2 | 12/2007 | Escamilla et al. |
| 7,314,481 | B2 | 1/2008 | Karpiel |
| 7,314,483 | B2 | 1/2008 | Landau et al. |
| 7,320,703 | B2 | 1/2008 | DiMatteo et al. |
| 7,341,598 | B2 | 3/2008 | Davidson et al. |
| 7,367,985 | B2 | 5/2008 | Mazzocchi et al. |
| 7,367,986 | B2 | 5/2008 | Mazzocchi et al. |
| 7,371,250 | B2 | 5/2008 | Mazzocchi et al. |
| 7,402,168 | B2 | 7/2008 | Acosta et al. |
| 7,402,171 | B2 | 7/2008 | Osborne et al. |
| 7,413,573 | B2 | 8/2008 | Hartley et al. |
| 7,425,219 | B2 | 9/2008 | Quadri et al. |
| 7,435,253 | B1 | 10/2008 | Hartley et al. |
| 7,438,721 | B2 | 10/2008 | Doig et al. |
| 7,491,230 | B2 | 2/2009 | Holman et al. |
| 7,491,232 | B2 | 2/2009 | Bolduc et al. |
| 7,520,890 | B2 | 4/2009 | Phillips |
| 7,520,895 | B2 | 4/2009 | Douglas et al. |
| 7,527,636 | B2 | 5/2009 | Dunfee et al. |
| 7,537,606 | B2 | 5/2009 | Hartley |
| 7,553,324 | B2 | 6/2009 | Andreas et al. |
| 7,572,289 | B2 | 8/2009 | Sisken et al. |
| 7,575,590 | B2 | 8/2009 | Watson |
| 7,578,841 | B2 | 8/2009 | Yadin et al. |
| 7,582,111 | B2 | 9/2009 | Krolik et al. |
| 7,591,832 | B2 | 9/2009 | Eversull et al. |
| 7,591,843 | B1 | 9/2009 | Escano et al. |
| 7,611,529 | B2 | 11/2009 | Greenberg et al. |
| 7,615,072 | B2 | 11/2009 | Rust et al. |
| 7,618,398 | B2 | 11/2009 | Holman et al. |
| 7,632,299 | B2 | 12/2009 | Weber |
| 7,635,383 | B2 | 12/2009 | Gumm |
| 7,637,932 | B2 | 12/2009 | Bolduc et al. |
| 7,641,684 | B2 | 1/2010 | Hilaire et al. |
| 7,645,298 | B2 | 1/2010 | Hartley et al. |
| 7,651,518 | B2 | 1/2010 | Dittman |
| 7,670,369 | B2 | 3/2010 | Shaeffer et al. |
| 7,674,284 | B2 | 3/2010 | Melsheimer |
| 7,678,141 | B2 | 3/2010 | Greenan et al. |
| 7,691,135 | B2 | 4/2010 | Shaolian et al. |
| 7,695,508 | B2 | 4/2010 | Van Der Leest et al. |
| 7,699,885 | B2 | 4/2010 | Leonhardt et al. |
| 7,708,771 | B2 | 5/2010 | Chuter et al. |
| 7,708,773 | B2 | 5/2010 | Pinchuk et al. |
| 7,722,657 | B2 | 5/2010 | Hartley |
| 7,753,951 | B2 | 7/2010 | Shaked et al. |
| 7,758,633 | B2 | 7/2010 | Nazzaro |
| 7,766,961 | B2 | 8/2010 | Patel et al. |
| 7,771,465 | B2 | 8/2010 | Zukowski |
| 7,785,340 | B2 | 8/2010 | Heidner et al. |
| 7,785,361 | B2 | 8/2010 | Nikolchev et al. |
| 7,806,917 | B2 | 10/2010 | Xiao |
| 7,815,601 | B2 | 10/2010 | Jordan et al. |

(56)                    References Cited

U.S. PATENT DOCUMENTS

| | | | |
|---|---|---|---|
| 7,815,661 B2 | 10/2010 | Mirizzi et al. | |
| 7,828,837 B2 | 11/2010 | Khoury | |
| 7,833,259 B2 | 11/2010 | Boatman | |
| 7,867,270 B2 | 1/2011 | Hartley | |
| 7,879,081 B2 | 2/2011 | DeMatteo et al. | |
| 7,892,275 B2 | 2/2011 | Hartley et al. | |
| 7,909,873 B2 | 3/2011 | Tan-Malecki et al. | |
| 7,914,572 B2 | 3/2011 | Hartley et al. | |
| 8,034,100 B2 | 10/2011 | Shaolian et al. | |
| 8,100,960 B2 | 1/2012 | Bruszewski | |
| 8,118,856 B2 | 2/2012 | Schreck et al. | |
| 8,152,830 B2 | 4/2012 | Gumm | |
| 8,206,430 B2 | 6/2012 | Mafi et al. | |
| 8,216,295 B2 | 7/2012 | Bemjamin et al. | |
| 8,221,494 B2 | 7/2012 | Schreck et al. | |
| 8,236,040 B2 | 8/2012 | Mayberry et al. | |
| 8,343,204 B2 | 1/2013 | Osborne | |
| 8,357,192 B2 | 1/2013 | Mayberry et al. | |
| 8,491,646 B2 | 7/2013 | Schreck | |
| 8,523,931 B2 | 9/2013 | Mayberry et al. | |
| 8,672,989 B2 | 3/2014 | Schreck et al. | |
| 8,764,812 B2 | 7/2014 | Mayberry et al. | |
| 8,808,350 B2 | 8/2014 | Schreck et al. | |
| 8,828,074 B2 | 9/2014 | Xiao et al. | |
| 8,846,708 B2 | 9/2014 | Hartley et al. | |
| 8,945,202 B2 | 2/2015 | Mayberry et al. | |
| 9,149,381 B2 | 10/2015 | Schreck et al. | |
| 2001/0003161 A1 | 6/2001 | Vardi et al. | |
| 2001/0014823 A1 | 8/2001 | Ressemann | |
| 2001/0016767 A1 | 8/2001 | Wilson et al. | |
| 2001/0027338 A1 | 10/2001 | Greenberg | |
| 2001/0037142 A1 | 11/2001 | Stelter et al. | |
| 2001/0039445 A1 | 11/2001 | Hall et al. | |
| 2001/0049548 A1* | 12/2001 | Vardi | A61F 2/958 |
| | | | 606/108 |
| 2002/0042650 A1 | 4/2002 | Vardi et al. | |
| 2002/0049412 A1 | 4/2002 | Madrid et al. | |
| 2002/0052648 A1 | 5/2002 | McGuckin et al. | |
| 2002/0116047 A1 | 8/2002 | Vardi et al. | |
| 2002/0123786 A1 | 9/2002 | Gittings et al. | |
| 2002/0138088 A1 | 9/2002 | Nash et al. | |
| 2002/0143383 A1 | 10/2002 | Parodi | |
| 2002/0147491 A1 | 10/2002 | Khan et al. | |
| 2002/0156516 A1 | 10/2002 | Vardi | |
| 2002/0156518 A1 | 10/2002 | Tehrani | |
| 2002/0173835 A1 | 11/2002 | Bourang et al. | |
| 2002/0193872 A1 | 12/2002 | Trout et al. | |
| 2002/0198585 A1 | 12/2002 | Wisselink | |
| 2003/0004560 A1 | 1/2003 | Chobotov et al. | |
| 2003/0028233 A1 | 2/2003 | Vardi et al. | |
| 2003/0083678 A1 | 5/2003 | Herweck et al. | |
| 2003/0097169 A1 | 5/2003 | Brucker et al. | |
| 2003/0135257 A1 | 7/2003 | Taheri | |
| 2003/0167083 A1 | 9/2003 | Lashinski et al. | |
| 2003/0176910 A1 | 9/2003 | Vrba et al. | |
| 2003/0199967 A1 | 10/2003 | Hartley et al. | |
| 2003/0236566 A1 | 12/2003 | Heuser | |
| 2003/0236585 A1 | 12/2003 | DiMatteo et al. | |
| 2004/0015231 A1 | 1/2004 | Suhr | |
| 2004/0049204 A1 | 3/2004 | Harari et al. | |
| 2004/0049257 A1 | 3/2004 | Kaspersen et al. | |
| 2004/0059406 A1 | 3/2004 | Cully et al. | |
| 2004/0073288 A1 | 4/2004 | Kerr | |
| 2004/0093058 A1 | 5/2004 | Cottone et al. | |
| 2004/0098084 A1 | 5/2004 | Hartley et al. | |
| 2004/0098096 A1 | 5/2004 | Eton | |
| 2004/0106972 A1 | 6/2004 | Deaton | |
| 2004/0127975 A1 | 7/2004 | Levine et al. | |
| 2004/0143312 A1 | 7/2004 | Samson et al. | |
| 2004/0176832 A1 | 9/2004 | Hartley et al. | |
| 2004/0193254 A1 | 9/2004 | Greenberg et al. | |
| 2004/0215327 A1 | 10/2004 | Doig et al. | |
| 2004/0230287 A1 | 11/2004 | Hartley et al. | |
| 2004/0236403 A1 | 11/2004 | Leonhardt et al. | |
| 2005/0015135 A1 | 1/2005 | Shanley | |
| 2005/0033403 A1 | 2/2005 | Ward et al. | |
| 2005/0033405 A1 | 2/2005 | Solovay | |
| 2005/0038494 A1 | 2/2005 | Eidenschink | |
| 2005/0049672 A1 | 3/2005 | Murphy | |
| 2005/0058327 A1 | 3/2005 | Pieper | |
| 2005/0059923 A1 | 3/2005 | Gamboa | |
| 2005/0059994 A1 | 3/2005 | Walak et al. | |
| 2005/0060025 A1 | 3/2005 | Mackiewicz et al. | |
| 2005/0060026 A1 | 3/2005 | Gamboa | |
| 2005/0080476 A1 | 4/2005 | Gunderson et al. | |
| 2005/0085845 A1 | 4/2005 | Hilaire et al. | |
| 2005/0085891 A1 | 4/2005 | Goto et al. | |
| 2005/0102018 A1 | 5/2005 | Carpenter et al. | |
| 2005/0113693 A1 | 5/2005 | Smith et al. | |
| 2005/0113853 A1 | 5/2005 | Noriega et al. | |
| 2005/0113905 A1 | 5/2005 | Greenberg et al. | |
| 2005/0119719 A1 | 6/2005 | Wallace et al. | |
| 2005/0119731 A1 | 6/2005 | Brucker et al. | |
| 2005/0121120 A1 | 6/2005 | Van Dijk et al. | |
| 2005/0131517 A1 | 6/2005 | Hartley et al. | |
| 2005/0131518 A1 | 6/2005 | Hartley et al. | |
| 2005/0131519 A1 | 6/2005 | Hartley | |
| 2005/0131526 A1 | 6/2005 | Wong | |
| 2005/0149186 A1 | 7/2005 | Schaeffer et al. | |
| 2005/0154444 A1 | 7/2005 | Quadri | |
| 2005/0159758 A1 | 7/2005 | Laks | |
| 2005/0159803 A1 | 7/2005 | Lad et al. | |
| 2005/0165470 A1 | 7/2005 | Weber | |
| 2005/0165480 A1 | 7/2005 | Jordan et al. | |
| 2005/0171597 A1 | 8/2005 | Boatman et al. | |
| 2005/0171598 A1 | 8/2005 | Schaeffer | |
| 2005/0177221 A1 | 8/2005 | Mustapha | |
| 2005/0215327 A1 | 9/2005 | Weisel et al. | |
| 2005/0216043 A1 | 9/2005 | Blatter et al. | |
| 2005/0222668 A1 | 10/2005 | Schaeffer et al. | |
| 2005/0228480 A1 | 10/2005 | Douglas et al. | |
| 2005/0240153 A1 | 10/2005 | Opie | |
| 2005/0240258 A1 | 10/2005 | Bolduc et al. | |
| 2005/0240260 A1 | 10/2005 | Bolduc | |
| 2005/0273150 A1 | 12/2005 | Howel et al. | |
| 2005/0273162 A1* | 12/2005 | Laguna | A61F 2/07 |
| | | | 623/1.53 |
| 2005/0288772 A1 | 12/2005 | Douglas et al. | |
| 2006/0020320 A1 | 1/2006 | Shaolian et al. | |
| 2006/0036315 A1 | 2/2006 | Yadin et al. | |
| 2006/0058864 A1 | 3/2006 | Schaeffer et al. | |
| 2006/0089704 A1 | 4/2006 | Douglas | |
| 2006/0142704 A1 | 6/2006 | Lentz | |
| 2006/0142838 A1 | 6/2006 | Molaei et al. | |
| 2006/0149350 A1 | 7/2006 | Patel et al. | |
| 2006/0155358 A1 | 7/2006 | LaDuca et al. | |
| 2006/0155363 A1 | 7/2006 | LaDuca et al. | |
| 2006/0155366 A1 | 7/2006 | LaDuca et al. | |
| 2006/0161244 A1 | 7/2006 | Sequin | |
| 2006/0173525 A1 | 8/2006 | Behl et al. | |
| 2006/0178726 A1 | 8/2006 | Myles | |
| 2006/0217794 A1 | 9/2006 | Ruiz et al. | |
| 2006/0224232 A1 | 10/2006 | Chobotov | |
| 2006/0229669 A1 | 10/2006 | Mirizzi et al. | |
| 2006/0229699 A1 | 10/2006 | Tehrani et al. | |
| 2006/0229707 A1 | 10/2006 | Khoury | |
| 2006/0233990 A1 | 10/2006 | Humphrey et al. | |
| 2006/0233991 A1 | 10/2006 | Humphrey et al. | |
| 2006/0247760 A1 | 11/2006 | Ganesan et al. | |
| 2006/0247761 A1 | 11/2006 | Greenberg et al. | |
| 2006/0259063 A1 | 11/2006 | Bates et al. | |
| 2006/0271163 A1 | 11/2006 | Shokoohl | |
| 2006/0271164 A1 | 11/2006 | Shaolian et al. | |
| 2007/0010887 A1 | 1/2007 | Carter et al. | |
| 2007/0016280 A1 | 1/2007 | Yacoby et al. | |
| 2007/0021828 A1 | 1/2007 | Krolik et al. | |
| 2007/0027522 A1 | 2/2007 | Chang et al. | |
| 2007/0027526 A1 | 2/2007 | Demetriades et al. | |
| 2007/0043425 A1 | 2/2007 | Hartley et al. | |
| 2007/0050016 A1 | 3/2007 | Gregorich et al. | |
| 2007/0055350 A1 | 3/2007 | Erickson | |
| 2007/0055360 A1 | 3/2007 | Hanson et al. | |
| 2007/0055362 A1 | 3/2007 | Brown | |
| 2007/0067019 A1 | 3/2007 | Miller et al. | |

(56)                    References Cited

U.S. PATENT DOCUMENTS

| | | |
|---|---|---|
| 2007/0067023 A1 | 3/2007 | Kveen et al. |
| 2007/0073376 A1 | 3/2007 | Krolik et al. |
| 2007/0073388 A1 | 3/2007 | Krolik et al. |
| 2007/0088424 A1 | 4/2007 | Greenberg et al. |
| 2007/0112420 A1 | 5/2007 | LaDuca |
| 2007/0118208 A1 | 5/2007 | Kerr |
| 2007/0123805 A1 | 5/2007 | Shireman et al. |
| 2007/0142896 A1 | 6/2007 | Anderson et al. |
| 2007/0149166 A1 | 6/2007 | Turcotte et al. |
| 2007/0150051 A1 | 6/2007 | Arnault De La Menardiere et al. |
| 2007/0167955 A1 | 7/2007 | Arnault De La Menardiere et al. |
| 2007/0168019 A1 | 7/2007 | Amplatz et al. |
| 2007/0173921 A1 | 7/2007 | Wholey et al. |
| 2007/0179592 A1 | 8/2007 | Schaeffer |
| 2007/0198076 A1 | 8/2007 | Hebert et al. |
| 2007/0203571 A1 | 8/2007 | Kaplan et al. |
| 2007/0213804 A1 | 9/2007 | Schaeffer et al. |
| 2007/0219620 A1 | 9/2007 | Eells et al. |
| 2007/0219621 A1 | 9/2007 | Hartley et al. |
| 2007/0225796 A1 | 9/2007 | Yadin et al. |
| 2007/0225797 A1 | 9/2007 | Krivoruhko |
| 2007/0225798 A1 | 9/2007 | Gregorich |
| 2007/0233220 A1 | 10/2007 | Greenan |
| 2007/0244540 A1 | 10/2007 | Pryor |
| 2007/0244542 A1 | 10/2007 | Greenan et al. |
| 2007/0244547 A1 | 10/2007 | Greenan |
| 2007/0248640 A1 | 10/2007 | Karabey et al. |
| 2007/0250084 A1 | 10/2007 | Sharkway et al. |
| 2007/0260302 A1 | 11/2007 | Igaki |
| 2007/0260304 A1 | 11/2007 | Gregorich et al. |
| 2007/0293940 A1 | 12/2007 | Schaeffer et al. |
| 2007/0299494 A1 | 12/2007 | Zukowski |
| 2007/0299495 A1 | 12/2007 | Zukowski et al. |
| 2007/0299497 A1 | 12/2007 | Shaolian et al. |
| 2007/0299499 A1 | 12/2007 | Hartley |
| 2007/0299501 A1 | 12/2007 | Hebert et al. |
| 2008/0009932 A1 | 1/2008 | Ta et al. |
| 2008/0009933 A1 | 1/2008 | Ta et al. |
| 2008/0009937 A1 | 1/2008 | Kipperman |
| 2008/0015681 A1 | 1/2008 | Wilson |
| 2008/0033525 A1 | 2/2008 | Shaked et al. |
| 2008/0046066 A1 | 2/2008 | Jenson et al. |
| 2008/0058918 A1 | 3/2008 | Watson |
| 2008/0065197 A1 | 3/2008 | Meyer et al. |
| 2008/0071343 A1 | 3/2008 | Mayberry et al. |
| 2008/0086191 A1 | 4/2008 | Valencia |
| 2008/0108065 A1 | 5/2008 | Bowe |
| 2008/0109056 A1 | 5/2008 | Chalekian |
| 2008/0114444 A1 | 5/2008 | Yu |
| 2008/0114446 A1 | 5/2008 | Hartley |
| 2008/0133000 A1 | 6/2008 | Molony |
| 2008/0167704 A1 | 7/2008 | Wright et al. |
| 2008/0172119 A1 | 7/2008 | Yamasaki et al. |
| 2008/0172122 A1 | 7/2008 | Mayberry et al. |
| 2008/0188921 A1 | 8/2008 | Yamasaki et al. |
| 2008/0208307 A1* | 8/2008 | Ben-Muvhar .......... A61F 2/958 604/103.05 |
| 2008/0208310 A1 | 8/2008 | McDermott et al. |
| 2008/0208319 A1 | 8/2008 | Rabkin et al. |
| 2008/0256652 A1 | 10/2008 | Thomas et al. |
| 2008/0262595 A1 | 10/2008 | Chu et al. |
| 2008/0262596 A1 | 10/2008 | Xiao |
| 2008/0269866 A1 | 10/2008 | Hamer et al. |
| 2008/0269867 A1 | 10/2008 | Johnson |
| 2008/0275542 A1 | 11/2008 | LaDuca |
| 2008/0281399 A1 | 11/2008 | Hartley |
| 2008/0294237 A1 | 11/2008 | Chu |
| 2009/0005847 A1 | 1/2009 | Adams |
| 2009/0012602 A1 | 1/2009 | Quadri |
| 2009/0043373 A1 | 2/2009 | Arnault de la Menardiere et al. |
| 2009/0043377 A1 | 2/2009 | Greenberg et al. |
| 2009/0048663 A1 | 2/2009 | Greenberg |
| 2009/0069880 A1 | 3/2009 | Vonderwalde et al. |
| 2009/0088781 A1 | 4/2009 | Drasler et al. |
| 2009/0099649 A1 | 4/2009 | Chobotov et al. |
| 2009/0109065 A1 | 4/2009 | Pinheiro |
| 2009/0132024 A1 | 5/2009 | Berkhoff |
| 2009/0155337 A1 | 6/2009 | Schreck et al. |
| 2009/0164001 A1 | 6/2009 | Biggs et al. |
| 2009/0240316 A1 | 9/2009 | Bruszewski |
| 2009/0254170 A1 | 10/2009 | Hartley et al. |
| 2009/0259290 A1 | 10/2009 | Bruszewski et al. |
| 2009/0259296 A1 | 10/2009 | McIff et al. |
| 2009/0264985 A1 | 10/2009 | Bruszewski |
| 2009/0287145 A1 | 11/2009 | Cragg et al. |
| 2010/0063575 A1 | 3/2010 | Shalev et al. |
| 2010/0063576 A1 | 3/2010 | Schaeffer et al. |
| 2010/0094390 A1 | 4/2010 | Goldmann et al. |
| 2010/0179638 A1 | 7/2010 | Mayberry et al. |
| 2010/0261662 A1 | 10/2010 | Schreck et al. |
| 2011/0054586 A1 | 3/2011 | Mayberry et al. |
| 2011/0054587 A1 | 3/2011 | Mayberry et al. |
| 2011/0054594 A1 | 3/2011 | Mayberry et al. |
| 2011/0288627 A1 | 11/2011 | Hartley et al. |
| 2012/0109279 A1 | 5/2012 | Mayberry |
| 2014/0249815 A1 | 9/2014 | Schreck |
| 2014/0350658 A1 | 11/2014 | Benary et al. |
| 2015/0173932 A1 | 6/2015 | Mayberry |
| 2015/0366688 A1 | 12/2015 | Schreck |

FOREIGN PATENT DOCUMENTS

| | | |
|---|---|---|
| DE | 295 21 548 U1 | 2/1995 |
| DE | 295 21 776 U1 | 2/1995 |
| DE | 100 17 147 | 10/2001 |
| EP | 0 282 175 | 9/1988 |
| EP | 0 323 176 | 7/1989 |
| EP | 0 177 330 | 6/1991 |
| EP | 0 458 568 | 11/1991 |
| EP | 0 596 145 | 5/1994 |
| EP | 0 621 015 | 10/1994 |
| EP | 0 659 389 | 6/1995 |
| EP | 0 688 545 | 12/1995 |
| EP | 0 689 806 | 1/1996 |
| EP | 0 712 614 | 5/1996 |
| EP | 0 732 088 | 9/1996 |
| EP | 0 732 089 A2 | 9/1996 |
| EP | 0 732 089 A3 | 9/1996 |
| EP | 0 740 928 A1 | 11/1996 |
| EP | 0 740 928 B1 | 11/1996 |
| EP | 0 747 020 | 12/1996 |
| EP | 0 732 089 | 2/1997 |
| EP | 0 775 470 | 5/1997 |
| EP | 0 782 841 | 7/1997 |
| EP | 0 783 873 | 7/1997 |
| EP | 0 783 874 | 7/1997 |
| EP | 0 880 938 | 12/1998 |
| EP | 0 880 948 | 12/1998 |
| EP | 0 904 745 | 3/1999 |
| EP | 0 974 314 | 1/2000 |
| EP | 1 433 438 | 6/2004 |
| EP | 1 470 797 | 10/2004 |
| EP | 0 935 374 | 1/2005 |
| EP | 1 935 374 | 6/2008 |
| EP | 2 429 452 | 3/2012 |
| EP | 2 635 241 | 9/2013 |
| ES | 1 038 606 | 7/1998 |
| JP | 04-25755 | 1/1992 |
| JP | 08-336597 | 12/1996 |
| JP | 9-511160 | 11/1997 |
| JP | 11-188111 A | 7/1999 |
| JP | 2000-500047 | 1/2000 |
| JP | 2007-524442 A | 8/2007 |
| JP | 2007-236472 | 9/2007 |
| JP | 2007-236472 A | 9/2007 |
| JP | 5629871 | 10/2014 |
| WO | WO 93/13825 | 7/1993 |
| WO | WO 94/24961 | 11/1994 |
| WO | WO 95/21592 | 8/1995 |
| WO | WO 96/34580 | 11/1996 |
| WO | WO 96/39999 | 12/1996 |
| WO | WO 96/041689 | 12/1996 |
| WO | WO 97/10757 | 3/1997 |
| WO | WO 97/10777 | 3/1997 |

(56)　References Cited

FOREIGN PATENT DOCUMENTS

| WO | WO 97/014375 | 4/1997 |
| WO | WO 97/019652 | 6/1997 |
| WO | WO 97/028936 | 7/1997 |
| WO | WO 97/033532 | 9/1997 |
| WO | WO 97/045072 | 12/1997 |
| WO | WO 98/002100 | 1/1998 |
| WO | WO 98/011846 | 3/1998 |
| WO | WO 98/027895 | 7/1998 |
| WO | WO 980/027894 | 7/1998 |
| WO | WO 98/053761 | 12/1998 |
| WO | WO 99/013808 | 3/1999 |
| WO | WO 99/029262 | 6/1999 |
| WO | WO 99/044536 | 9/1999 |
| WO | WO 99/047077 | 9/1999 |
| WO | WO 99/053865 | 10/1999 |
| WO | WO 99/058084 | 11/1999 |
| WO | WO 00/033769 | 6/2000 |
| WO | WO 00/053251 | 9/2000 |
| WO | WO 01/003762 | 1/2001 |
| WO | WO 010/26707 | 4/2001 |
| WO | WO 01/067993 | 9/2001 |
| WO | WO 02/39888 | 5/2002 |
| WO | WO 03/094796 | 11/2003 |
| WO | WO 04/047885 | 6/2004 |
| WO | WO 04/089249 | 10/2004 |
| WO | WO 04/105693 | 12/2004 |
| WO | WO 05/037141 | 4/2005 |
| WO | WO 06/028925 | 3/2006 |
| WO | WO 05/037076 | 4/2006 |
| WO | WO 06/047708 | 5/2006 |
| WO | WO 07/027830 | 3/2007 |
| WO | WO 08/034106 | 3/2008 |
| WO | WO 06/036690 | 4/2008 |
| WO | WO 08/083767 | 7/2008 |
| WO | WO 08/086084 | 7/2008 |
| WO | WO 09/000546 | 12/2008 |
| WO | WO 09/105699 | 8/2009 |
| WO | WO 10/127040 | 11/2010 |
| WO | WO 12/061526 | 5/2012 |

OTHER PUBLICATIONS

European Office Action dated Oct. 28, 2015, from application No. 11781956.5.

Japanese Office Action dated Jul. 10, 2017, from application No. 2013-537796.

Japanese Office Action dated Mar. 30, 2017, from application No. 2013-537796.

Japanese Office Action dated May 20, 2016, from application No. 2013-537796.

Japanese Office Action dated Sep. 7, 2015, from application No. 2013-537796.

Non-final Office Action dated May 21, 2015, from U.S. Appl. No. 13/287,907.

US Final Office Action dated Dec. 3, 2015, from U.S. Appl. No. 13/287,907.

US Final Office Action dated Mar. 17, 2020, from U.S. Appl. No. 15/414,499.

US Final Office Action dated Nov. 2, 2016, from U.S. Appl. No. 13/287,907.

US Non-final Office Action dated Apr. 20, 2016, from U.S. Appl. No. 13/287,907.

US Non-Final Office Action dated Aug. 1, 20232, for U.S. Appl. No. 17/882,378.

US Non-Final Office Action dated Aug. 7, 2019, from U.S. Appl. No. 15/414,499.

US Non-Final Office Action dated Jun. 11, 2021, from U.S. Appl. No. 15/414,499.

US Non-final Office Action dated Oct. 22, 2014, from U.S. Appl. No. 13/287,907.

US Notice of Allowance dated Apr. 4, 2022, from U.S. Appl. No. 15/414,499.

Definition of mounted, Dictionary.com, retrieved Nov. 18, 2010 from http://dictionary.com/browse/mounted.

International Preliminary Report on Patentability and Written Opinion re PCT/US2011/059012, issued on May 7, 2013.

International Search Report and Written Opinion re PCT/US2011/059012, dated Jul. 12, 2012.

Minion et al., "Technique of slow deployment of Gore Excluder endograft improves accuracy of placement", J Vasc Surg 43:852-4, 2006.

* cited by examiner

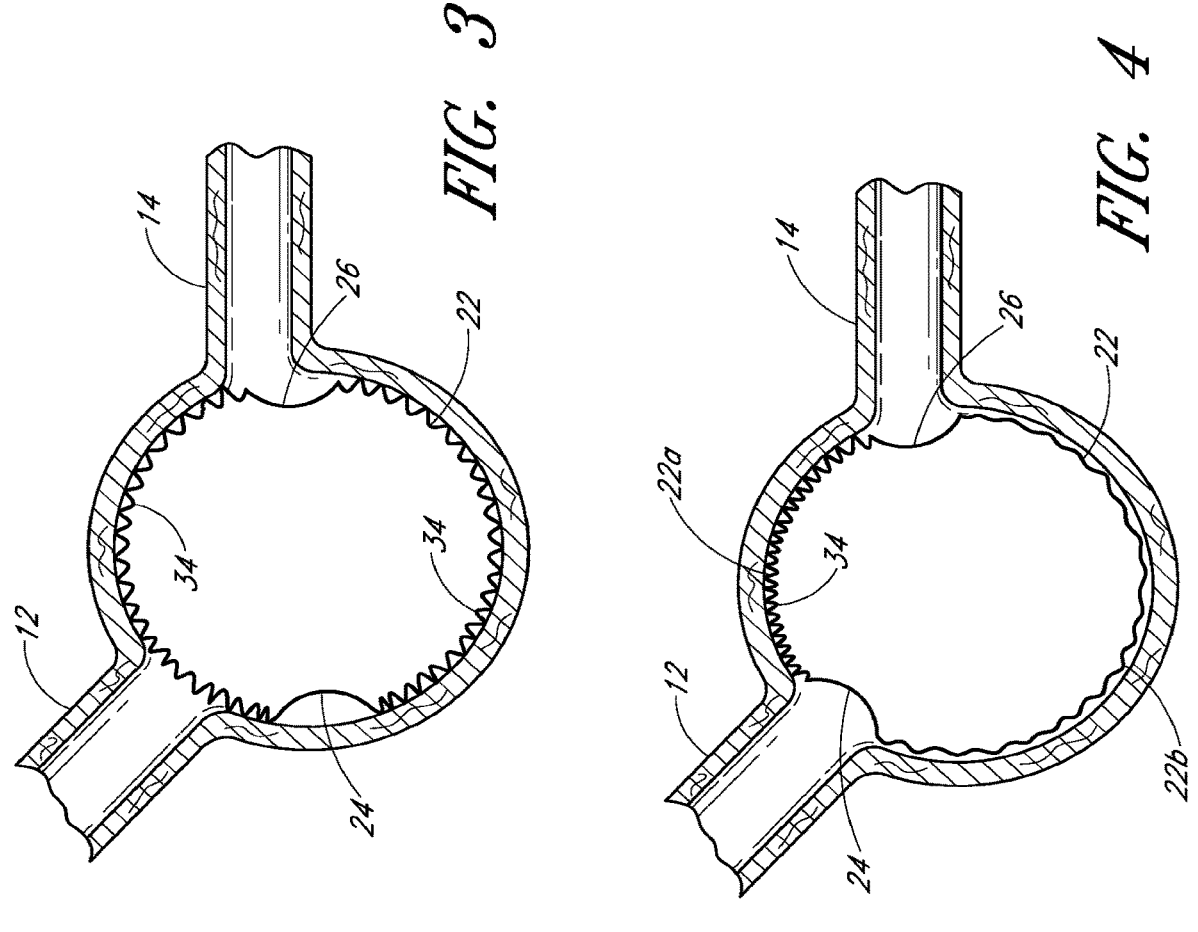
*FIG. 3*
*FIG. 4*
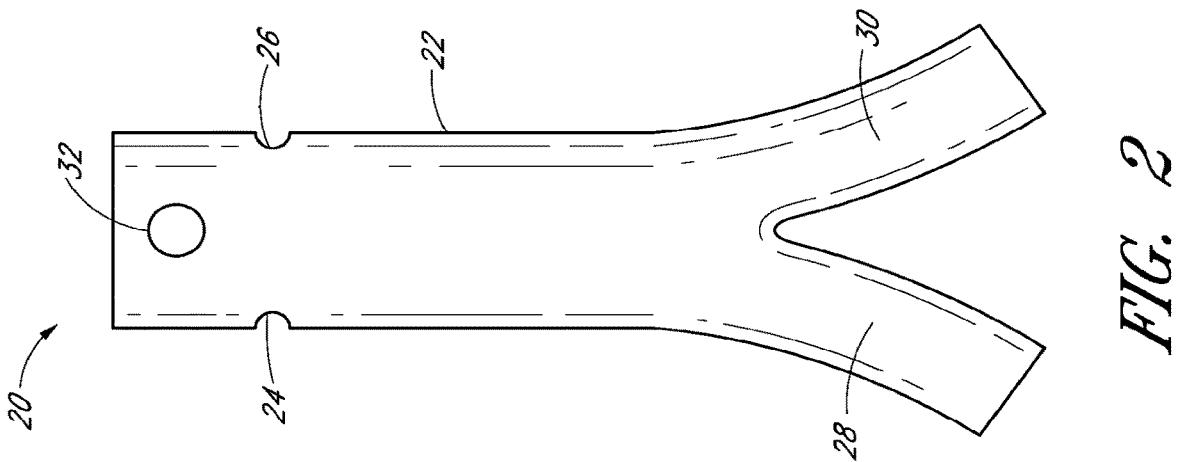
*FIG. 2*

APPARATUS AND METHOD OF PLACEMENT OF A GRAFT OR GRAFT SYSTEM

PRIORITY INFORMATION AND INCORPORATION BY REFERENCE

This application is a continuation of U.S. application Ser. No. 17/882,378, filed Aug. 5, 2022, which is a continuation of U.S. application Ser. No. 15/414,499, filed Jan. 24, 2017, now U.S. Pat. No. 11,406,518, issued Aug. 9, 2022, which is a divisional of U.S. application Ser. No. 13/287,907, (titled "APPARATUS AND METHOD OF PLACEMENT OF A GRAFT OR GRAFT SYSTEM"), filed Nov. 2, 2011, which claims priority benefit of U.S. Provisional Application No. 61/409,504 (titled "APPARATUS AND METHOD OF PLACEMENT OF A GRAFT OR GRAFT SYSTEM"), filed Nov. 2, 2010, which application is hereby incorporated by reference in its entirety as if fully set forth herein. The benefit of priority is claimed under the appropriate legal basis including, without limitation, under 35 U.S.C. § 119 (e). Additionally, U.S. patent application Ser. No. 12/769, 506, filed on Apr. 28, 2010 (entitled "APPARATUS AND METHOD OF PLACEMENT OF A GRAFT OR GRAFT SYSTEM") is also hereby incorporated by reference in its entirety as if fully set forth herein.

BACKGROUND OF THE DISCLOSURE

Technical Field

Endoluminal vascular prostheses delivery devices and methods of deploying such prostheses for use in the treatment of aneurysms at branches of arterial vessels, in particular the aorta, are described.

Description of the Related Art

An abdominal aortic aneurysm is a sac caused by an abnormal dilation of the wall of the aorta, a major artery of the body, as it passes through the abdomen.

In certain conditions, the diseased region of the blood vessels can extend across branch vessels. The blood flow into these branch vessels is critical for the perfusion of the peripheral regions of the body and vital organs. Many arteries branch off the aorta. For example, the carotid arteries supply blood into the brain, the renal arteries supply blood into the kidneys, the superior mesenteric artery ("SMA") supplies the pancreas, the hypogastric arteries supply blood to the reproductive organs, and the subclavian arteries supply blood to the arms. When the aorta is diseased, the branch vessels may also be affected. Thoracic aortic aneurysms may involve the subclavian and carotid arteries, abdominal aneurysms may involve the SMA, renal and hypogastric arteries. Aortic dissections may involve all branch vessels mentioned above. When this occurs, it may be detrimental to implant a conventional tubular graft or stent graft in this location of the aorta or the blood vessel, since such a graft may obstruct the flow of blood from the aorta into the branches.

Prior branch graft arrangements are complex and require many steps of insertion and removal to orient and align fenestrations in a main body to the surrounding anatomy and still more steps to insert, deploy, and seal a branch graft (covered stent) to the main stent graft body and to the wall of the branch vessel without unacceptable leakage.

Thus, there is a need to simplify the delivery of branch graft devices to provide improved reliability and reduced procedure duration.

SUMMARY OF SOME EXEMPLIFYING EMBODIMENTS

Designs and methods of placement of a branch graft or branch graft system having lateral openings in the main graft are disclosed. The main graft is positioned within the main blood vessel such as the aorta so that the lateral openings (also referred to herein as fenestrations) can be aligned with the branch blood vessels, to allow blood to flow through the openings in the main graft and into the branch vessels. The positions of the branch blood vessels can vary from one patient's anatomy to the next, the graft systems disclosed herein allow a surgeon to adjust the position of the fenestrations in the main body so as to align them with the branch vessels to improve the efficiency of branch graft deployment.

The branch graft system can comprise a tubular expandable main body and at least one fenestration or at least one branch graft at any desired location. The main graft body and/or the branch graft can be made from an expandable material, such as but not limited to ePTFE. The main graft can have two fenestrations or branch grafts formed therein at generally diametrically opposed locations or at positions that are offset from the diametrically opposed positions. Depending on the particular patient's anatomy, other cutouts, scallops, or fenestrations, such as but not limited to a fenestration for the superior mesenteric artery ("SMA"), can be formed in the main graft depending on the patient's anatomy and position of the graft.

The main graft body can have a tubular shape and can have a diameter that can be significantly larger than the diameter of the target vessel into which the graft is intended to be deployed. As will be described in greater detail below, the oversized diameter of a portion of the main graft can provide excess or slack graft material in the main graft to allow the fenestrations to each be moved in one or a combination of lateral, axial and angular directions so that the fenestrations can be aligned with the branch arteries.

One or more branch grafts can be supported by the main graft body adjacent to the one or more fenestrations (openings) that can be formed in the main graft body. A compressed branch graft is small enough to allow it to be manipulated into the desired vascular position by moving the branch graft over a guidewire. The branch graft can be expanded to the diameter of the branch vessel by mechanical means, which can be a dilation balloon, or by the removal of a surrounding restraint in the case of a self-expanding device.

Some embodiments relate to a fenestrated graft deployment system, comprising a delivery catheter having a catheter body, a prosthesis having a main graft body, the main graft body having lumen therethrough and a first opening laterally through a wall of the main graft body, a first guidewire prepositioned within the delivery catheter extending through at least a portion of the catheter body into a main lumen of the endoluminal prosthesis and through the first opening in the wall of the prosthesis when the delivery catheter is in a predeployment state. The system can have a first fenestration alignment device extending through at least a portion of the delivery catheter configured to be axially moveable relative to the first guidewire. The first fenestration alignment device can be configured such that a portion of the fenestration alignment device contacts the main graft body adjacent to the first opening to approximately align the first fenestration with an ostium of a target branch vessel when advanced relative to the fenestration.

Some embodiments relate to a fenestration push device for use in a fenestrated prostheses deployment catheter, comprising a body portion defining a lumen therethrough, the lumen having a first diameter or cross-sectional size or perimeter, and a protrusion supported at or adjacent to a distal end of the body portion, the protrusion projecting away from an outside surface of the body portion and defining a second cross-sectional or perimeter size. The second cross-sectional size of the fenestration push device at the location of the protrusion is greater than the first diameter or size of the body portion. Additionally, the second cross-sectional size of the protrusion is greater than a cross-sectional size of a fenestration formed in a respective fenestrated graft.

Some embodiments relate to method of deploying a fenestrated endoluminal prosthesis in a patient's vasculature, comprising advancing a catheter supporting the endoluminal prosthesis therein through a patient's vasculature to a target vessel location, wherein the prosthesis has a main graft body comprising a first opening through a wall thereof, advancing a first guide sheath through the first opening and into a first branch vessel, and advancing a first fenestration alignment device into contact with the prosthesis adjacent to the first opening through the wall of the prosthesis so as to approximately align the first opening with an ostium of the first branch vessel.

Some embodiments or arrangements are directed to methods for deploying an endoluminal prosthesis, comprising advancing a catheter supporting the endoluminal prosthesis therein through a patient's vasculature to a target vessel location, advancing one or more catheters through one or more fenestrations formed in the main graft body and into one or more branch vessels in the patient's vasculature, at least partially expanding at least the second portion of the main graft body, and substantially aligning the one or more fenestrations formed within the second portion of the main graft body with the one or more branch vessels by moving the one or more fenestrations in a circumferential and/or axial direction toward the ostium of the one or more branch vessels. In any of the embodiments or arrangements disclosed herein, the prosthesis can have a main graft body comprising a first portion, a second portion, and a third portion. The second portion of the main graft body has a cross-sectional size that is significantly larger than a cross-sectional size of the first portion and the third portion, and also significantly larger than a cross-sectional size of the target vessel.

Some embodiments or arrangements are directed to methods for deploying a fenestrated prosthesis in a patient's blood vessel having at least a first branch blood vessel, comprising advancing a delivery catheter into a blood vessel, exposing at least one guide sheath, the guide sheath being positioned within the delivery catheter so as to extend from a main lumen of the prosthesis through a first opening formed through a wall of the prosthesis, and advancing an angiographic catheter through the guide sheath and cannulating a first target branch vessel before completely removing the second restraint. The delivery catheter can support the fenestrated prosthesis having a main graft body and at least one fenestration extending through the main graft body, a first restraint restraining a proximal portion of the prosthesis, and a second restraint restraining a distal portion of the prosthesis, the distal portion of the prosthesis being closer to a proximal portion of the delivery catheter than the proximal portion of the prosthesis.

Some embodiments or arrangements are directed to methods for deploying a fenestrated prosthesis in a patient's blood vessel having at least a first branch blood vessel, comprising advancing a delivery catheter into a blood vessel, exposing at least one guide sheath, the guide sheath being positioned within the delivery catheter so as to extend from a main lumen of the prosthesis through a first opening formed through a wall of the prosthesis, and advancing the guide sheath into a first target branch vessel before completely removing the second restraint. The delivery catheter can support the fenestrated prosthesis, and the fenestrated prosthesis can have a main graft body and at least one fenestration therein, a first restraint restraining a proximal portion of the prosthesis, and a second restraint restraining a distal portion of the prosthesis, the distal portion of the prosthesis being closer to a proximal portion of the delivery catheter than the proximal portion of the prosthesis, Some embodiments or arrangements are directed to delivery systems for deploying an endoluminal prosthesis, comprising a first restraint configured to restrain a portion of the prosthesis, a second restraint configured to restrain a second portion of the prosthesis, a first opening through a wall of the prosthesis, a first guide sheath extending from a proximal end of the delivery system into a main lumen of the endoluminal prosthesis and through the first opening in the wall of the prosthesis, a first stent configured to support the first portion of the endoluminal prosthesis, and a second stent configured to support the second portion of the endoluminal prosthesis, wherein the guide sheath is moveable before removing the first and second restraints. The first opening can be positioned between the first and second portions.

Some embodiments or arrangements are directed to endoluminal prostheses comprising a main graft body defining a flow lumen therethrough, a first opening passing through a wall of the main graft body, and a first support member supported by the main graft body and overlapping an edge of the first opening, the first support member being configured to increase the tear resistance of the main graft body adjacent to the first opening.

Some embodiments or arrangements are directed to methods for forming an endoluminal prosthesis having at least one reinforced fenestration in a main portion thereof, comprising forming a graft body having a tubular main body portion, forming a first opening through a wall of the main body portion, the first opening having a first state in which the first opening is substantially unstretched and a second state in which the first opening is stretched so that a size of the first opening increases, advancing a tubular member partially through the first opening, and fastening a first end portion and a second end portion of the tubular member to the wall of the main body portion adjacent to the first opening so that the tubular member completely overlaps an edge of the first opening.

Some embodiments or arrangements are directed to methods of deploying an endoluminal prosthesis, comprising advancing a catheter supporting the endoluminal prosthesis therein through a patient's vasculature to a target vessel location, advancing one or more catheters through one or more fenestrations formed in the main graft body and into one or more branch vessels in the patient's vasculature, at least partially expanding at least the second portion of the main graft body, and substantially aligning the one or more fenestrations formed within the second portion of the main graft body with the one or more branch vessels by moving the one or more fenestrations in a circumferential and/or axial direction toward an ostium of the one or more branch vessels by advancing one or more alignment devices relative to the one or more fenestrations, engaging such fenestrations with the one or more alignment devices, and aligning such fenestrations with the one or more branch vessels. The prosthesis can have a main graft body which can have a first portion, a second portion, and a third portion, and the second portion of the main graft body can have a cross-sectional size that is significantly larger than a cross-sectional size of the first portion and the third portion, and also significantly larger than a cross-sectional size of the target vessel.

Some embodiments or arrangements are directed to methods of deploying a graft in a patient's blood vessel having at least a first branch blood vessel, comprising advancing a delivery catheter into a blood vessel, the delivery catheter supporting a fenestrated prosthesis comprising a main graft body therein, exposing at least one branch sheath, the branch sheath being positioned within the delivery catheter so as to extend from a main lumen of the prosthesis through a first opening formed through a wall of the main graft body, advancing an angiographic catheter into the branch sheath and cannulating a first target branch vessel before expanding the main graft body of the prosthesis, engaging the main graft body adjacent to the first opening, and advancing the main graft body adjacent to the first opening into approximate alignment with an ostium of the target branch blood vessel.

In any of the embodiments disclosed (directly or by incorporation by reference) herein, main graft body, branch grafts, or any other component of the endoluminal prostheses or deployment systems disclosed herein can have at least one radiopaque suture or marker attached thereto to assist with the placement of such components.

BRIEF DESCRIPTION OF THE DRAWINGS

FIG. 2 is a side view of the endoluminal prosthesis illustrated in FIG. 1.

FIG. 3 is a cross-sectional view of the endoluminal prosthesis deployed in the patient's anatomy, taken at 3-3 in FIG. 1, before the fenestrations have been aligned with the respective branch vessels.

FIG. 4 is a cross-sectional view of the endoluminal prosthesis deployed in the patient's anatomy, taken at 3-3 in FIG. 1, after the fenestrations have been aligned with the respective branch vessels.

FIG. 29 is an oblique view of a fenestration alignment component, which is also referred to herein as a fenestration alignment component.

DETAILED DESCRIPTION

Figure 1:
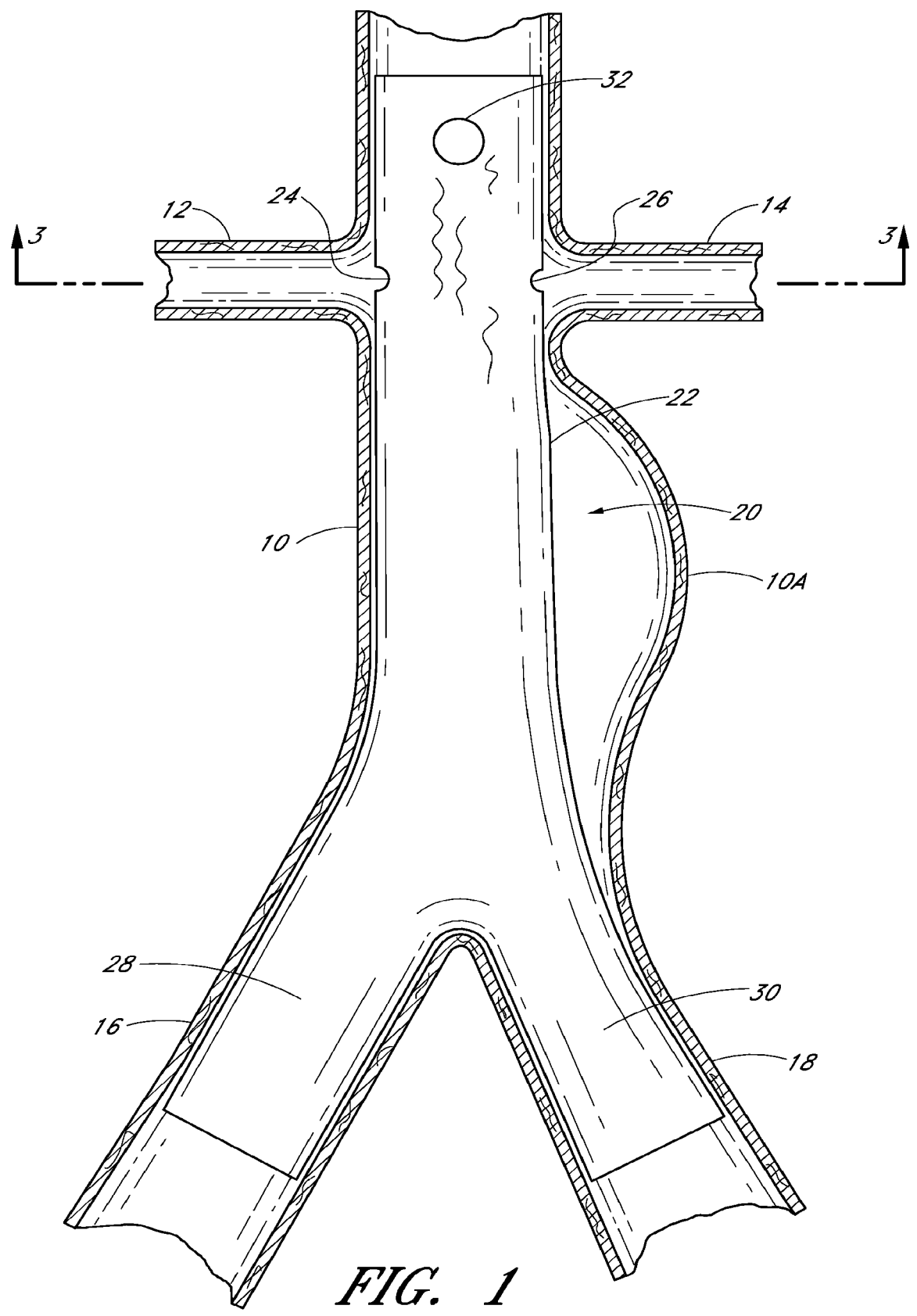
FIG. 1 is a partial sectional view of a patient's vasculature illustrating an endoluminal prosthesis deployed in the patient's vasculature.

In this description, reference is made to the drawings wherein like parts are designated with like numerals throughout the description and the drawings.

Some embodiments described herein are directed to systems, methods, and apparatuses to treat lesions, aneurysms, or other defects in the aorta, including, but not limited to, the thoracic, ascending, and abdominal aorta, to name a few. However, the systems, methods, and apparatuses may have application to other vessels or areas of the body, or to other fields, and such additional applications are intended to form a part of this disclosure. For example, it will be appreciated that the systems, methods, and apparatuses may have application to the treatment of blood vessels in animals.

As will be described, any of the graft embodiments disclosed herein can be configured to have excess or slack graft material in at least a portion thereof relative to the stent or support member which supports the graft. The excess or slack material can result from either an enlarged diametric portion of the graft, excess length of the graft material relative to a stent or other support structure, or a combination of both the enlarged diametric portion of the graft and excess length of the graft material. The excess graft material can form a bulge or other enlargement in the graft in the approximate location of one or more fenestrations formed through the graft material. The excess or slack material along the circumference of the graft (in the enlarged portion of the graft) can allow for circumferential and/or axial movement of the graft material and, hence, can allow for circumferential and/or axial movement of the one or more fenestrations, relative to the stent and the ostium of the patient's branch vessels. Therefore, the diameter of the graft at and/or adjacent to the location of one or more fenestrations through the graft material can be larger than the local diameter of the target vessel. Similarly, the diameter of the graft at and/or adjacent to the location of one or more fenestrations can be larger than the diameter of the non-enlarged portion of the graft material.

For example, any of the embodiments disclosed herein can be configured such that the graft has an enlarged or excess slack portion at or adjacent to the location of the fenestrations, wherein such enlarged or excess slack portion is free of attachment points or has only a minimal number of attachment points to the stent or support structure radially adjacent to the enlarged or excess slack portion. In some embodiments, this can result in both freedom of circumferential and axial movement of the fenestrations, thereby improving the positional adjustability of the fenestrations. The enlarged or excess slack portions of the graft can be radially unsupported by the stent or support member, or can be supported by a stent or support member or by connectors connecting support members positioned axially adjacent to the enlarged or excess slack portion. Accordingly, any of the graft embodiments described herein can be configured to have excess circumferential or longitudinal material at any portion of the graft to increase the positional adjustability of one or more fenestrations formed in the graft.

Further, any of the graft embodiments disclosed herein, including those with diametrically enlarged portions, can have excess graft material in an axial direction. The excess or slack material along the length of the graft can increase the circumferential and/or axial movement of the graft material adjacent to the one or more fenestrations formed in the graft material. Accordingly, the length of the graft material between the proximal and distal attachment points to the stent can be longer than that of the stent between the proximal and distal attachment points. Or, the graft material in a mid-portion of the graft, including on either side of the enlarged portion, can have an increased length relative to the stent adjacent to such graft portion.

FIG. 1 is a partial cross sectional view of a patient's vasculature illustrating an endoluminal prosthesis deployed in the desired position within the patient's vasculature.

As an example, FIG. 1 shows an endoluminal prosthesis deployed in a patient's aorta 10. An aneurysmal sac 10A is also shown. For reference, also illustrated are a patient's first and second renal arteries 12, 14, respectively, and a patient's ipsilateral and contralateral iliac arteries 16, 18, respectively. FIG. 2 is a side view of the endoluminal prosthesis 20 illustrated in FIG. 1. the endoluminal prosthesis 20 illustrated in FIGS. 1 and 2 has a main graft body 22, a first fenestration 24, and a second fenestration 26. The main graft is a bifurcated graft having a first bifurcated branch 28 and a second bifurcated branch 30 for placement in the ipsilateral and contralateral iliac arteries.

The main graft body 22 has a generally cylindrical, tubular shape. The endoluminal prosthesis 20 can be formed from any suitable material, such as, but not limited to, ePTFE. The endoluminal prosthesis 20 is formed from an expandable material. The endoluminal prosthesis 20 is formed such that the main graft body 22 can be sized to be larger than the target vessel into which the main graft body 22 is to be deployed. As illustrated in FIG. 1, the target vessel can be the aortic artery, and the endoluminal prosthesis can be deployed so as to span across an aneurysm in the abdominal aortic.

In any of the graft embodiments disclosed herein, the diameter of the graft body (such as without limitation the main graft body 22) or an enlarged portion of any embodiment of a graft body disclosed herein can be approximately 30% larger than the diameter of the target vessel or the diameter of the non-enlarged portion of the graft body. The diameter of the graft body (such as without limitation the main graft body 22) or an enlarged portion of any embodiment of a graft body disclosed herein can be less than approximately 20%, or from approximately 20% to approximately 50% or more, or from approximately 25% to approximately 40% larger than the target vessel or the diameter of the non-enlarged portion of the graft body, or to or from any values within these ranges.

Further, in any of the graft embodiments disclosed herein, at least a portion of the graft material adjacent to the one or more fenestrations or openings can be free to translate in a circumferential or axial direction relative to the stent that the graft is supported by. For example, particular portions such as the end portions of the graft material can be sutured or otherwise fastened to the stent, while a mid-portion of the graft having one or more fenestrations therethrough can be unattached to the stent so that such mid portion can be free to translate relative to the stent and, hence, permit the adjustability of the fenestrations relative to the stent. In this configuration, the fenestrations can be adjusted to align with the ostium of the patient's branch vessels.

As one non-limiting example, the diameter of the main graft body 22 configured for placement in an approximately 26 mm vessel can be approximately 34 mm in diameter. Therefore, the diameter of the main graft body 22 can be approximately 8 mm larger than the diameter of the target vessel. The diameter of the main graft body 22 can be between approximately 2 mm and approximately 14 mm, or between approximately 4 mm and approximately 12 mm, or between approximately 6 mm and approximately 10 mm larger than the diameter of the target vessel, or to or from any values within these ranges.

The oversized diameter of the main graft body 22 can provide excess or slack graft material in the main graft body 22 such that the fenestrations 24, 26 can each be moved in an axial, rotational, or angular direction, or a combination thereof to align the fenestrations 24, 26 with the branch vessels arteries, as will be described in greater detail below.

As described above, two or more fenestrations can be formed in the main graft body 22 at any desired location. With reference to FIG. 2, the two fenestrations 24, 26 can be formed at generally diametrically opposed locations. However, any number of fenestrations can be formed in the main graft body 22 at any desired locations. Additionally, scallops or cutouts can be formed in the distal end portion or at any suitable location in the main graft body 22, the scallops or cutouts being configured to prevent obstruction of other arteries branching off of the main vessel into which the main graft body 22 is to be deployed. For example, an additional fenestration 32 can be formed in a distal portion of the main graft body 22. The fenestration 32 can be formed so as to align with a patient's SMA FIG. 3 is a cross-sectional view of the endoluminal prosthesis 20 deployed in the patient's anatomy, taken at 3-3 in FIG. 1, as it might appear before the fenestrations 24, 26 have become aligned with the respective branch vessels, for example renal arteries 12, 14. With reference to FIG. 3, the main graft body 22 (which can be oversized) has been deployed in the target vessel. After the main graft body 22 has been deployed in the target vessel, because the main graft body 22 can have a larger diameter than the vessel diameter, folds, wrinkles, or other undulations (collectively referred to as folds) 34 can form in the main graft body 22 about the circumference of the main graft body 22. The folds 34 can form in the main graft body 22 as a result of the fact that there can be excess or slack material in the main graft body 22 after the main graft body 22 has been deployed in the target vessel.

At least a portion of the main graft body 22 can have undulations, folds, bends, corrugations, or other similar features in the axial direction therein when the main graft body 22 is in a relaxed state (i.e., before the graft has been deployed). A middle portion of the graft can have undulations, folds, bends, corrugations or other similar features while the distal or upstream portion defines a smooth contour FIG. 4 is a cross-sectional view of the endoluminal prosthesis 20 deployed in the patient's anatomy, taken at 3-3 in FIG. 1, after the fenestrations 24, 26 have become aligned with the respective branch vessels. With reference to FIG. 4, the oversized main graft body 22 is aligned with the patient's anatomy by the fenestration 24 following a angiographic or guide catheter over which it is threaded to align with the respective branch vessel as the main body is deployed, but after the branch vessel guidewires are positioned in the branch vessels. For example, the fenestration 24 as it moves closer to the fenestration 26, causes a gathering of slack material or folds 34 in a first portion 22a of the main graft body 22 and partially or fully removing the slack material or folds from a second portion 22b of the main graft body 22.

After the main graft body 22 has been positioned within the patient's anatomy such that the fenestrations 24, 26 have been aligned with the respective branch vessels, a covered stent, a bare wire stent, or any other suitable stent or anchoring device can be deployed within the main graft to secure the graft in the desired location (not illustrated). A bare metal stent deployed within the main graft body 22 can compress the folds 34 that are formed in the main graft body 22, if any, against the wall of the vessel and secure the main graft body 22 and the fenestrations 24, 26 in the desired locations.

Alternatively, a supra renal stent can be deployed at a distal or upper portion of the main graft body to secure the distal or upper portion of the main graft body in the desired location within the patient's vasculature, and one or more axial springs can be anchored to the main graft body to provide axial or column strength to the main graft body. The springs can have a helical shape, as illustrated, and can have any suitable size, length, pitch, or diameter. However, such helical shape is not required. The springs can have any suitable shape, including a straight, flat, round, or non-round shape. The springs can be formed from any suitable biocompatible material, such as without limitation stainless steel, Nitinol, or suitable metallic or polymeric materials.

Additionally, any of the features, components, or details of any of the graft, stents, or other apparatuses disclosed in U.S. patent application Ser. No. 12/496,446, filed on Jul. 1, 2009, entitled CATHETER SYSTEM AND METHODS OF USING SAME, U.S. patent application Ser. No. 12/390,346, filed on Feb. 20, 2009, entitled DESIGN AND METHOD OF PLACEMENT OF A GRAFT OR GRAFT SYSTEM, U.S. patent application Ser. No. 12/101,863, filed on Apr. 11, 2008, entitled BIFURCATED GRAFT DEPLOYMENT SYSTEMS AND METHODS, and U.S. Provisional Application 61/409,504, entitled APPARATUS AND METHOD OF PLACEMENT OF A GRAFT OR GRAFT SYSTEM, filed Nov. 2, 2010, can be used, with or without modification, in place of or in combination with any of the features or details of any of the grafts, stents, prostheses, or other components or apparatuses disclosed herein. Similarly, any of the features, components, or details of the delivery apparatuses and deployment methods disclosed in U.S. patent application Ser. Nos. 12/496,446, 12/390,346, and 12/101,863, can be used, with or without modification, to deploy any of grafts, stents, or other apparatuses disclosed herein, or in combination with any of the components or features of the deployment systems disclosed herein. The complete disclosures of U.S. patent application Ser. Nos. 12/496,446, 12/390,346, and 12/101,863 are hereby incorporated by reference as if set forth fully herein.

Figure 5A:
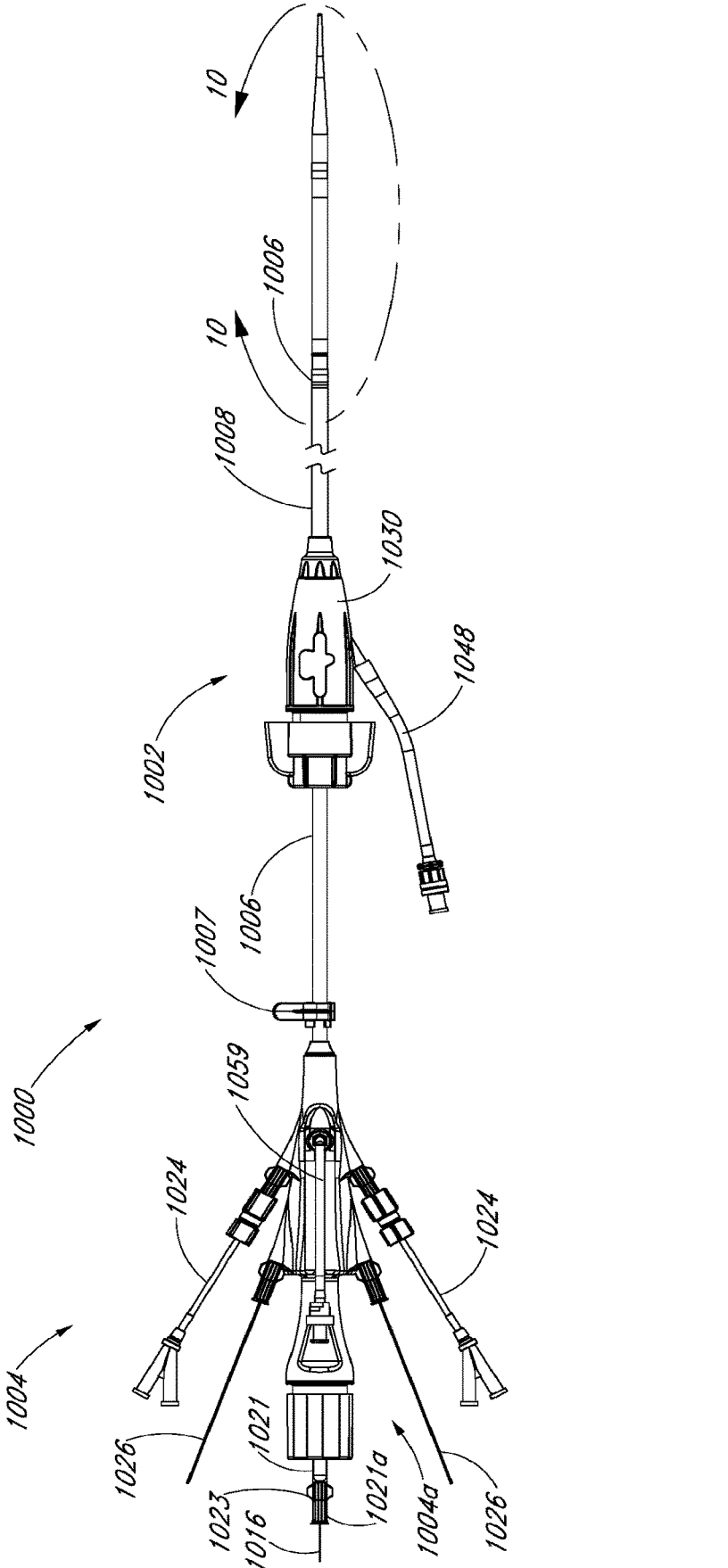
FIG. 5A is a side view of a catheter system comprising an introducer catheter and a delivery catheter.

FIG. 5A is a side view of a catheter system 1000 comprising an introducer catheter 1002 (also referred to as an introducer) and a delivery catheter 1004. The delivery catheter 1004 can be configured for the delivery of an endoluminal prosthesis, including without limitation any endoluminal prosthesis embodiment disclosed herein or any other suitable prosthesis, or for any other suitable use.

Figure 5B:
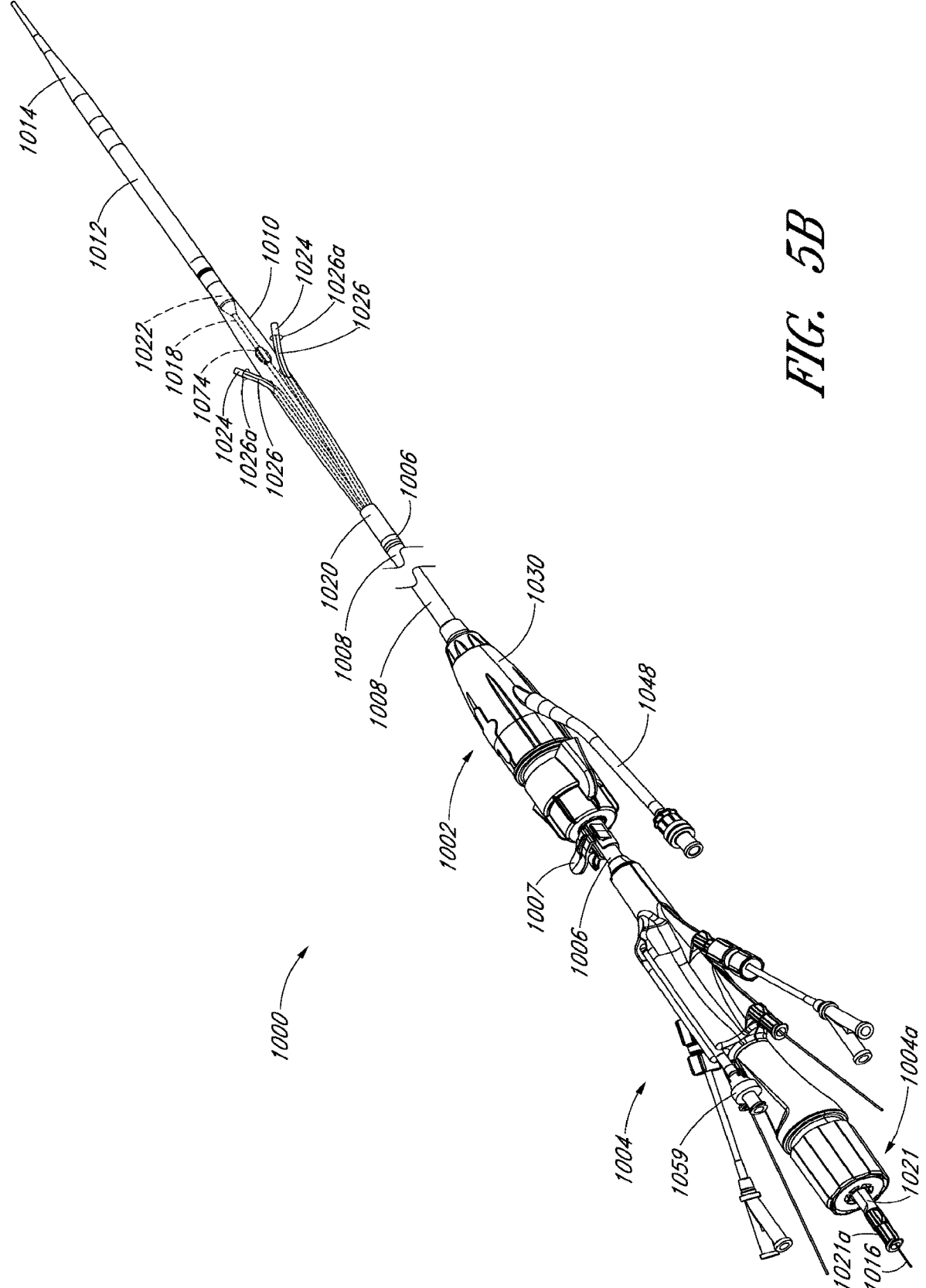
FIG. 5B is an oblique view of a catheter system illustrated in FIG. 5A, showing the outer sheath in a partially retracted position.

FIG. 5B is an oblique view of a catheter system 1000 illustrated in FIG. 5A, showing an outer sheath 1006 of the delivery catheter 1004 in a partially retracted position. With reference to FIGS. 5A and 5B, the outer sheath 1006 can be used to constrain at least a portion of a prosthesis 1010. The prosthesis 1010 can have any of the same features, components, or other details of any of the other prosthesis embodiments disclosed herein, including without limitation the embodiments of the prosthesis 1200 described below. The prosthesis 1010 can have any number of stents or other support members, connectors, grafts, cuts, fenestrations, or other suitable components or features. As used herein, when referring to the prosthesis 1010, distal refers to the end of the prosthesis that is further from the patient's heart, and proximal refers to the end of the prosthesis that is closer to the patient's heart. As used herein with regard to the embodiments of the catheter system 1000, the term distal refers to the end of the catheter system that is further from the surgeon or medical practitioner using the catheter system, and the term proximal refers to the end of the catheter system that is closer to the surgeon or medical practitioner.

As illustrated in FIG. 5B, a distal sheath 1012 (also referred to herein as a first restraint or first restraining means) can be used to constrain a proximal portion of the stent graft 1010. The distal sheath 1012 can be supported by (connected to) a distal tip 1014 of the catheter system 1000. The distal tip 1014 can comprise an atraumatic material and design. As will be described in greater detail below, the distal tip 1014 and, hence, the distal sheath 1012 can be attached to an inner tube 1016 to control the position of the distal tip 1014 and the distal sheath 1012 relative to an inner core 1020 of the delivery catheter 1004. The inner core 1020 can be rotatable relative to the outer sheath 1006 so that a prosthesis supported by the delivery catheter 1004 can be rotated during deployment. The inner tube 1016 can be slidably positioned coaxially within a lumen in an outer tube 1018 that can connect a support member 1022 to the inner core 1020. The outer tube 1018 can be connected to an opening or partial lumen 1019 in the inner core 1020 so as to be axially and rotationally fixed to the inner core 1020.

In this configuration, the catheter system 1000 can be configured such that advancing the inner tube 1016 relative to an inner core 1020 of the delivery catheter 1004 causes the distal sheath 1012 to advance relative to the prosthesis 1010, causing the proximal portion of the prosthesis 1010 to be deployed. The prosthesis 1010 (or any other prosthesis disclosed herein) can be at least partially self-expanding such that, as the tubular distal sheath 1012 is advanced relative to the prosthesis 1010, a proximal portion of the prosthesis 1010 expands against a vessel wall. In some embodiments, only some segments or portions of the prosthesis 1010 such as, portions of the prosthesis axially adjacent to enlarged graft portions of the prosthesis, can be configured to be self-expanding.

The inner core 1020 can be slidably received within the outer sheath 1006 of the delivery catheter 1004. As in the illustrated embodiment, the outer sheath 1006 of the delivery catheter 1004 can be longer than an introducer sheath 1008 of the introducer catheter 1002. Further, a clip 1007 can be supported by the outer sheath 1006 to limit the range of axial movement of the outer sheath 1006 relative to the introducer catheter 1002.

Although not required, a core assembly 1021 can be connected to a proximal end portion of the inner core 1020, the core assembly 1021 having a reduced cross-sectional profile so as to permit one or more sheath members, fenestration alignment components (also referred to herein as fenestration alignment components), or other tubular or other components to pass through the main body of the delivery catheter 1004 and be advanced into one or more lumen within the inner core 1020. The inner core 1020 can be configured to accommodate the insertion of such sheath members, fenestration alignment components, or other tubular components into the lumen of the inner core 1020.

In the illustrated embodiment, a proximal end portion of the core assembly 1021 can comprise a handle member 1023 that is positioned outside a proximal end portion of the delivery catheter 1004 so as to be accessible by a user. The handle member 1023 can be configured to permit a user to axially or rotationally adjust the position of the inner core 1020 relative to the outer sheath 1006.

As discussed above, the inner core 1020, or components axially connected to the inner core 1020 such as the core assembly 1021, can extend proximally past the proximal end portion 1004a of the delivery catheter system 1004 so that a user can adjust and/or change the axial and/or radial position of the inner core 1020 and, hence, the prosthesis 1010, relative to the outer sheath 1006. Similarly, the inner tube 1016 can extend proximally past the proximal end portion 1004a of the delivery catheter 1004 and a proximal end portion 1021a of the core assembly 1021 so that a user can adjust and change the position of the inner tube 1016 relative to the inner core 1020.

In the partially retracted position of the outer sheath 1006 illustrated in FIG. 5B, at least a portion of the prosthesis 1010 supported by the catheter system 1000 can be exposed and, potentially, deployed. A distal portion of the prosthesis 1010 can be exposed and deployed by retracting the outer sheath 1006 relative to the inner core 1020 or distally advancing the inner core 1020 relative to the outer sheath 1006, causing at least a portion of the distal portion of the prosthesis 1010 to self-expand. As will be described, the prosthesis 1010 can be configured to have radially self-expanding support members therein along only a portion or portions of the prosthesis 1010. For example, a graft of the prosthesis 1010 can be radially unsupported at or adjacent to fenestrations formed in the graft. Alternatively, at least the distal portion of the prosthesis 1010 can be constrained within a sheath, such as a peelable sheath. Embodiments of the sheath will be described in greater detail below.

The delivery catheter 1004 can also have one or more branch or guide sheaths 1024 supported thereby. The delivery catheter 1004 can have three or more branch sheaths 1024. Such a configuration can be used for deploying branch stents into one or more branch vessels in the thoracic aorta. Each of the one or more branch sheaths 1024 can be configured to be slidably supported within one or more lumen 1025 formed in the inner core 1020 so that each of the one or more branch sheaths 1024 can be axially advanced or retracted relative to the inner core 1020. Further, the delivery catheter 1004 can be configured such that the branch sheaths 1024 can be rotationally adjusted or twisted relative to the inner core 1020. In some embodiments, each branch sheath 1024 can be positioned within the delivery catheter 1004 such that, in the loaded configuration wherein a prosthesis 1010 is supported (compressed) within the delivery catheter 1004, each branch sheath 1024 is pre-positioned so as to be advanced through a fenestration or branch graft of the prosthesis 1010. Each branch sheath 1024 can be positioned within the delivery catheter 1004 such that a distal end portion of each branch sheath 1024 projects past an end portion of the inner core 1020 and is constrained within the outer sheath 1006. As illustrated in FIGS. 5A-5B, in this configuration, the distal end portion of each branch sheath 1024 can be exposed by retracting the outer sheath 1006 relative to the inner core 1020 and/or the branch sheaths 1024.

Additionally, with reference to FIG. 5B, although not required, the delivery catheter 1004 can have one or more fenestration alignment components 1026 supported thereby. The one or more fenestration alignment components 1026 can be slidably received within one or more lumen 1027 formed in the inner core 1020. The one or more fenestration alignment components 1026 can each have an end portion 1026a that can be sized and configured to surround an outer surface of each of the branch sheaths 1024. The end portion 1026a of each fenestration alignment component 1026 can have, an open or closed annular or circular shape and can be of sufficient size and stiffness to permit a user to engage a fenestration or branch graft formed in or supported by a main body of the prosthesis 1010. For example, as will be described in greater detail below, after the main body of the prosthesis 1010 has been released from the outer sheath 1006 and any other radial restraints, a user can independently or collectively axially advance the fenestration alignment component 1026 over the branch sheaths 1024 such that the end portion 1026a of each fenestration alignment component 1026 contacts the edge or surface adjacent to and surrounding the fenestration or branch graft of the prosthesis 1010 and pushes the fenestration or branch graft toward an ostium of the target branch vessel of the patient's vasculature.

Accordingly, in this configuration, at least a portion of each of the one or more fenestration alignment components 1026 is configured to be slidably supported within a lumen formed in the inner core 1020 so that each of the one or more fenestration alignment components 1026 can be axially advanced relative to the inner core 1020. Further, the delivery catheter 1004 can be configured such that the fenestration alignment components 1026 can be axially or rotationally adjusted or twisted relative to the inner core 1020, for increased maneuverability of the fenestration alignment components 1026.

In some embodiments, each fenestration alignment component 1026 can be positioned within the delivery catheter 1004 such that, in the loaded configuration wherein a prosthesis 1010 is supported (compressed) within the delivery catheter 1004, each fenestration alignment component 1026 is pre-positioned so that the end portion 1026a of each fenestration alignment component 1026 is positioned distal to the end portion of the inner core 1020. In the loaded configuration, each fenestration alignment component 1026 can be positioned such that the end portion 1026a of each fenestration alignment component 1026 is located within the main lumen of the main body of the prosthesis 1010.

The branch sheaths 1024 and fenestration alignment components 1026 can have any suitable size and can be made from any suitable material. For example, the branch sheaths 1024 can have an approximately 6.5 French diameter, or from an approximately 5 Fr diameter or less to an approximately 8 Fr diameter or more, or to or from any values within this range. The fenestration alignment components 1026 can be formed from stainless steel, Nitinol, or any other suitable metallic or non-metallic material, and can have a thickness suitable to prevent the fenestration alignment components 1026 from buckling when axially advanced against a portion of the prosthesis 1010. For example, the fenestration alignment components 1026 can have an approximately 1 Fr diameter, or between approximately a 1 Fr and approximately a 4 Fr diameter. Further, the fenestration alignment component or catheters can be formed from a 0.035 in guidewire or otherwise have a 0.035 in diameter.

Additionally, as will be described below in greater detail, the catheter system 1000 can be configured such that the distal sheath 1012 can be advanced relative to the inner core 1020 and the prosthesis 1010, to expose a proximal portion of the prosthesis 1010. In particular, advancing the distal sheath 1012 can be accomplished by advancing the inner tube 1016 connected to the distal tip 1014 and the distal sheath 1012, so that the distal sheath 1012 releases the proximal portion of the prosthesis 1010. Other details regarding the distal sheath 1012 or methods of using the distal sheath can be found in U.S. Pat. No. 6,953,475, which application is incorporated by reference as if fully set forth herein.

Figure 6:
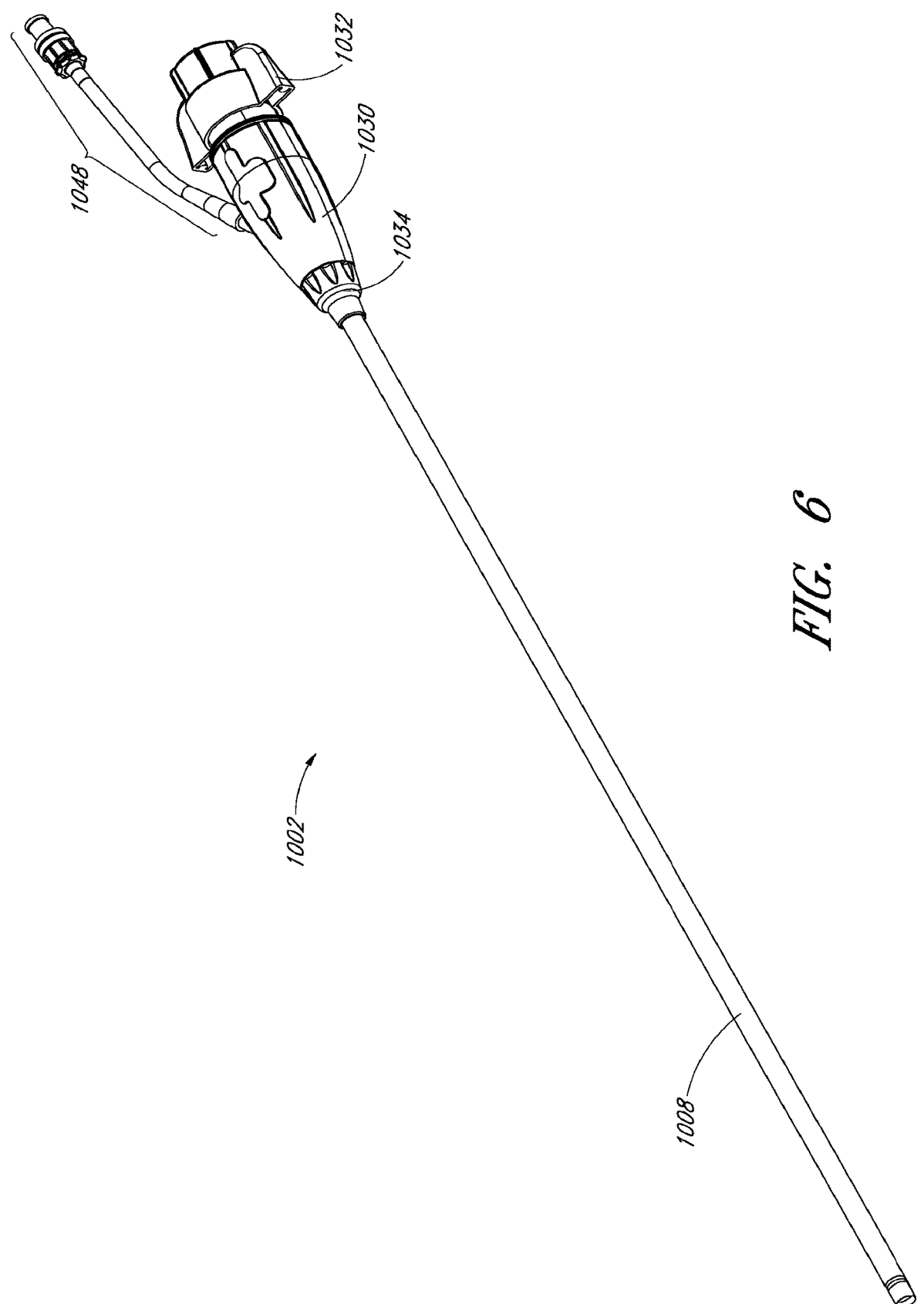
FIG. 6 is an oblique view of introducer catheter shown in FIGS. 5A and 5B.
Figure 7:
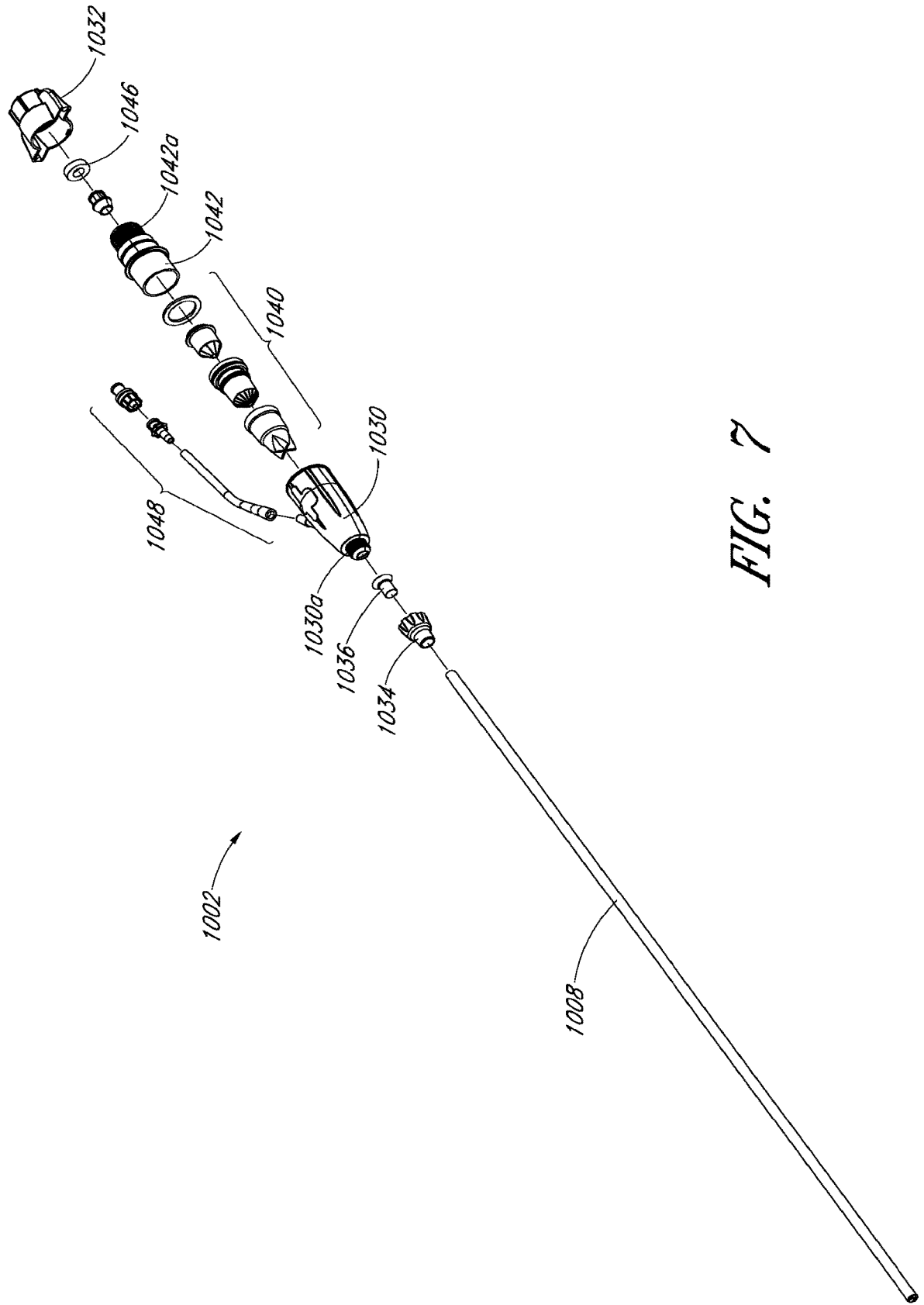
FIG. 7 is an exploded view the introducer catheter shown in FIGS. 5A and 5B.

FIGS. 6 and 7 are oblique and exploded views, respectively, of the introducer catheter 1002 shown in FIG. 5A. The introducer catheter 1002 can have any of the features or components of any of the embodiments disclosed in U.S. patent application Ser. No. 12/496,446, which disclosure is hereby incorporated by reference as if set forth herein. With reference to FIGS. 6-7, the introducer 1002 can have a main body 1030, a threadably engageable hub portion 1032, a threaded cap 1034 configured to threadably engage with a threaded distal end portion 1030a of the main body 1030 so as to secure the outer sheath 1006 to the main body 1030. The outer sheath 1006 can have a flanged end portion 1036 secured thereto or integrally formed therewith. The main body 1030 can support a seal assembly 1040 therein to seal around the inner core 1020 of the delivery catheter 1004 and/or other components of the catheter system 1000. A threaded end member 1042 having a threaded proximal end portion 1042a can be supported by the main body 1030. An annular seal member 1046 can be supported by the main body 1030 of the introducer catheter 1002. The introducer catheter 1002 can be configured such that the seal member 1046 can be adjusted to provide an additional seal around the inner core 1020 of the delivery catheter 1004 by threadably engaging the hub portion 1032. The seal assembly 1040 and seal member 1046 can have any of the details, features, or components of any of the embodiments of the introducer catheter described in U.S. patent application Ser. No. 12/496,446, which application is incorporated by reference as if fully set forth herein.

A tube assembly 1048 can be supported by the main body 1030 of the introducer catheter 1002 so as to provide an orifice or access port into the main body 1030. The tube assembly 1048 can be used to flush the introducer catheter 1002 with saline or other suitable substances at any stage, such as but not limited to prior to the advancement of an endoluminal prosthesis through the introducer catheter 1002 and/or delivery catheter 1004, or prior to other procedures for which another type of delivery catheter may be used. The tube assembly 1048 can support any suitable medical connector and/or valve on the distal end thereof.

Figure 8:
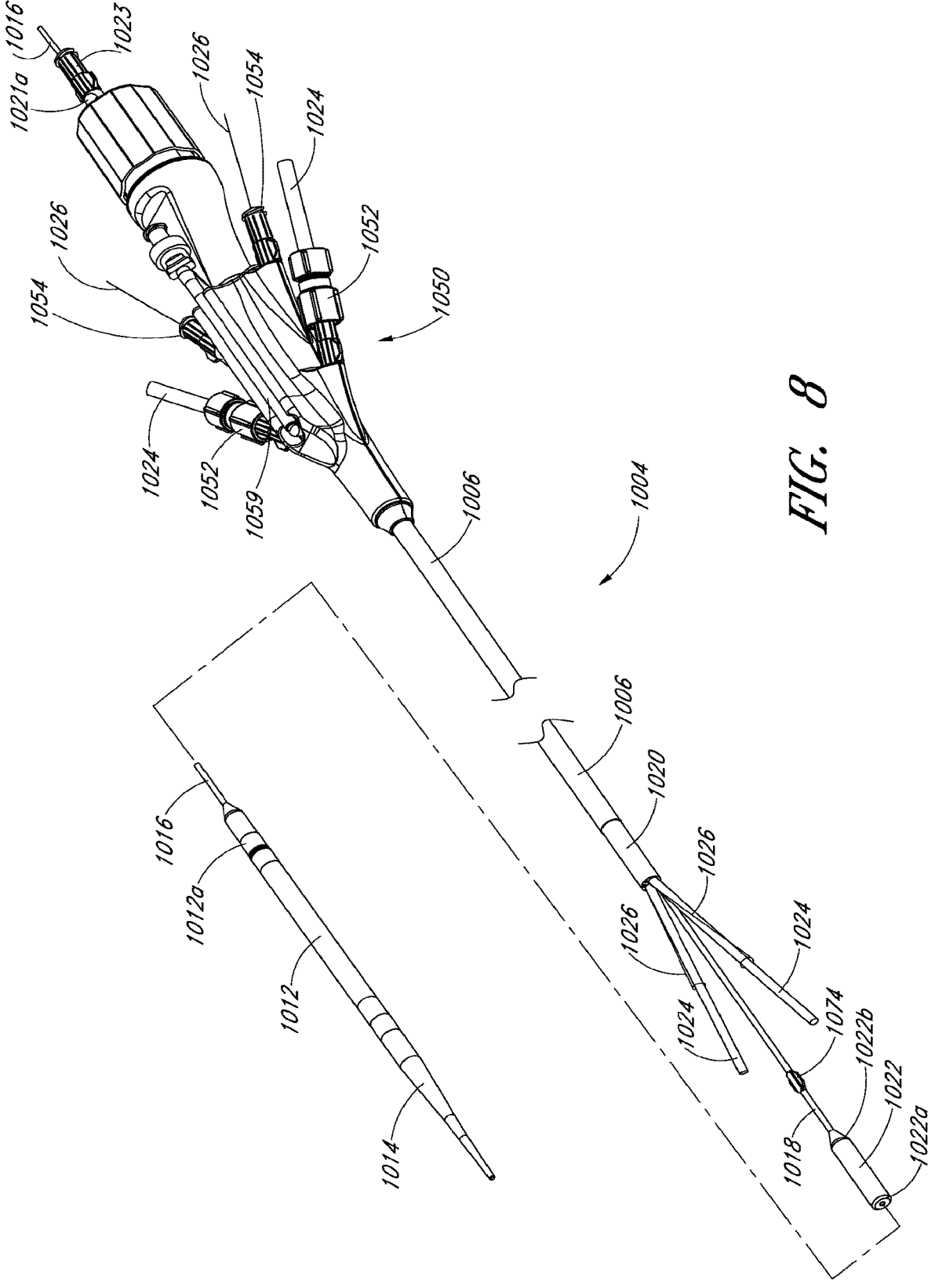
FIG. 8 is a close up view the delivery catheter shown in FIGS. 5A and 5B.
Figure 9:
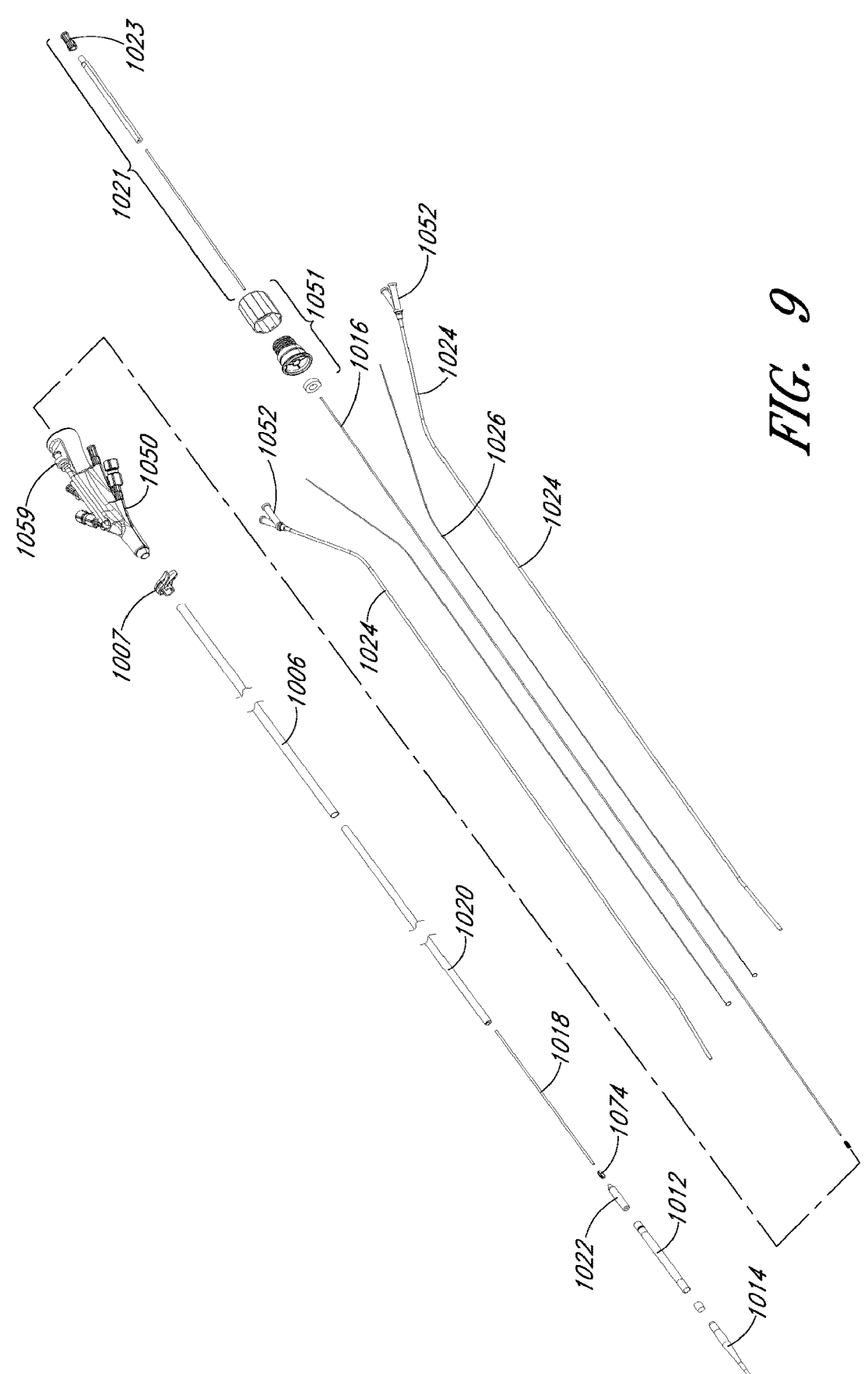
FIG. 9 is an exploded view the delivery catheter shown in FIG. 5A.
Figures 10, 11A, 11B:
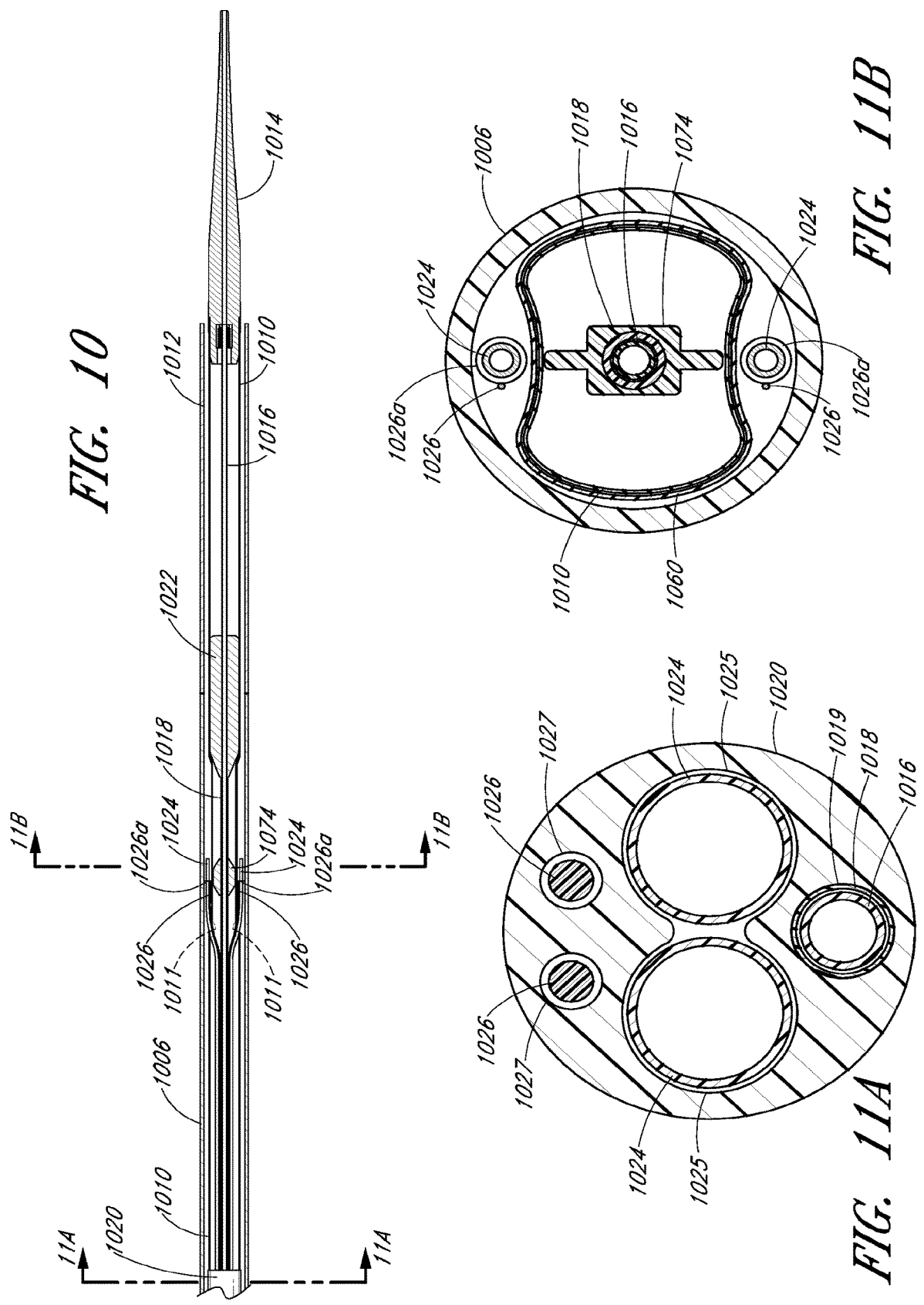
FIG. 10 is a sectional view of a portion 10-10 of delivery catheter shown in FIG. 5A.
FIG. 11A is a sectional view of the delivery catheter shown in FIGS. 5A and 5B, taken at 11A-11A in FIG. 10.
FIG. 11B is a sectional view the delivery catheter shown in FIGS. 5A and 5B, taken at 11B-11B in FIG. 10.

FIGS. 8 and 9 are oblique and exploded views, respectively of the delivery catheter 1004 shown in FIG. 5A. FIG. 10 is a sectional view of a portion 10-10 of the delivery catheter 1004 shown in FIG. 5A. FIG. 11A is a sectional view of the delivery catheter 1004 shown in FIG. 5A, taken at 11A-11A shown in FIG. 10. FIG. 11B is a sectional view of the delivery catheter 1004 shown in FIG. 5A, taken at 11B-11B shown in FIG. 10.

As shown therein, the delivery catheter 1004 can have a main body 1050 that can support the inner core 1020 and/or core assembly 1021, one or more access ports 1052 for the one or more branch sheaths 1024, and one or more access ports 1054 for the one or more fenestration alignment components 1026. The access ports 1052, 1054 can be configured to sealingly tighten around the branch sheaths 1024 or the fenestration alignment components 1026, and to constrict around the branch sheaths 1024 or the fenestration alignment components 1026 so as to substantially axially secure the branch sheaths 1024 or the fenestration alignment components 1026. A scalable cap assembly 1051 can be threadably engaged with the main body 1050 of the delivery catheter 1004. The cap assembly 1051 can be configured such that, when a user tightens the cap assembly 1051 relative to the main body 1050 of the delivery catheter 1004, the core assembly 1021 and/or inner core 1020 will be axially and/or rotational secured to the main body 1050 of the delivery catheter 1004.

A tube assembly 1059 can be supported by the main body 1050 of the delivery catheter 1004 so as to provide an orifice or access port into the main body 1050. The tube assembly 1059 can be used to flush the delivery catheter 1004 with saline or other suitable substances. The tube assembly 1059 can support any suitable medical connector and/or valve on the distal end thereof.

As mentioned above, the support member 1022 can be connected to a distal end portion of the outer tube 1018 so as to be axially engaged by the outer tube 1018. The support member 1022 can have a substantially cylindrical shape and can be sized to fit within the inner lumen of a main body of the prosthesis 1010 when the prosthesis 1010 is in a constrained configuration. As will be described, in the loaded configuration, the prosthesis 1010 can be positioned over the support member 1022 so that a proximal portion of a main body of the prosthesis 1010 is positioned distally of the support member 1022 and so that a distal portion of a main body of the prosthesis 1010 is positioned proximally of the support member 1022. In this configuration, a proximal end portion 1012a of the distal sheath 1012 can be positioned over a distal portion 1022a of the support member 1022, and a distal end portion 1006a of the outer sheath 1006 over a proximal portion 1022b of the support member 1022.

In some embodiments, one or more tab members 1074 can be supported by the outer tube 1018. The one or more tab members 1074 can be configured to increase the rotational engagement of the constrained prosthesis 1010 relative to the outer tube 1018 so that the constrained prosthesis 1010 can be rotated with greater accuracy during deployment. The one or more tab members 1074 can have a generally flat, plate-like shape, such as is illustrated in FIG. 8. The one or more tab members 1074 can be formed from a suitable polymeric or metallic material. The one or more tab members 1074 can comprise one or more radiopaque features or be formed from a radiopaque material to improve the visibility and alignability of the delivery catheter 1004 under fluoroscopy during deployment of the prosthesis 1010.

The one or more tab members 1074 can be similar to any of the embodiments of the torsion tab (such as the torsion tab 196) disclosed in U.S. patent application Ser. No. 12/101, 863, which disclosure is incorporated by reference as if fully set forth herein. The one or more tab members 1074 can be integrally formed with the outer tube 1018, or secured thereto such as by thermal bonding, adhesive bonding, and/or any of a variety of other securing techniques known in the art.

As is illustrated, the main body portion of the prosthesis 1010 can be constrained by a peelable sheath or by the outer sheath 1006 such that the prosthesis 1010 is engaged with the one or more tab members 1074. The one or more tabs 1074 can engage a stent or other portion of an endoskeleton of the prosthesis 1010, or, can engage the material of the graft 1204 surrounding the tab member 1074 so that the prosthesis 1010 can substantially rotate with the inner core 1020 of the deployment catheter 1004.

Figure 12:
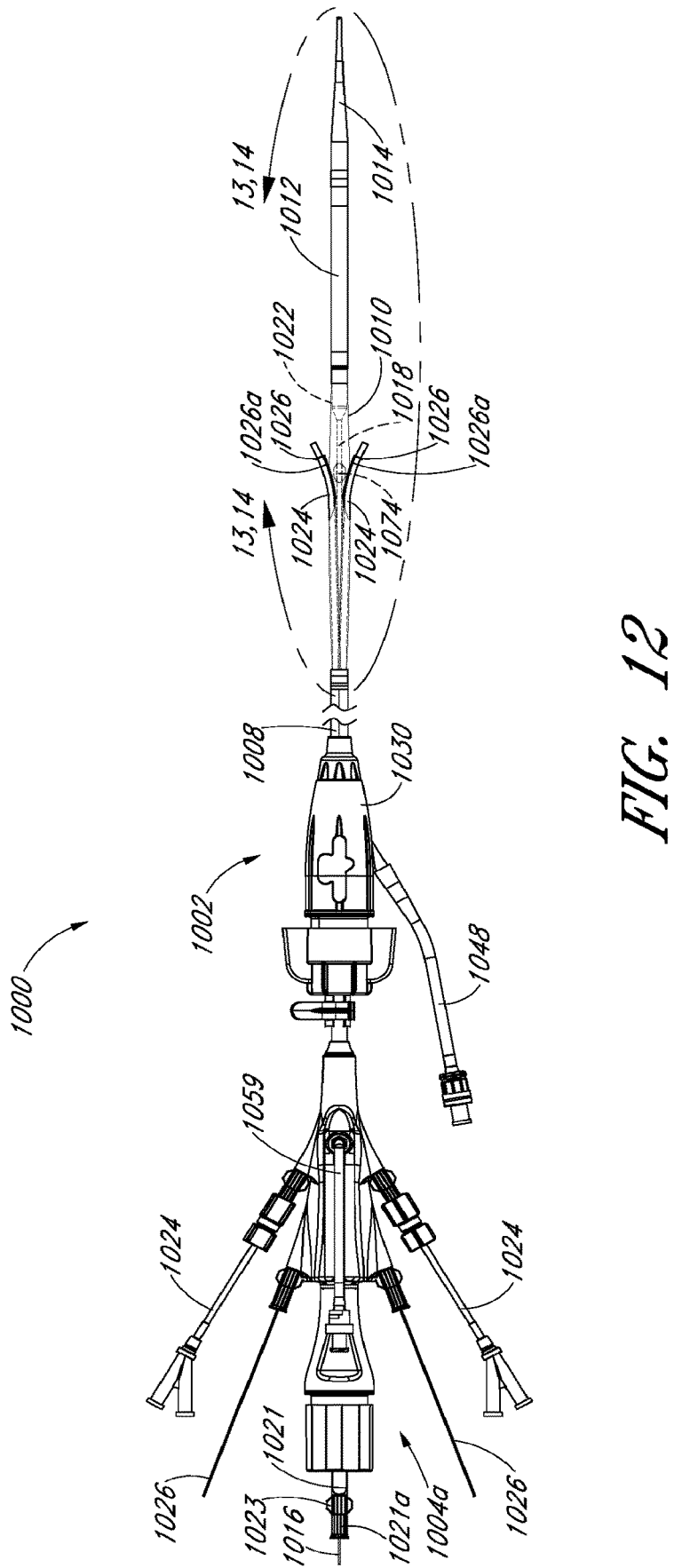
FIG. 12 is a side view the catheter system shown in FIG. 5B, showing the outer sheath in a partially retracted position.
Figures 13, 14:
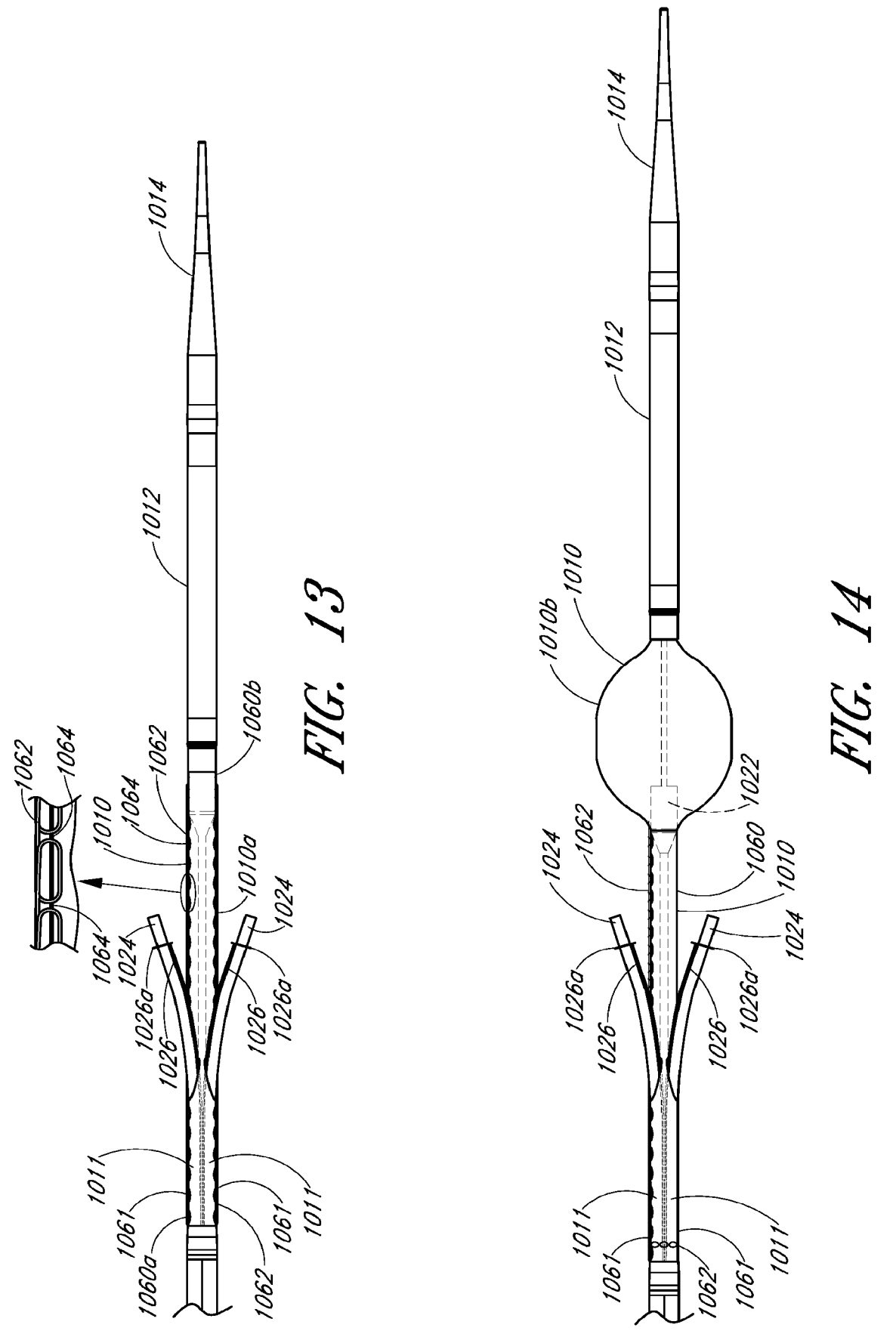
FIG. 13 is an close up side view of the portion 13-13 of the catheter system shown in FIG. 12, showing the outer sheath in a partially retracted position.
FIG. 14 is an close up side view of the portion 14-14 of the catheter system shown in FIG. 12, showing the outer sheath in a partially retracted position and the proximal sheath in a partially advanced position.

FIG. 12 is a side view of the catheter system 1000 showing the outer sheath 1006 in a partially retracted position, similar to the configuration shown in FIG. 5B. FIG. 13 is an enlarged side view of the portion 13-13 of the catheter system shown in FIG. 12.

With reference to FIG. 13, the mid portion of the prosthesis 1010 adjacent to the one or more fenestrations 1011 and/or the distal portion 1010a of the prosthesis can be constrained within a peelable sheath 1060. The peelable sheath 1060 can have a release wire 1062 threadably advanced through a plurality of openings 1064 formed along at least a portion of the sheath 1060. The peelable sheath 1060, release wire 1062, and openings 1064 can have any of the same features, materials, or other details of the similar components disclosed in U.S. patent application Ser. No. 12/101,863, which application is incorporated by reference as if fully set forth herein. The release wire 1062 can be slidably received within a lumen in the inner core 1020 so that a user can retract the release wire 1062 by grasping and retracting a proximal portion of the release wire 1062 positioned outside the patient's body.

However, the mid portion of the prosthesis 1010 adjacent to the one or more fenestrations 1011 and/or the distal portion 1010a of the prosthesis can be constrained within one or more tubular sheaths, such as the outer sheath 1006 (also referred to herein as a second restraint or second restraining means) and/or distal sheath 1012 such that additional restraining means such as the sheath 1060 are not required (not illustrated). Therefore, any of the embodiments disclosed herein having the optional sheath 1060 should be understood to be configurable to not use the sheath 1060 to restrain one or more portions of the prosthesis 1010. The prosthesis 1010 can be configured such that the mid portion of the prosthesis 1010 adjacent to the one or more fenestrations 1011 is not radially supported by a stent, connectors, struts, or any other similar structure such that, when the outer sheath 1006 is partially retracted, the mid portion of the prosthesis does not self-expand.

The prosthesis 1010 can have one or more openings 1011 formed therein. For example and the fenestrations or openings 1011 can be formed in the prosthesis 1010 at diametrically opposing positions. As will be described in greater detail below, one or more of the openings 1011 can be formed in the prosthesis 1010 at a position that is angularly offset from the diametrically opposing position. Similarly, when used, the sheath 1060 can have one or more openings 1061 formed therein, the openings 1061 being positioned adjacent to the similar number of openings 1011 formed in the prosthesis. The catheter system 1000 can be configured such that the sheaths 1024 are advanced through the openings 1011 formed in the prosthesis 1010 and the openings 1061 formed in the sheath 1060, when the prosthesis 1010 is loaded within the catheter system 1000.

With reference to FIG. 11B, due to the non-uniform design of the stent within the graft material, the prosthesis 1010 can be efficiently packed within the outer sheath 1006 so as to surround the sheaths 1024 and efficiently fill the space within the outer sheath 1006. In this configuration, for example, the prosthesis 1010 can be loaded within the outer sheath 1006 so that the sheaths 1024 are advanced between many of the struts, bends, loops, and other features that the stent can comprise, thereby permitting the sheaths 1024 sufficient space to be loaded within the outer sheath 1006 so that the lumen of the sheaths 1024 are not compressed or collapsed in the loaded state. Additionally, the graft can be formed from a bi-directionally expanded, layered PTFE material have thin walls to further increase the space efficiency of the prosthesis 1010.

As illustrated in FIG. 13, where used, the peelable sheath 1060 can have one or more release wires 1062 (two being shown) advanced through openings or perforations 1064 formed in the sheath 1060 along two sides of the sheath 1060. The release wires 1062 can be configured to tear the sheath 1060 along two lines of perforations 1064 and/or scores formed along two sides of the sheath 1060, so that the sheath 1060 can be removed from the prosthesis 1010 while the sheaths 1024 are advanced through the fenestrations 1011, 1061, respectively, in the prosthesis 1010 and sheath 1060. In this configuration, each of the two release wires 1062 can be secured to a proximal end portion 1060a of the sheath 1060, so that both halves of the sheath 1060 can be retracted through the outer sheath 1006.

However, as illustrated in FIG. 14, the catheter system 1000 can be configured to only have one release wire 1062 threadably advanced through the sheath 1060. FIG. 14 is an enlarged side view of the catheter system 1000 shown in FIG. 5A, defined by curve 14-14 shown in FIG. 12, showing the outer sheath 1006 in a partially retracted position and the distal sheath 1012 in a partially advanced position.

The perforations 1064 formed in the sheath 1060 can be arranged along an axial line along the length of the portion of the sheath 1060 from the fenestrations 1061 to the distal end of the sheath 1060, and also arranged to split the sheath 1060 between the two fenestrations 1061 formed in the sheath 1060. As illustrated in FIG. 14, the perforations 1064 formed in the sheath 1060 arranged along the length of the sheath 1060 can be positioned to tear the sheath 1060 from one of the fenestrations 1061 to the distal end 1060b of the sheath 1060, and also to circumferentially tear the sheath 1060 between the fenestrations 1061.

As mentioned above, with reference to FIG. 14, the catheter system 1000 can be configured such that a proximal portion 1010b of the prosthesis 1010 can be deployed by axially advancing the inner tube 1016 relative to the inner core 1020 of the delivery catheter 1004 and, hence, the prosthesis 1010. The prosthesis 1010 can be self-expanding such that removing the radial constraint provided by the distal sheath 1012 can cause the portion of the prosthesis 1010 constrained by the inner tube 1016 to expand toward the vessel wall. The proximal portion 1010b of the prosthesis 1010 can be deployed in this manner before the distal portion 1010a of the prosthesis 1010 is deployed, or simultaneously with the deployment of the distal portion 1010a of the prosthesis 1010. The proximal portion 1010b of the prosthesis 1010 can be deployed in this manner after the distal portion 1010a of the prosthesis 1010 is deployed.

Figure 15:
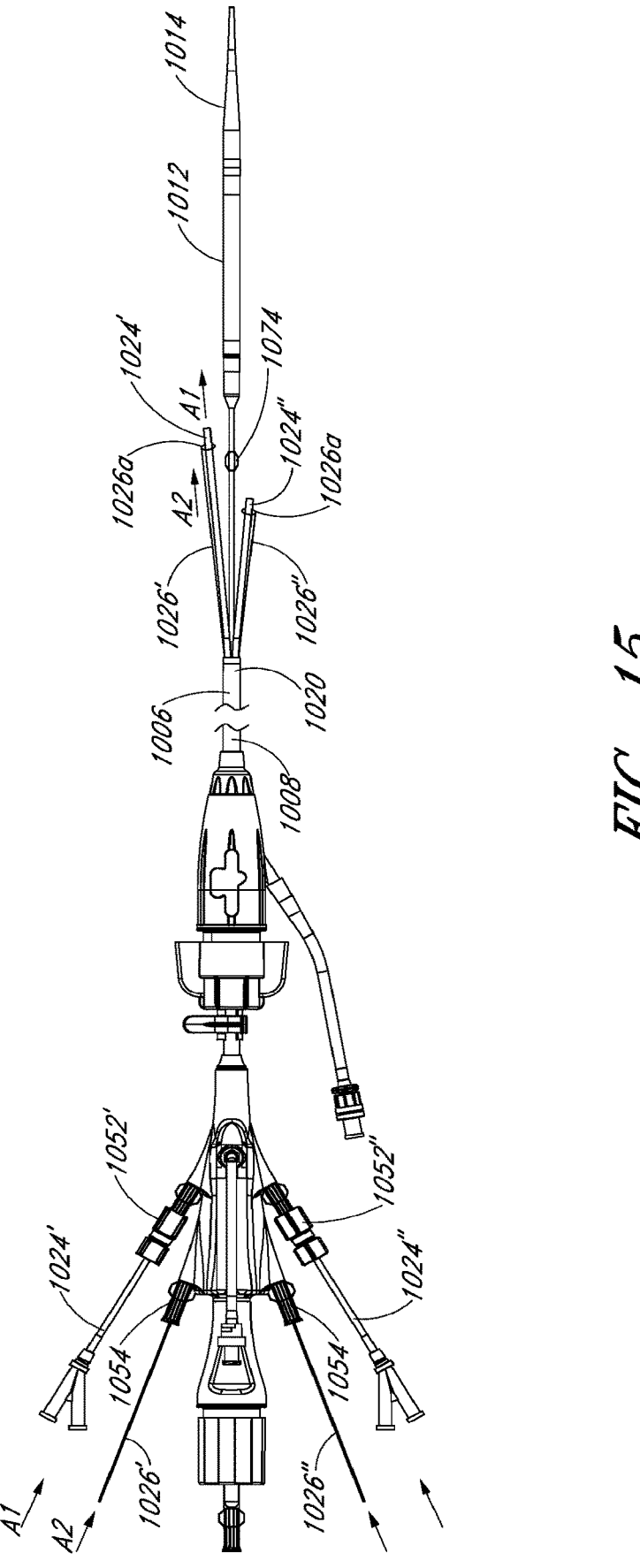
FIG. 15 is a side view the catheter system shown in FIGS. 5A and 5B, showing the outer sheath in a partially retracted position and one branch sheath and one fenestration alignment component in a partially advanced position.

FIG. 15 is a side view of the catheter system 1000 shown in FIG. 5A, showing the outer sheath 1006 in a partially retracted position and one branch sheath 1024' and one fenestration alignment component 1026' in a partially advanced position. The branch sheath 1024' can be advanced relative to the inner core 1020, the prosthesis, and the second branch sheath 1024'' by advancing a proximal portion of the branch sheath 1024' in the direction of arrow A1 in FIG. 15 through the access port 1052' at the proximal end of the delivery catheter 1004. Similarly (not shown), the second branch sheath 1024'' can be advanced relative to the inner core 1020, the prosthesis, and the first branch sheath 1024' by advancing a proximal portion of the branch sheath 1024'' through the access port 1052'' at the proximal end of the delivery catheter 1004. Additionally, either of the fenestration alignment components 1026', 1026'' can be advanced relative to the branch sheaths 1024', 1024'' by advancing the respective fenestration alignment component 1026 through the respective access port 1054. For example, the fenestration alignment component 1026' can be advanced by advancing the proximal portion of the fenestration alignment component 1026' in the direction of arrow A2 in FIG. 15.

Figure 16:
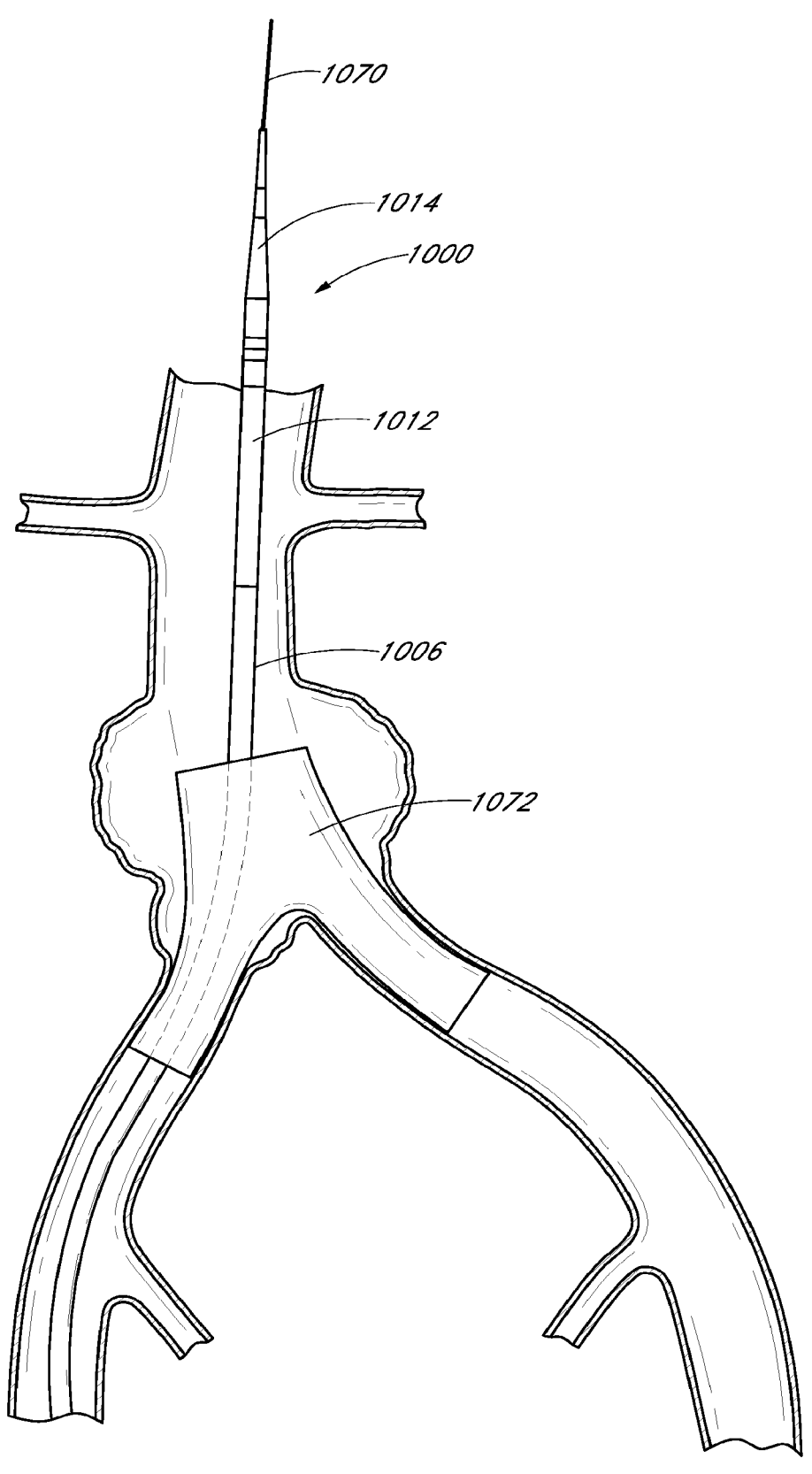
FIG. 16 is a sectional view of a portion of a patient's vasculature, showing the delivery catheter of FIG. 5A being advanced through a patient's abdominal aorta.

With the embodiments of the catheter system 1000 having been described, several configurations of deployment methods for an endoluminal prosthesis, including any suitable prosthesis or any endoluminal prosthesis disclosed herein, will now be described with reference to FIGS. 16-23. FIG. 16 is a sectional view of a portion of a patient's vasculature, showing the delivery catheter 1000 being advanced through a patient's abdominal aorta over a guidewire 1070 positioned within a patient's vasculature. As in the illustrated embodiment, the delivery catheter 1000 can be advanced through a prosthesis 1080 (which can be a bifurcated prosthesis) deployed within the patient's vasculature.

Figure 17:
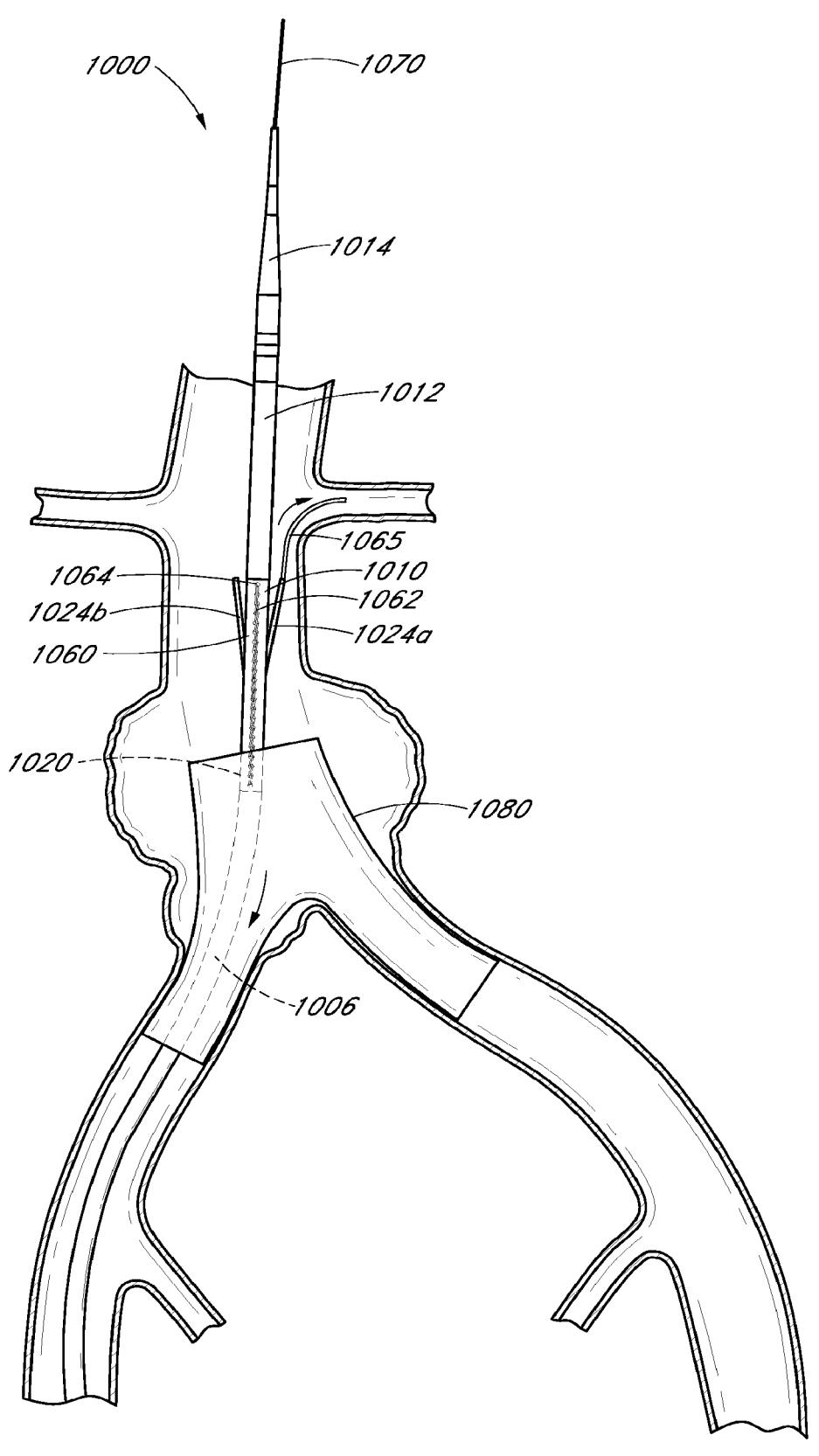
FIG. 17 is a sectional view of a portion of a patient's vasculature, showing the delivery catheter of FIG. 5A and an angiographic catheter being advanced through a branch sheath of the delivery catheter toward a branch vessel.

FIG. 17 is a sectional view of a portion of a patient's vasculature, showing the delivery catheter 1000 and an angiographic catheter 1065 being advanced through a branch sheath 1024 of the delivery catheter toward a target branch vessel. As illustrated, an outer sheath 1006 of the catheter system 1000 has been retracted relative to the inner core (not shown) and the prosthesis 1010, exposing a middle portion of the prosthesis 1010 (i.e., a portion of the prosthesis 1010 radially adjacent to the one or more fenestrations 1011) and the branch sheaths 1024a, 1024b. After the branch sheaths 1024a, 1024b have been exposed, a suitable angiographic catheter 1065 can be advanced through the lumen of either or both of the branch sheaths 1024a, 1024b and directed into the target branch vessel or vessels. A user can rotate the inner core 1020 to approximately rotationally align the fenestrations 1011 of the prosthesis 1010 or the branch sheaths 1024 with the branch vessels.

As discussed above, the optional sheath 1060 can constrain the mid and distal portions of the prosthesis 1010 such that, when the outer sheath 1006 is retracted, the mid and distal portions of the prosthesis 1010 do not self-expand. However, the mid portion of the prosthesis 1010 radially adjacent to the one or more fenestrations 1011 can be unsupported by any stents 1254. In this configuration, the prosthesis 1010 can be configured such that there is no radial force or support provided to the mid portion of the prosthesis 1010, or such that the mid portion of the prosthesis 1010 will not be biased to self-expand when the outer sheath 1006 is retracted. Accordingly, some embodiments can be configured such that no additional restraint in addition to, for example, the outer sheath 1006, is required. Therefore, only the outer sheath 1006 and the distal sheath 1012 can be used to restrain the prosthesis 1010. In this configuration, the outer sheath 1006 can be partially retracted to release the sheaths 1024 so that one or more angiographic catheters 1065 can be advanced through the sheaths 1024 and into the target branch vessels before the proximal and distal portions of the prosthesis 1010 are released from the deployment catheter 1004.

The angiographic catheter 1065 can be configured such that an end portion thereof is biased to have a curved disposition (shape), as is well known in the art.

Figure 18:
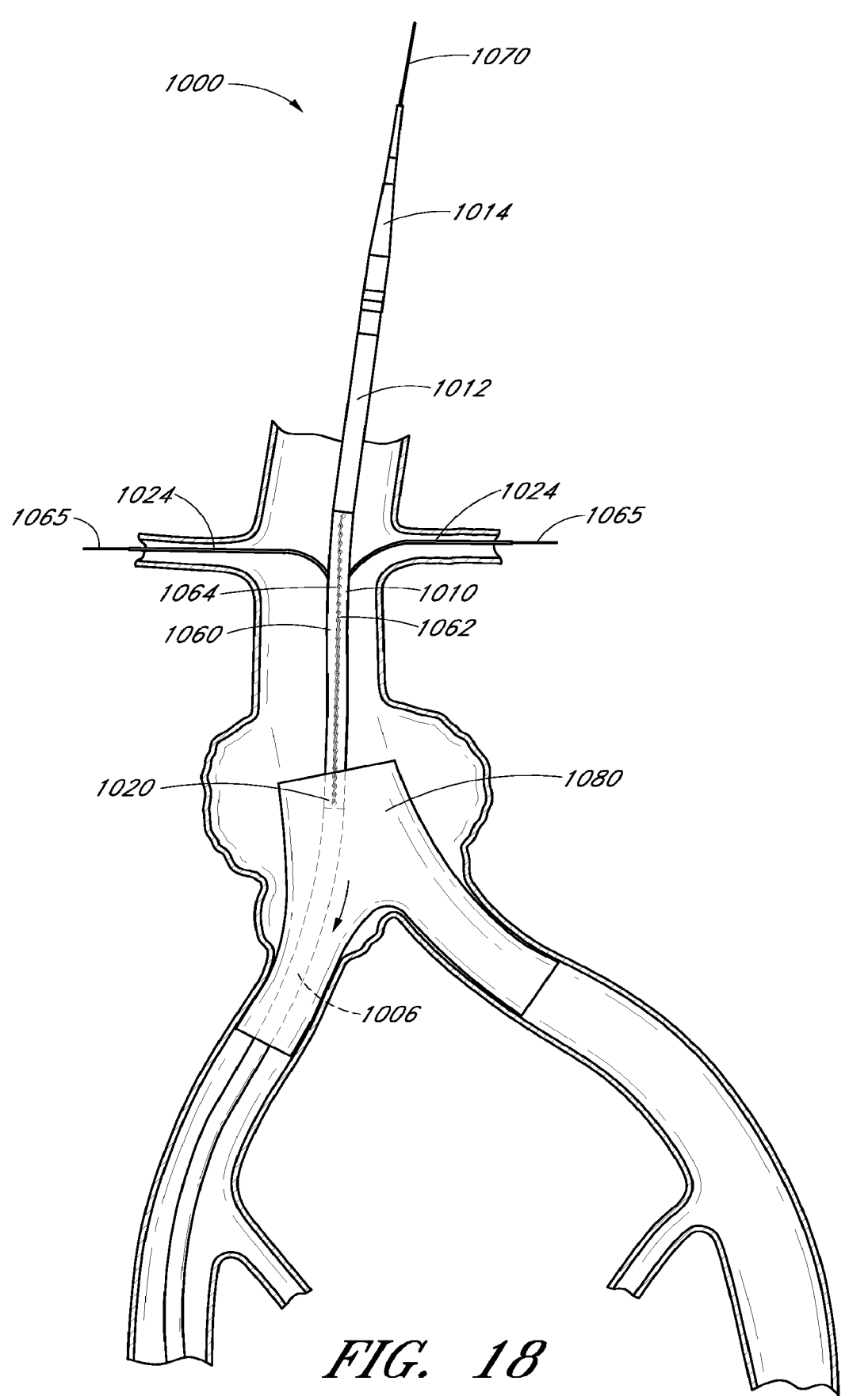
FIG. 18 is a sectional view of a portion of a patient's vasculature, showing the delivery catheter illustrated in FIG. 5A and the branch sheaths of the delivery catheter being advanced into a patient's branch arteries.

As shown, an angiographic catheter 1065 is being advanced relative to the branch sheath 1024a and into the target branch vessel, in this case a renal artery. The delivery catheter 1000 can be configured such that an angiographic catheter can be advanced through the desired branch sheath 1024 and into the target vessel without retracting the outer sheath 1006. After the angiographic catheters 1065 have been directed into the target location, in this case the branch vessels, either or both of the branch sheaths 1024 can be independently or simultaneously advanced over the angiographic catheters 1065 into the target branch vessels, as is illustrated in FIG. 18. The branch sheaths 1024, the fenestrations 1011, 1061 formed in either the prosthesis 1010 or the sheath 1060, respectively, and/or any other components or features of the delivery catheter 1000 can have radiopaque markers or other indicators to assist a medical practitioner in the deployment procedures described herein or other suitable deployment procedures.

Figure 19:
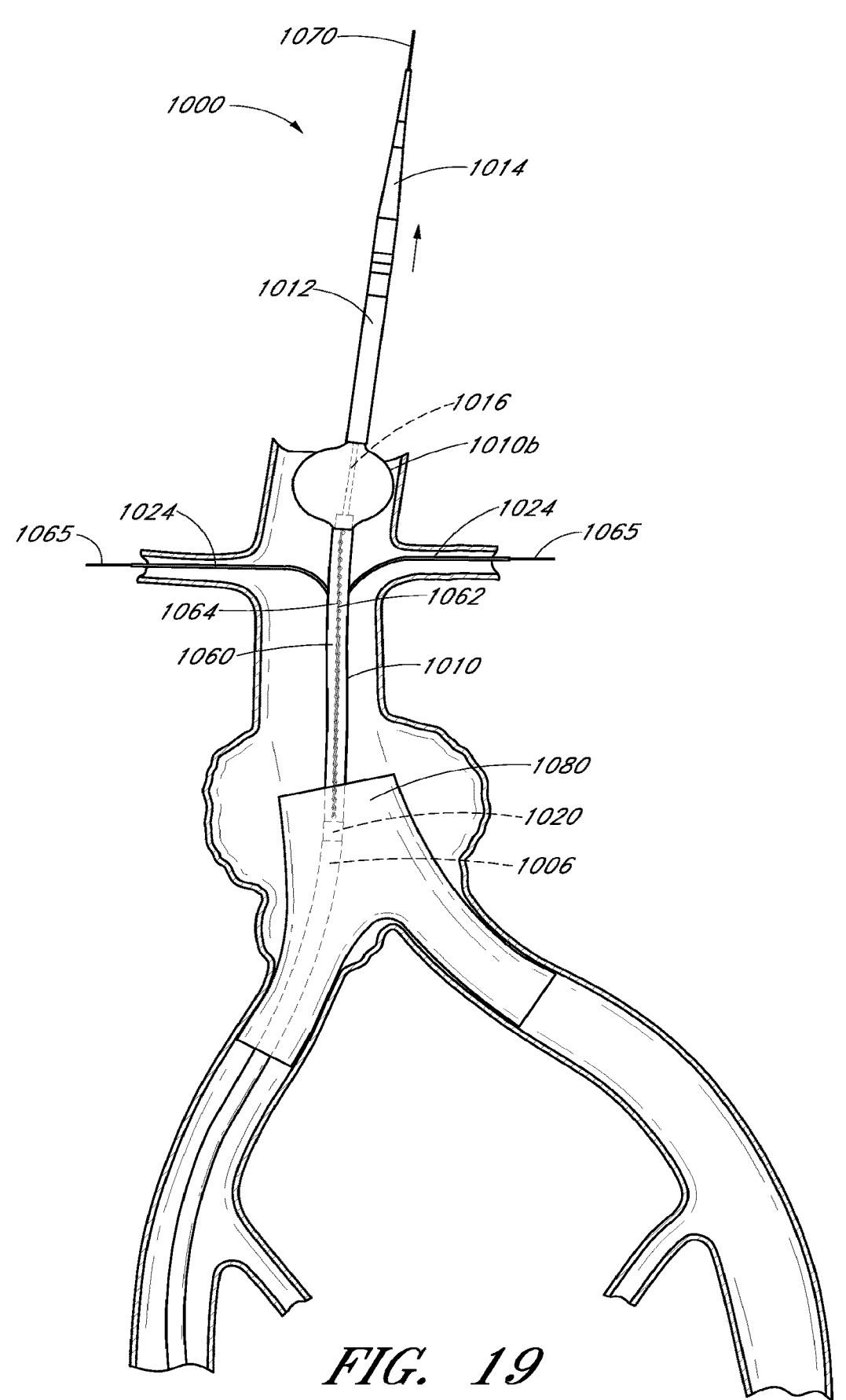
FIG. 19 is a sectional view of a portion of a patient's vasculature, showing a distal sheath of the delivery catheter illustrated in FIG. 5A being advanced to deploy a proximal portion of the prosthesis.

With the branch sheaths 1024 in the target vessels and the outer sheath 1006 axially retracted, as shown in FIG. 19, a proximal portion 1010*b* of the prosthesis 1010 can be deployed by axially advancing the distal sheath 1012 relative to the inner core 1020 and the prosthesis 1010. The prosthesis 1010 can be axially and rotationally secured to the outer tube 1018, which can be axially and rotationally secured to the inner core 1020, such that advancing the distal sheath 1012 relative to the inner core 1020 will advance the distal sheath 1012 relative to the prosthesis 1010. As described above, the distal sheath 1012 can be advanced relative to the inner core 1020 and the prosthesis 1010 by advancing the inner tube 1016 relative to the inner core 1020, the inner tube 1016 being axially engaged with the distal tip 1014 which can support the distal sheath 1012.

Figure 20:
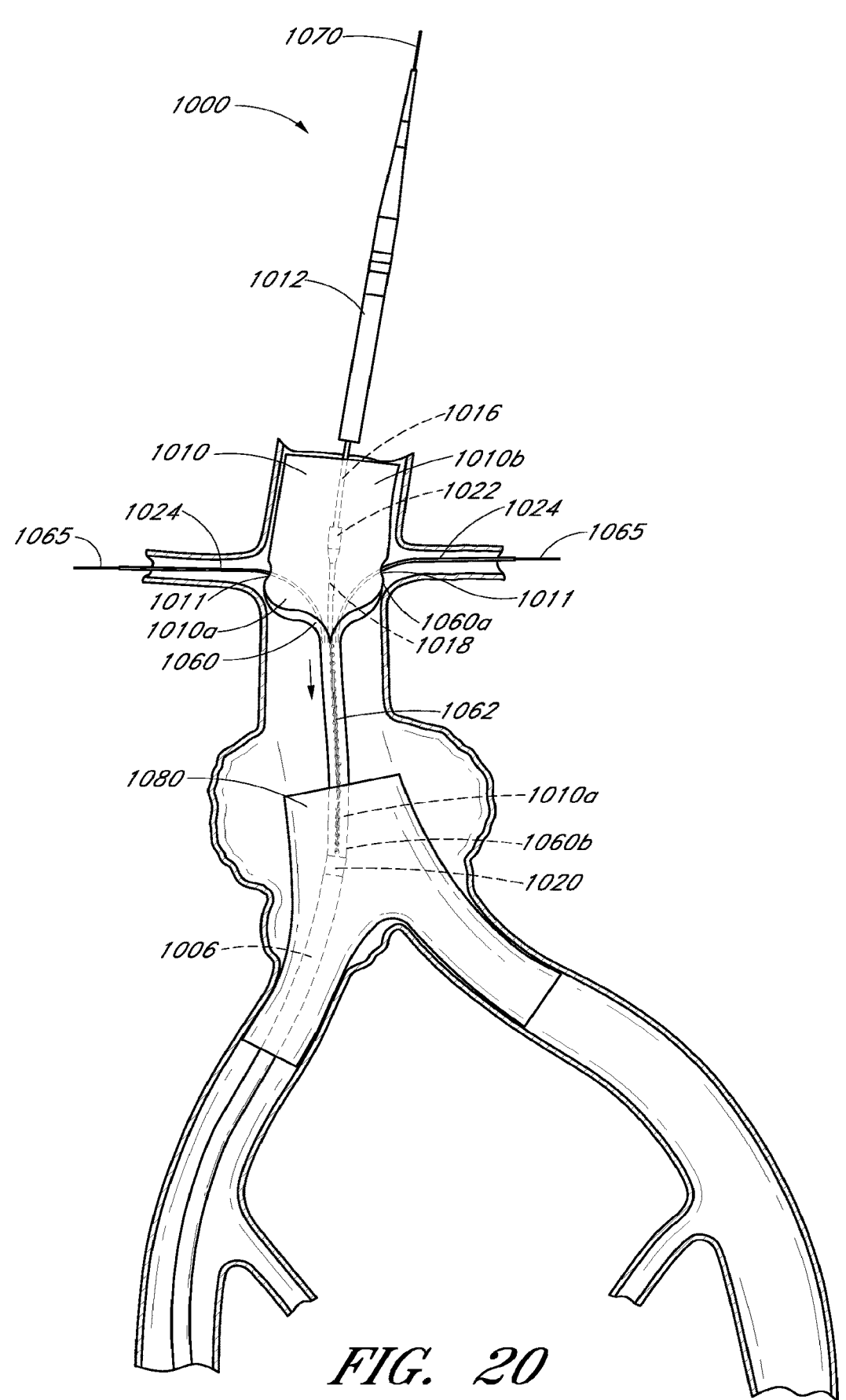
FIG. 20 is a sectional view of a portion of a patient's vasculature, showing a peelable sheath of the delivery catheter illustrated in FIG. 5A being removed to deploy a distal portion of the prosthesis.

FIG. 20 is a sectional view of a portion of a patient's vasculature, showing a peelable sheath 1060 being removed from the distal portion 1010*a* of the prosthesis 1010 so as to deploy a distal portion 1010*a* of the prosthesis 1010. The sheath 1060 can be removed by axially retracting a release wire 1062, which can be looped or other otherwise threaded through openings or perforations 1064 formed in the sheath material. The release wire 1062 can be configured to tear through the sheath material between the perforations 1064, thereby permitting the self-expanding prosthesis 1010 to expand toward the vessel walls. As mentioned, the prosthesis 1010 can be configured to be restrained within the outer sheath 1006 and the distal sheath 1012 such that an additional restraint, such as the peelable sheath 1060, is not required.

As illustrated, a distal portion 1060*a* of the sheath 1060 can be torn by the release wire 1062 before a proximal portion 1060*b* of the sheath 1060 is torn by the release wire so that a proximal portion 1010*b* of the prosthesis (i.e., adjacent to the proximal portion 1060*a* of the sheath 1060) can be deployed before a distal portion 1010*a* of the sheath 1010. A proximal portion 1060*b* or a middle portion of the sheath 1060 can be torn by the release wire 1062 before a distal portion 1060*a* of the sheath 1060 is torn by the release wire (not illustrated). The release wire 1062 can be secured to the proximal portion 1060*b* or other suitable portion of the sheath 1060 such that, after the sheath 1060 has been torn, the sheath 1060 can be removed through the delivery catheter 1000 by continuing to axially retract the release wire 1062 relative to the prosthesis 1010.

As illustrated, a distal portion 1010*a* of the prosthesis 1010 (i.e., the downstream portion of the prosthesis 1010) can be deployed within an opening of an adjacent prosthesis, such as without limitation the bifurcated prosthesis 1080 illustrated in FIG. 20. However, the delivery catheter 1000 or any other delivery catheter described herein can be used to deploy any suitable prosthesis, including a bifurcated prosthesis or otherwise, in any portion of a patient's vasculature. As such, the prosthesis 1010 can be a bifurcated prosthesis.

Figure 21:
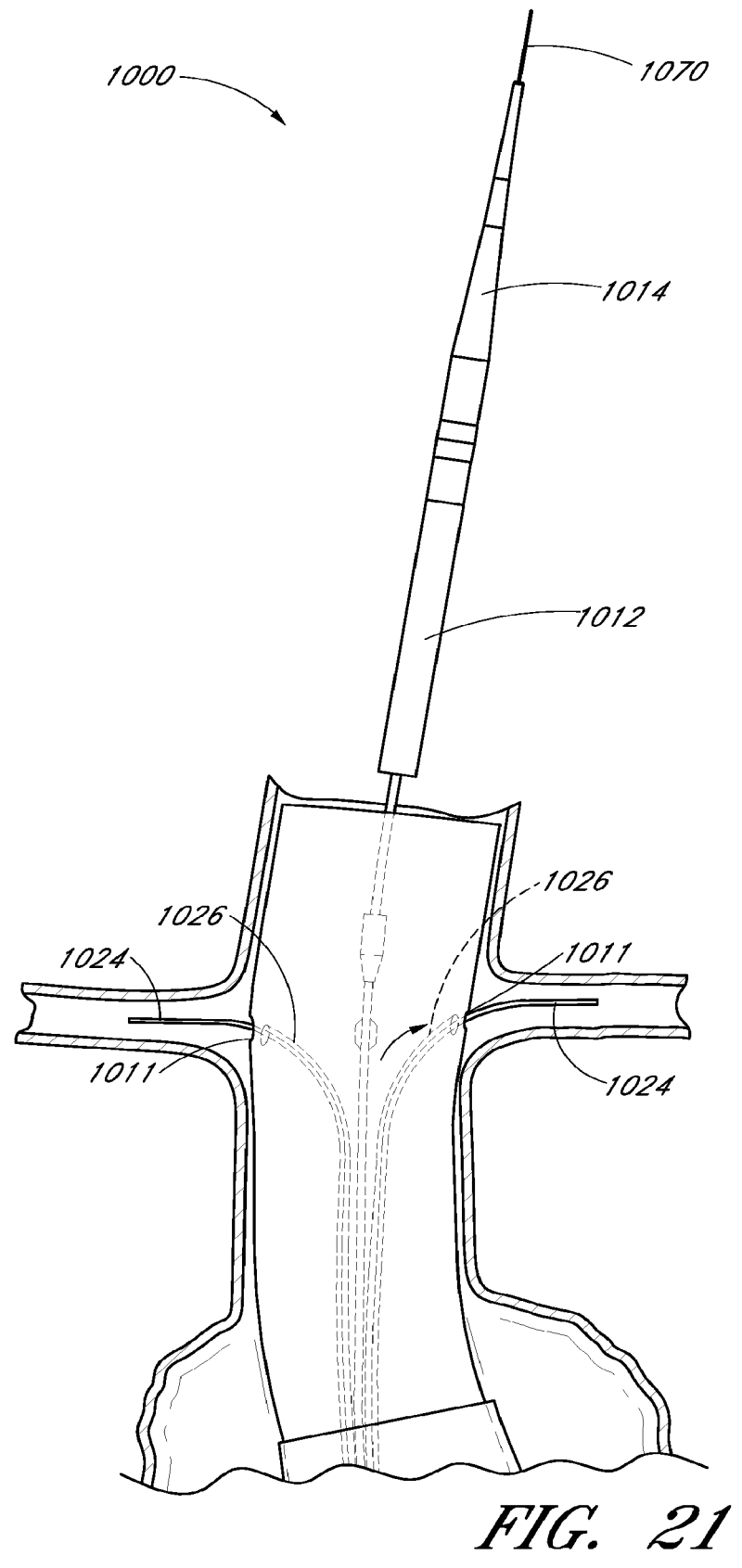
FIG. 21 is a sectional view of a portion of a patient's vasculature, showing a fenestration alignment component of the delivery catheter illustrated in FIG. 5A advancing an inner wall of the prosthesis adjacent to a fenestration toward an ostium of the target branch vessel.
Figure 22:
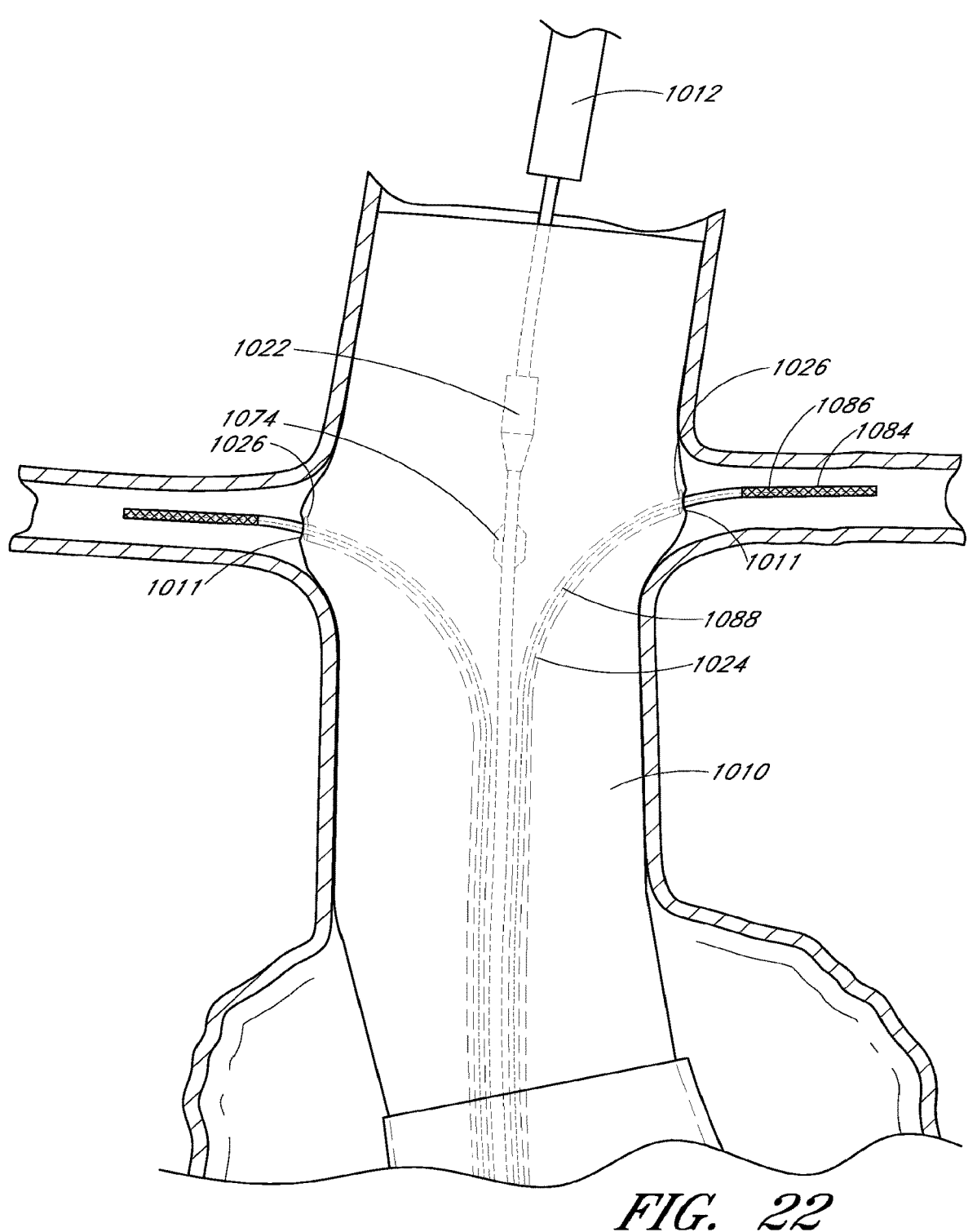
FIG. 22 is a sectional view of a portion of a patient's vasculature, showing a branch stent being advanced into the target branch vessel.
Figure 23:
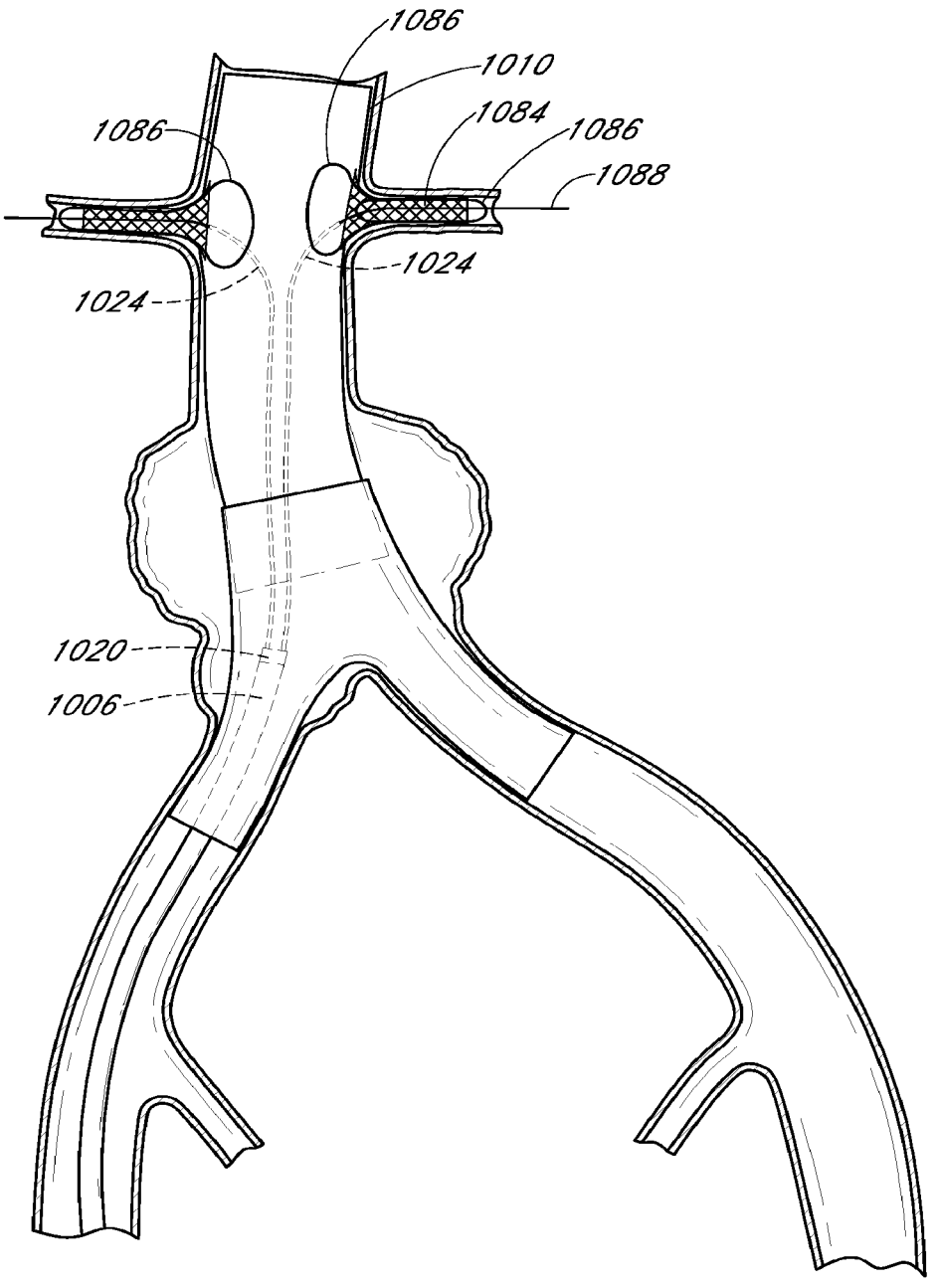
FIG. 23 is a sectional view of a portion of a patient's vasculature, showing the branch stent of FIG. 22 being expanded in the target branch vessel and flared.

FIG. 21 is a sectional view of a portion of a patient's vasculature, showing a fenestration alignment component 1026 contacting and pushing an inner wall of the prosthesis 1010 adjacent to a fenestration 1011 toward an ostium of the target branch vessel. As illustrated, the fenestration alignment component 1026 can be advanced through a lumen in the inner core 1020 to push the fenestration 1011 of the prosthesis 1010 over the branch sheath 1024 and into approximate alignment with the ostium of the branch vessel. The catheter system 1000 can be configured to not have a fenestration alignment component 1026, and can accordingly be configured to deploy a fenestrated graft without the use of such a component As illustrated in FIG. 22, a covered or uncovered branch stent 1084 can be deployed in the branch vessel by advancing the branch stent 1084 through the branch sheath 1024 using a suitable catheter, such as a renal stent catheter, into the target vessel, after the angiographic catheter has been removed from the branch sheath 1024. The stent 1084 can be supported on an inflation balloon 1086, which can be supported by a guidewire 1088. The guidewire 1088 can be configured to have an inflation lumen therein, to inflate the balloon 1086 and expand the branch stent 1084 in the target location after the branch sheath 1024 has been at least partially retracted so as to not interfere with the expansion of the branch stent 1084, as illustrated in FIG. 23. The inflation balloon 1086 can be configured to expand and flare a portion of the stent 1084 within or to the inside of the fenestration 1011 formed in the prosthesis.

The fenestration alignment component 1026 described above can be configured to be supported within a renal or branch stent delivery catheter. For example, the fenestration alignment component 1026 can be configured to be supported within a modified renal stent catheter, such as the renal stent catheter illustrated in FIG. 22. The fenestration alignment component 1026 can be configured to only partially surround the branch sheath 1024 or the branch stent delivery catheter. In this configuration, the fenestration alignment component 1026 can be configured to be entirely positioned within and advanceable through a lumen of the branch sheath 1024 or the branch stent delivery catheter. For example, the fenestration alignment component 1026 can have an expandable end portion that can automatically expand when the end portion is advanced past the end of the lumen, so as to enable the end portion to snare or engage the graft material surrounding the fenestration.

Additionally, the branch stent delivery catheter can be configured to have a snare, protrusion, or other object tethered to the balloon or stent, or to be projecting from an outside surface thereof to snare or engage the graft material adjacent to the fenestration, so as to cause the fenestration to be advanced toward the ostium as the branch stent delivery catheter is advanced through the fenestrations. For example, the branch stent delivery catheter can have a biased wire member supported on an outside surface of the branch stent delivery catheter that is biased to expand when the wire member is advanced past the end of the branch sheath 1024. The wire member can expand to a size that is larger than the size of the fenestration. The wire member can be supported at a position that is offset from an end of the branch stent delivery catheter.

The fenestration 1011 in the prosthesis 1010 can expand as the branch stent 1084 is being expanded, to improve the seal between the fenestration 1011 and the branch stent 1084. A second expansion balloon can be positioned in the portion of the stent 1084 within or to the inside of the fenestration 1011 to flare that portion of the stent 1084, either with or without removing the first balloon used to expand the main portion of the branch stent 1084.

Some arrangements are directed to methods of deploying an endoluminal prosthesis, such as without limitation the prosthesis 1010 described above, comprising inserting a delivery catheter such as catheter system 1000 into an artery, exposing one or more branch sheaths 1024, advancing one or more angiographic catheters having one or more guidewires into the one or more branch sheaths 1024 and cannulating the target branch vessels, advancing the one or more branch sheaths 1024 over the angiographic catheters and into the target branch vessels, advancing the wall of the prosthesis adjacent to each of one or more fenestrations in the prosthesis toward the ostium of the target branch vessels, removing the one or more angiographic catheters and/or guidewires, inserting one or more branch stents into the branch vessels, retracting the branch sheaths, expanding the branch stents, and flaring a portion of the branch stents. In some arrangements, the target branch vessels are the renal arteries. Some arrangements also comprise deploying a proximal and distal portion of the prosthesis. The steps of the foregoing procedure can be performed in the sequence described, or can be performed in any suitable sequence.

Embodiments are directed to apparatuses for placing a prosthesis across at least one branch vessel, the prosthesis having a distal end, a proximal end, a midsection, and at least one lateral opening in the midsection of the prosthesis. The prosthesis can be constrained in a delivery system having a distal and a proximal end. The apparatus can comprise a catheter extending from the proximal end of the delivery system through the lateral opening in the prosthesis, wherein a guidewire can be passed from the proximal end of the delivery system through the catheter, into the branch vessel with at least the proximal and distal ends of the prosthesis remaining constrained in the delivery system. The prosthesis can be a stent graft.

Figure 24A:
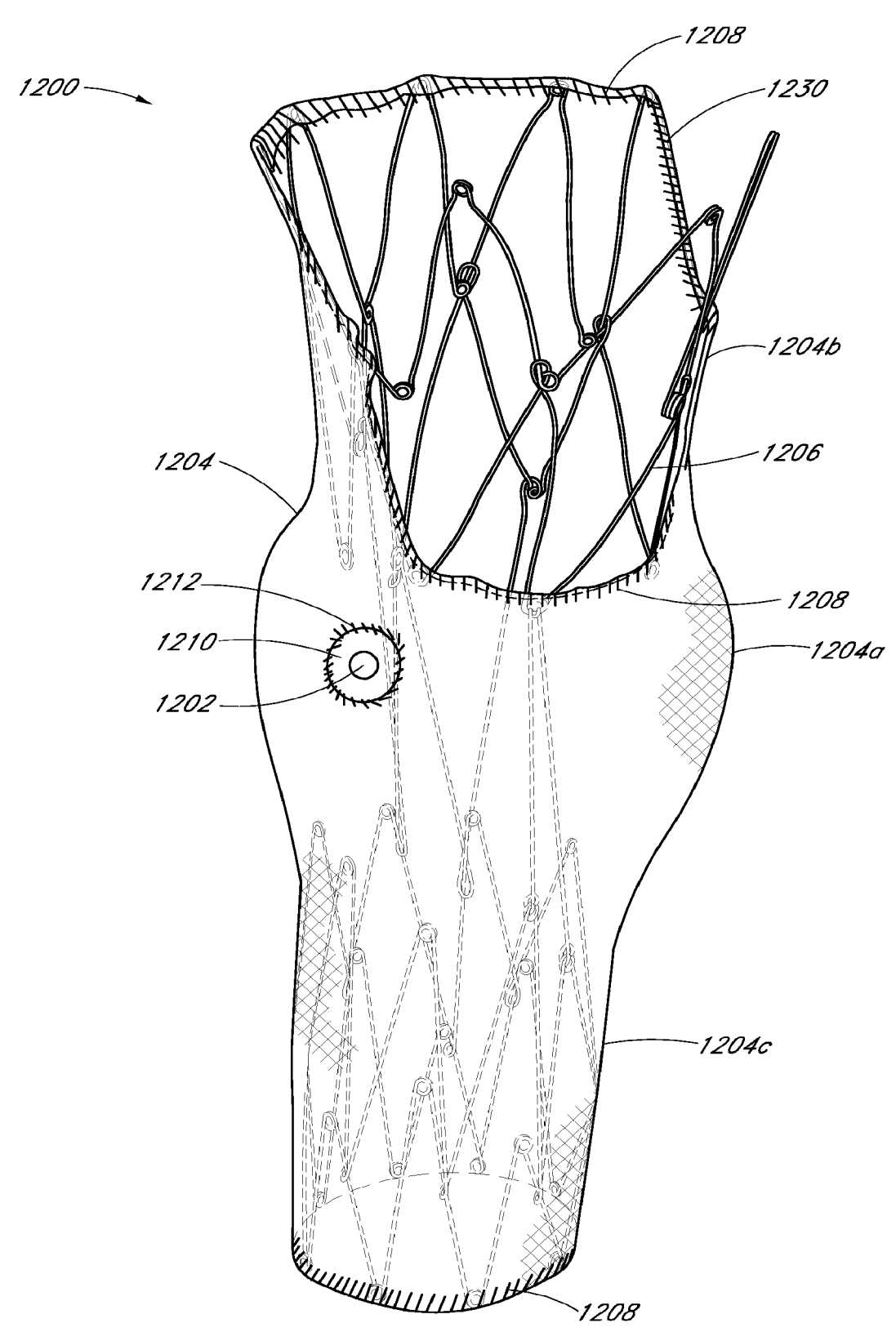
FIGS. 24A and 24B are oblique views of a prosthesis having one or more fenestrations therein, the graft being shown in dashed lines in FIG. 24B for clarity.
Figure 24B:
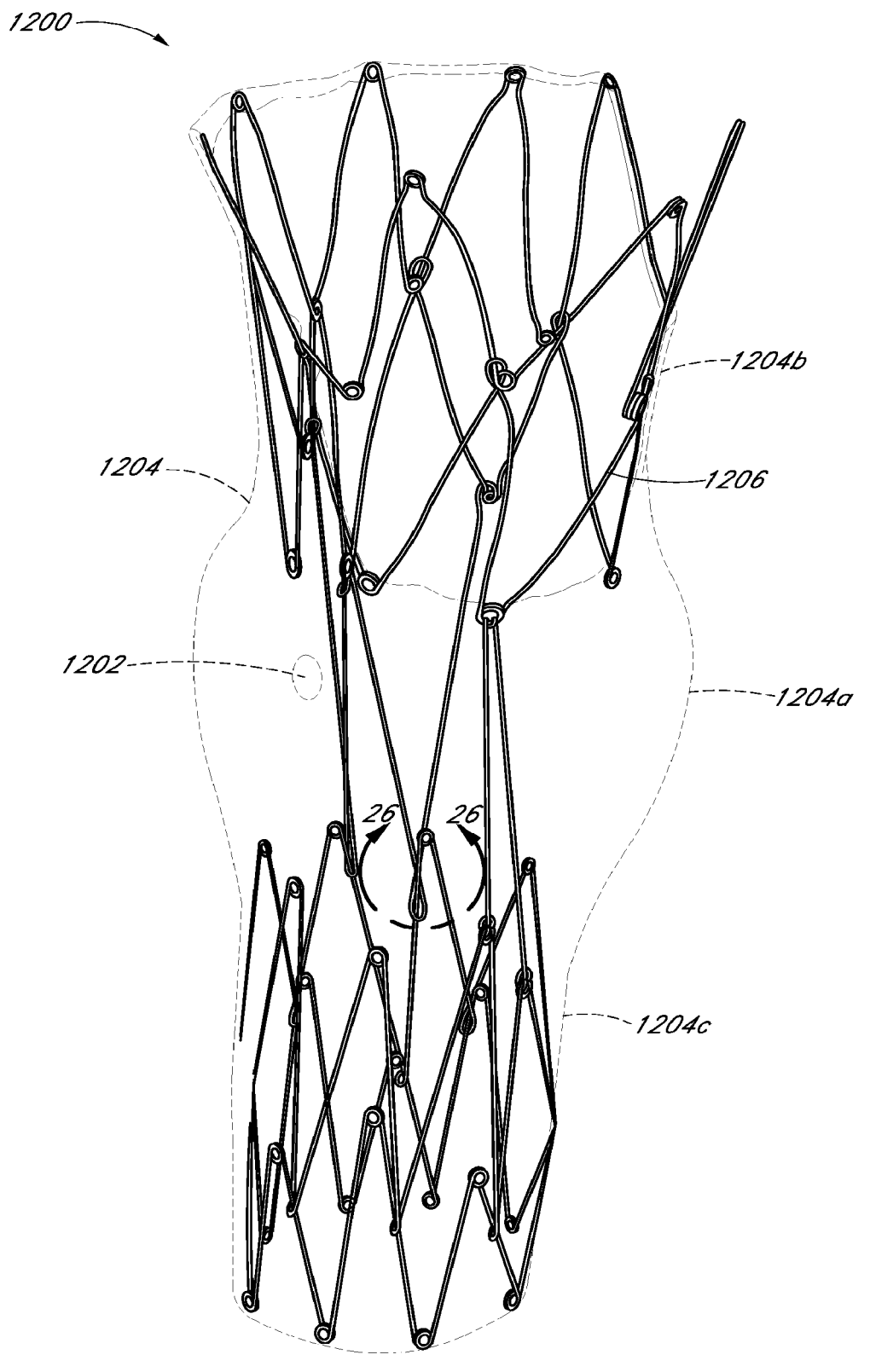

FIGS. 24A and 24B are oblique views of a prosthesis 1200 comprising one or more fenestrations 1202 formed in the graft 1204, and a stent or support member 1206. The graft 1204 is shown in dashed lines in FIG. 24B for clarity. The prosthesis 1200 can have any of the features, components, or other details of any other prosthesis embodiments disclosed herein such as, prosthesis 1010 described above. Further, any of the features of the prosthesis 1200 can be used in combination with any of the other prosthesis embodiments disclosed herein.

The graft 1204 can be supported by the stent 1206 along at least a portion of the graft 1204. Further, the graft 1204 can be overlapped and can have stitching or sutures 1208 along one or more edges of the graft 1204, which can improve the tear resistance of the graft 1204 and can improve the connection between the graft 1204 and the stent 1206.

Similar to other graft embodiments described herein, the graft 1204 can be configured to have excess or slack graft material in at least a portion thereof relative to the stent which supports the graft. For example, the excess graft material can form a bulge or other enlargement in the graft 1204 in the approximate location of one or more fenestrations 1202 formed through the graft material. The excess or slack material along the circumference of the graft 1204 (for example, in the enlarged portion 1204a of the graft 1204) can allow for circumferential and/or axial movement of the graft material and, hence, the one or more fenestrations 1202, relative to the stent 1206 and the ostium of the patient's branch vessels. Therefore, the diameter of the graft 1204 at and/or adjacent to the location of one or more fenestrations 1202 can be larger than the local diameter of the target vessel. Similarly, the diameter of the graft 1204 at and/or adjacent to the location of one or more fenestrations 1202 can be larger than the diameter of the non-enlarged portion of the graft material. In some embodiments, the outside surface of the graft 1204 in the enlarged portion 1204a or otherwise can be free from any corrugations or other preformed folds, overlaps, or other similar pre-formed features.

Further, similar to any of the other graft embodiments disclosed herein, the graft 1204 can have excess graft material in an axial direction, in addition to or in the alternative of the diametrically enlarged portion. The excess or slack material along the length of the graft 1204 can increase the circumferential and/or axial adjustability or movement of the graft material adjacent to the one or more fenestrations 1202 formed in the graft 1204. Accordingly, the length of the graft material between the proximal and distal attachment points to the stent 1206 can be longer than that of the stent 1206 between the proximal and distal attachment points. Or, the graft material in a mid-portion of the graft 1204, including on either side of the enlarged portion 1204a, can have an increased length relative to the stent radially adjacent to such graft portion.

Further, the enlarged portion and/or excess length of the graft 1204 or any other graft embodiment disclosed herein can be free from any attachment points to the stent or support member which supports the graft 1204. In these configurations, the positional adjustability of the fenestrations can be increased because the graft material is free to move in an axial and/or circumferential direction relative to the stent and relative to the ostium of the target branch vessels. The enlarged portion and/or excess length of the graft 1204 or any other graft embodiment disclosed herein can be configured to have only a limited number of attachment points to the stent or support member which supports the graft 1204. The attachment points can be sufficiently away from the fenestration or opening so as to not substantially affect the adjustability of the fenestration. For example, the prosthesis 1010 can be configured such that the enlarged or slack portion of the graft has only a limited number of attachments to a stent or connector (such as connector 1254) away from the fenestrations 1202 so that the adjustability of the enlarged or slack portion is not significantly affected. For example, in embodiments having only one fenestration in the enlarged portion, the attachment or attachments to the stent or other support member can be positioned on an opposite side of the graft as compared to the position of the fenestration. In these configurations, the positional adjustability of the fenestrations can be increased because the graft material is substantially free to move in an axial and/or circumferential direction relative to the stent and relative to the ostium of the target branch vessels.

Figure 25:
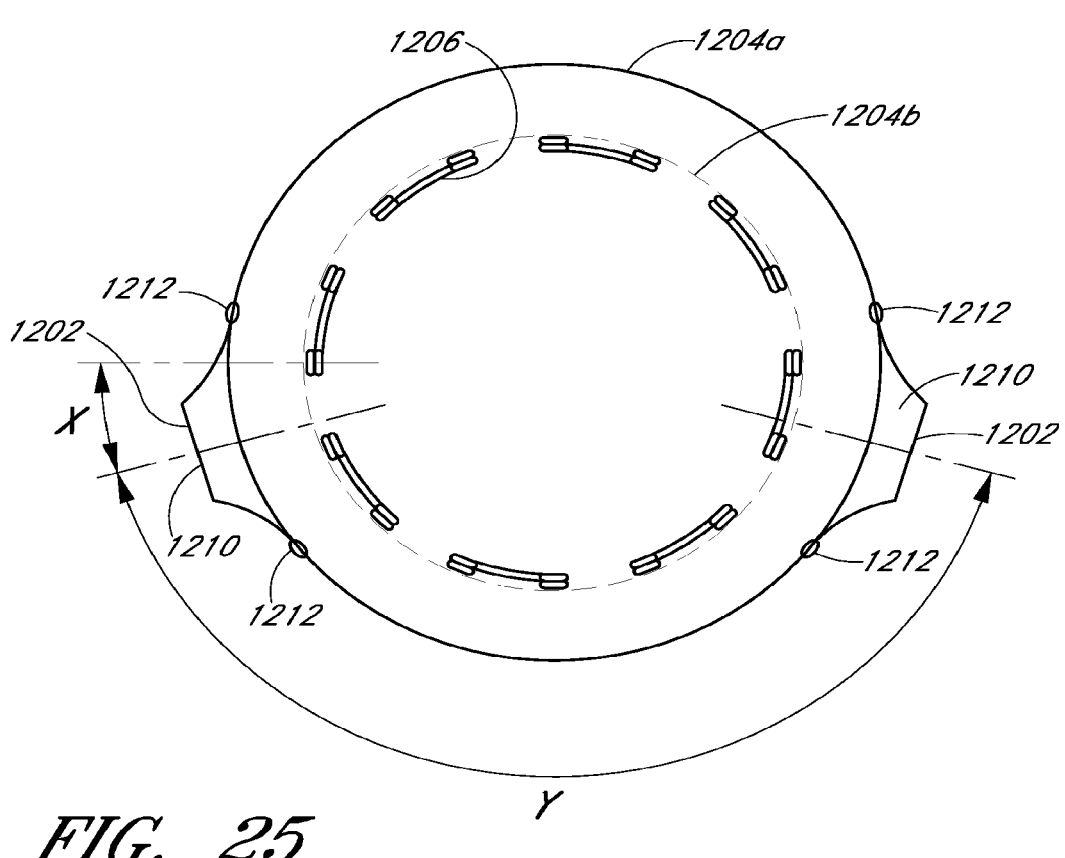
FIG. 25 is a top view of the prosthesis of FIG. 24.

With reference to FIGS. 24A-25, the graft 1204 can have one or more enlarged portions 1204a having an enlarged diameter relative to the target vessel or relative to one or more non-enlarged portions of the graft 1204, such as portions 1204b, 1204c that can improve the radial and/or axial adjustability of the fenestrations 1202 formed in the enlarged portions 1204a to better accommodate asymmetrically positioned branch vessel ostium. In some embodiments, with reference to FIGS. 24A and 24B, the graft 1204 can have an enlarged middle portion 1204a having one or more fenestrations 1202 formed therein, a non-enlarged proximal portion 1204b, and a non-enlarged distal portion 1204c.

As discussed above, in the prosthesis 1200, the enlarged portion 1204a of the graft 1204 can have a diameter that is approximately 30% larger than a diameter of the target vessel or the diameter of the non-enlarged portions 1204b, 1204c of the graft 1204. The diameter of the enlarged portion 1204a of the graft 1204 can be from approximately 20% or less to approximately 50% or more, or from approximately 25% to approximately 40% larger than the target vessel or the diameter of the non-enlarged portions 1204b, 1204c of the graft 1204, or to or from any values within these ranges.

Additionally, the enlarged portion 1204a or portion of the graft 1204 adjacent to the enlarged portion 1204a of the graft 1204 can be sized and configured to be substantially longer (i.e., in the axial direction) than the stent 1206, which can improve the radial and/or axial adjustability of the fenestrations 1202 formed in the enlarged portions 1204a to better accommodate the asymmetric and/or non-uniform positioning of branch vessel ostium. The graft 1204 can be longer than the stent 1206 in both the enlarged portion 1204a of the graft 1204 and/or in the portion of the non-enlarged distal portion 1204c of the graft adjacent to the enlarged portion 1204a of the graft 1204. For example, the enlarged portion 1204a or portion of the graft 1204 adjacent to the enlarged portion 1204a of the graft 1204 can be sized and configured to be approximately 20% longer in the axial direction than the stent 1206. The enlarged portion 1204a or portion of the graft 1204 adjacent to the enlarged portion 1204a of the graft 1204 can be sized and configured to be from approximately 10% to approximately 40% or more longer in the axial direction than the stent 1206.

FIG. 25 is a top view of the prosthesis 1200 of FIG. 24. With reference to FIGS. 24-25, the prosthesis 1200 can have fenestrations 1202 formed in an enlarged portion 1204a of the graft 1204. The fenestrations 1202 can be formed at non-diametrically opposed positions. This can improve the alignment of the fenestrations 1202 with the ostium of the target branch vessels, which in general can be located at non-diametrically opposed positions. The fenestrations 1202 formed in either the enlarged portion or portions 1204a or non-enlarged portions 1204b, 1204c of the graft 1204, can be angled away from the diametrically opposed position (represented by angle X in FIG. 25) such that the fenestrations 1202 are separated by an angle (represented by angle Y in FIG. 25) that is less than 180 degrees.

For example, the graft 1204 can have two fenestrations 1202 formed at an angle away from the diametrically opposed position (represented by angle X in FIG. 25) of approximately 15 degrees such that the fenestrations 1202 are separated by an angle (represented by angle Y in FIG. 25) that is approximately 150 degrees. The graft 1204 can have two fenestrations 1202 formed at an angle away from the diametrically opposed position of between approximately 10 degrees or less and approximately 20 degrees or more, such that the fenestrations 1202 are separated by an angle (represented by angle Y in FIG. 25) that is between approximately 160 degrees and approximately 140 degrees.

The graft 1204 can have two fenestrations 1202 formed in an enlarged portion 1204a of the graft and wherein the fenestrations 1202 are separated by an angle that is less than 180 degrees, for example approximately 150 degrees. In this configuration, positioning the fenestrations 1202 to be separated by an angle that is less than 180 degrees (such as, for example, approximately 150 degrees) can improve the alignment of the fenestrations 1202 with the ostium of the target branch vessels such that the enlarged portion 1204a of the graft 1204 can be from approximately 20% to approximately 60% greater than the non-enlarged portion 1204b, 1204c of the graft 1204. In this configuration, the enlarged portion 1204a of the graft 1204 can be from approximately 20% to approximately 40% greater than the non-enlarged portion 1204b, 1204c of the graft 1204.

The graft 1204, which can be a bifurcated or other suitably configured graft, can have two fenestrations 1202 formed in an enlarged portion 1204a of the graft, wherein the fenestrations 1202 can be separated by an angle that is less than 180 degrees, and wherein the length of at least a portion of the graft 1204 can be substantially greater than the length of the stent 1206, for example approximately 10% greater than the length of the stent 1206. In this configuration, positioning the fenestrations 1202 to be separated by an angle that is less than 180 degrees (such as, for example, approximately 150 degrees) and increasing the length of the graft 1204 to be approximately 10% greater than the length of the stent 1206 can improve the alignment/alignability of the fenestrations 1202 with the ostium of the target branch vessels such that the enlarged portion 1204a of the graft 1204 can be from approximately 10% or less to approximately 20% greater than the non-enlarged portion 1204b, 1204c of the graft 1204.

With reference to FIGS. 24-25, though not required, the prosthesis 1200 can have reinforced fenestrations 1202 comprising a tubular member 1210 inserted through the fenestration 1202 and stitched to the graft 1204 with one or more sutures 1212. In this configuration, which will be described in greater detail below, the tubular member 1210 can improve the tear resistance of the fenestration 1202 and also improve the scalability between the fenestrations 1202 and the branch grafts and stents deployed within the fenestrations 1202 as well as the pull-out resistance of the branch grafts and stents within the fenestrations 1202. This configuration can reduce leakage between the fenestrations 1202 and the branch grafts and stents deployed within the fenestrations 1202. In some embodiments, this configuration can also increase the force required to pull the branch grafts and stents deployed within the fenestrations 1202 out of the fenestrations 1202, thereby reducing the inadvertent axial movement of the branch grafts and stents deployed within the fenestrations 1202.

With reference to FIGS. 24A and 24B, although not required, the graft 1204 can have a scallop or cut-away 1230 at a proximal end portion 1204b of the graft 1204. The cut-away 1230 can be sized and configured to permit unrestricted blood flow through a branch artery, such as the suprarenal and/or the celiac arteries. The size of the cut-away 1230 can be based on the anatomy of a patient, or can be sized to accommodate a wide range of vessel anatomies. The cut-away 1230 can have a length approximately equal to the length of two stent struts, such as stent strut 1246 described below. The graft 1204 can be overlapped and have stitching 1208 along an edge of the cut-away 1230. The prosthesis 1200 can have a flared proximal end portion to increase the sealability of such end portion of the prosthesis 1200.

As described above, the prosthesis 1200 can have one or more radiopaque markers, such as but not limited to the annular radiopaque marker 1222 surrounding at least a portion of the fenestration 1202, for improved visibility under fluoroscopy during deployment. Any of the radiopaque markers can be formed from gold or platinum, or any suitable material. Any of the radiopaque markers can be formed from a suitable non-reinforcing metallic material.

Figures 27, 28:
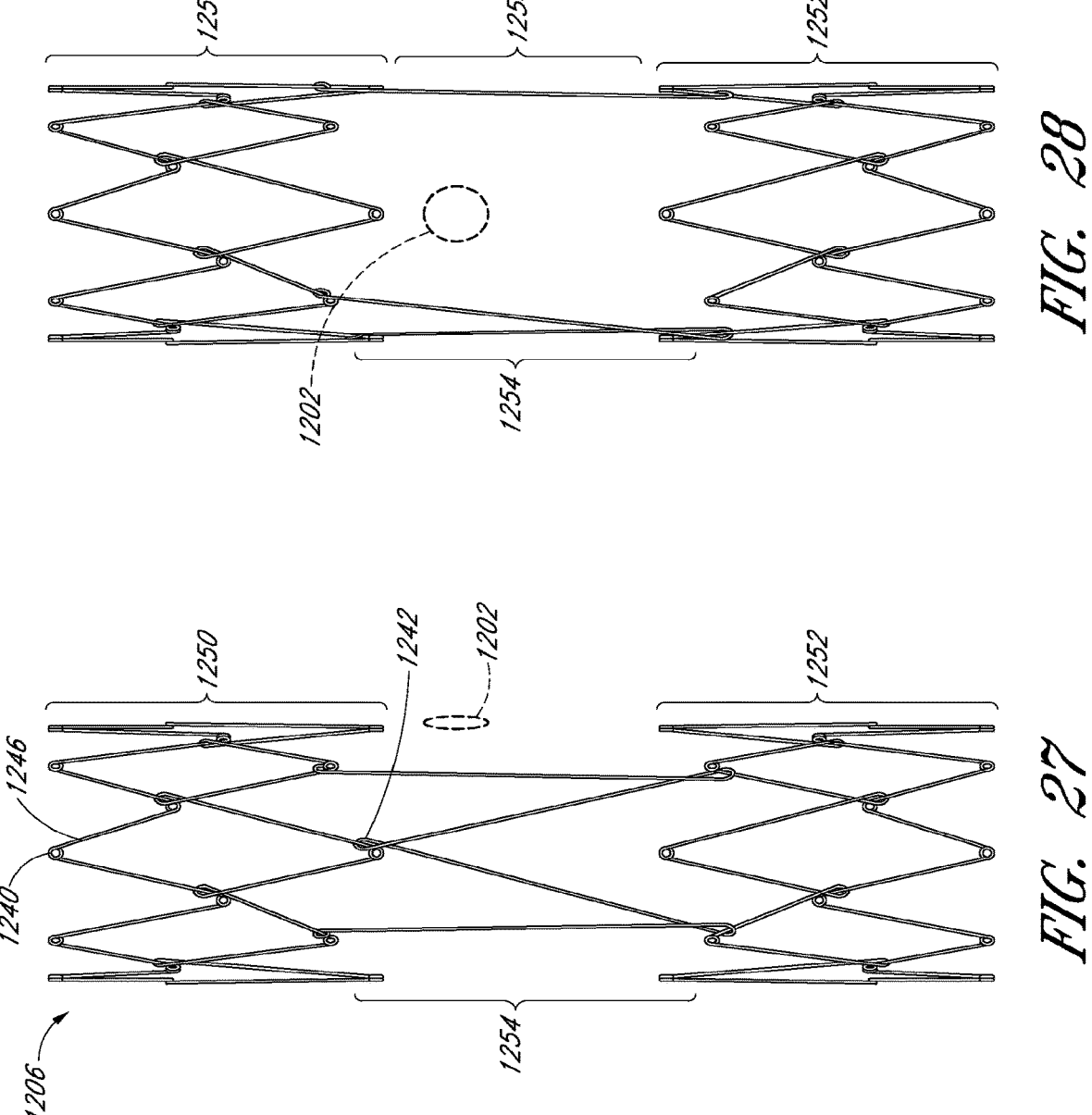
FIG. 27 is a side view of the stent shown in FIG. 24, perpendicular to an axis projecting through the fenestration.
FIG. 28 is a side view of the stent shown in FIG. 24, along an axis projecting through the fenestration.

FIG. 27 is a side view of the stent 1206 shown in FIG. 24, viewed along a line that is perpendicular to an axis projecting through a fenestration formed in the graft 1204 (not shown). For clarity, the location of a fenestration 1202 is shown dashed lines. FIG. 28 is a side view of the stent 1206, viewed along an axis projecting through a fenestration. Again, for clarity, the location of a fenestration 1202 is shown dashed lines.

Figure 26:
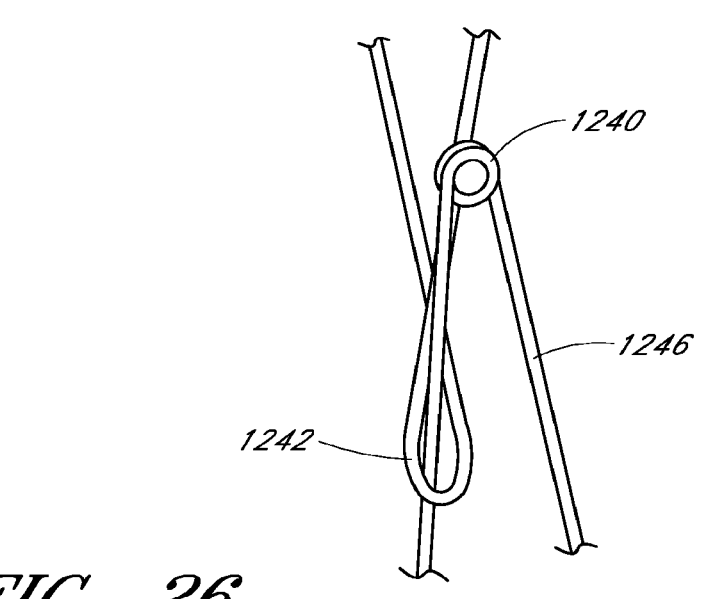
FIG. 26 is an enlarged view of a portion of the prosthesis of FIG. 24, defined by curve 26-26 of FIG. 24B.

With reference to FIGS. 26 and 27-28, the stent 1206 can be formed from one or more wires forming a plurality of loops 1240, which can be closed loops or eyelets, bends 1242, and struts 1246. Some of the bends 1242 can be configured to slide along a portion of the length of a respective strut 1246, to improve the flexibility and bendability of the stent 1206. The positioning of the plurality of loops 1240 and bends 1242 can be longitudinally offset or staggered to decrease the collapsed diameter of the prosthesis 1200.

The stent 1206 can comprise a first stent segment 1250 formed from one or more lengths of wire, a second stent segment 1252 formed from one or more lengths of wire, and one or more connecting members 1254 formed from one or more lengths of wire. The first and second stent segments 1250, 1252 can be positioned proximally and distally relative to the location of the fenestration (shown in dashed lines) that can be formed in the graft (not illustrated) that can be supported by the stent 1206. The length of the first stent segment 1250 can be sufficient to result in an increased seal zone in the suprarenal portion of the aorta, such as a length that extends to a position adjacent to or overlapping the superior mesenteric artery and/or the celiac artery.

In some embodiments, two connecting members 1254 can be positioned between the first and second stent segments 1250, 1252, and can be sized and offset from one another to provide a significant gap around the position of the fenestrations 1202 to increase the accessibility and adjustability of the fenestrations 1202 during deployment of the prosthesis 1200. As illustrated, the connecting members 1254 can have four struts. The connecting members 1254 can have three or less struts, or can have five or more struts. The connecting members 1254 can have a first connecting member 1254 having fewer struts than a second connecting member 1254.

Figure 29:
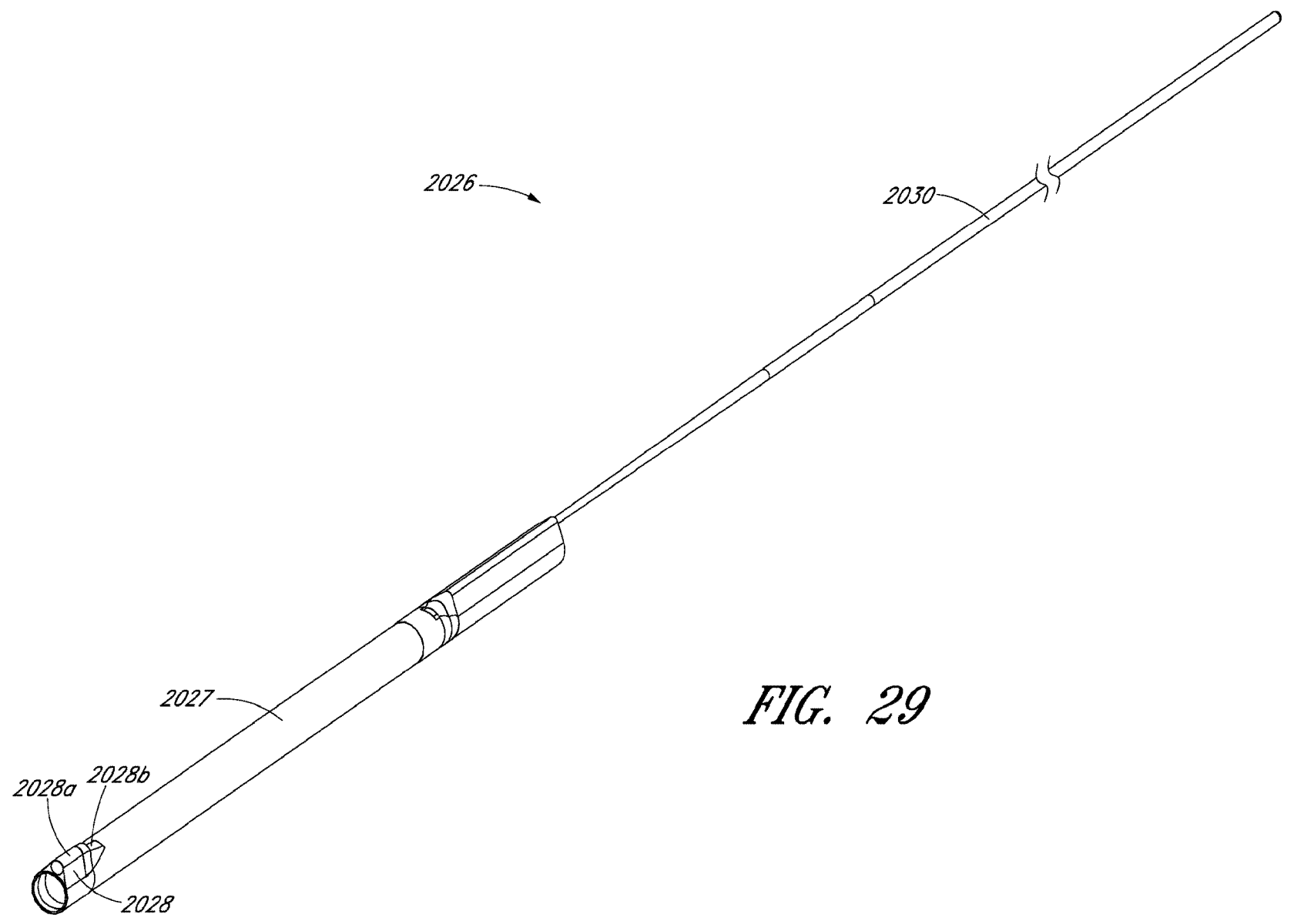
Figures 30, 31A, 31B:
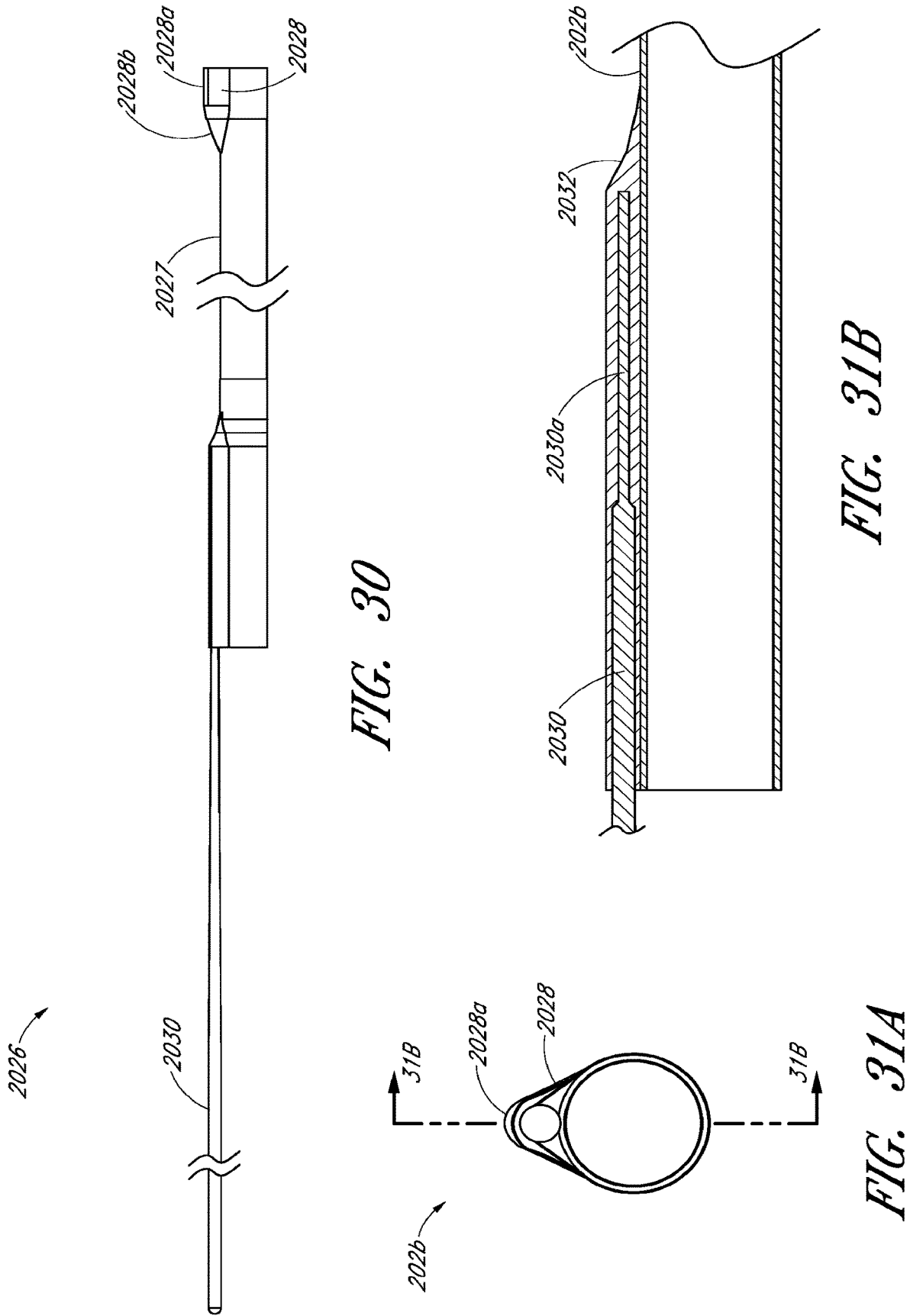
FIG. 30 is a side view of the fenestration alignment component illustrated in FIG. 29.
FIG. 31A is an end view of the fenestration alignment component illustrated in FIG. 29.
FIG. 31B is a sectional view through a portion of the fenestration alignment component, taken at 31B-31B of FIG. 31A.
Figure 32:
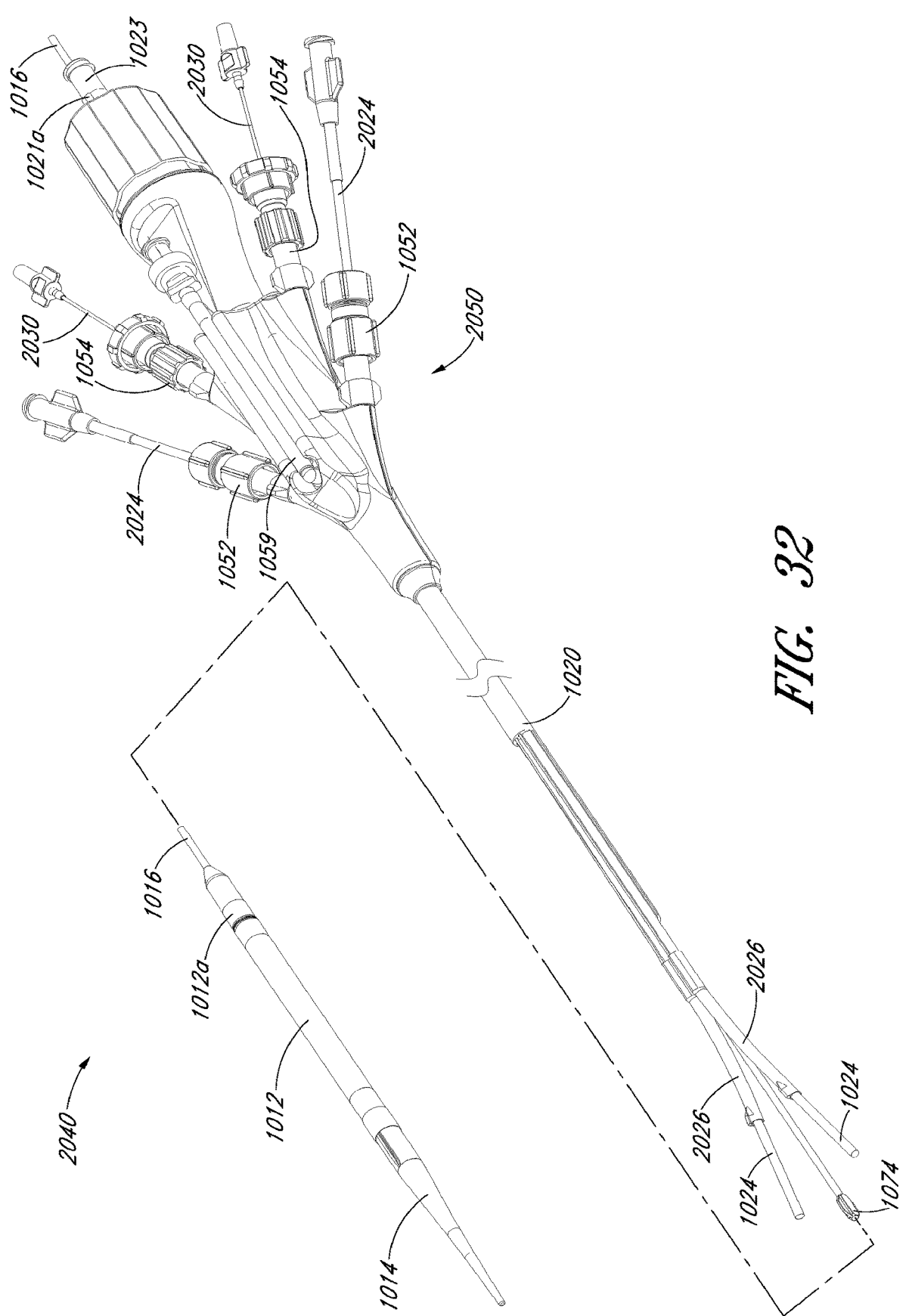
FIG. 32 is an oblique view of a delivery catheter having the fenestration alignment component of FIG. 29.
Figure 33:
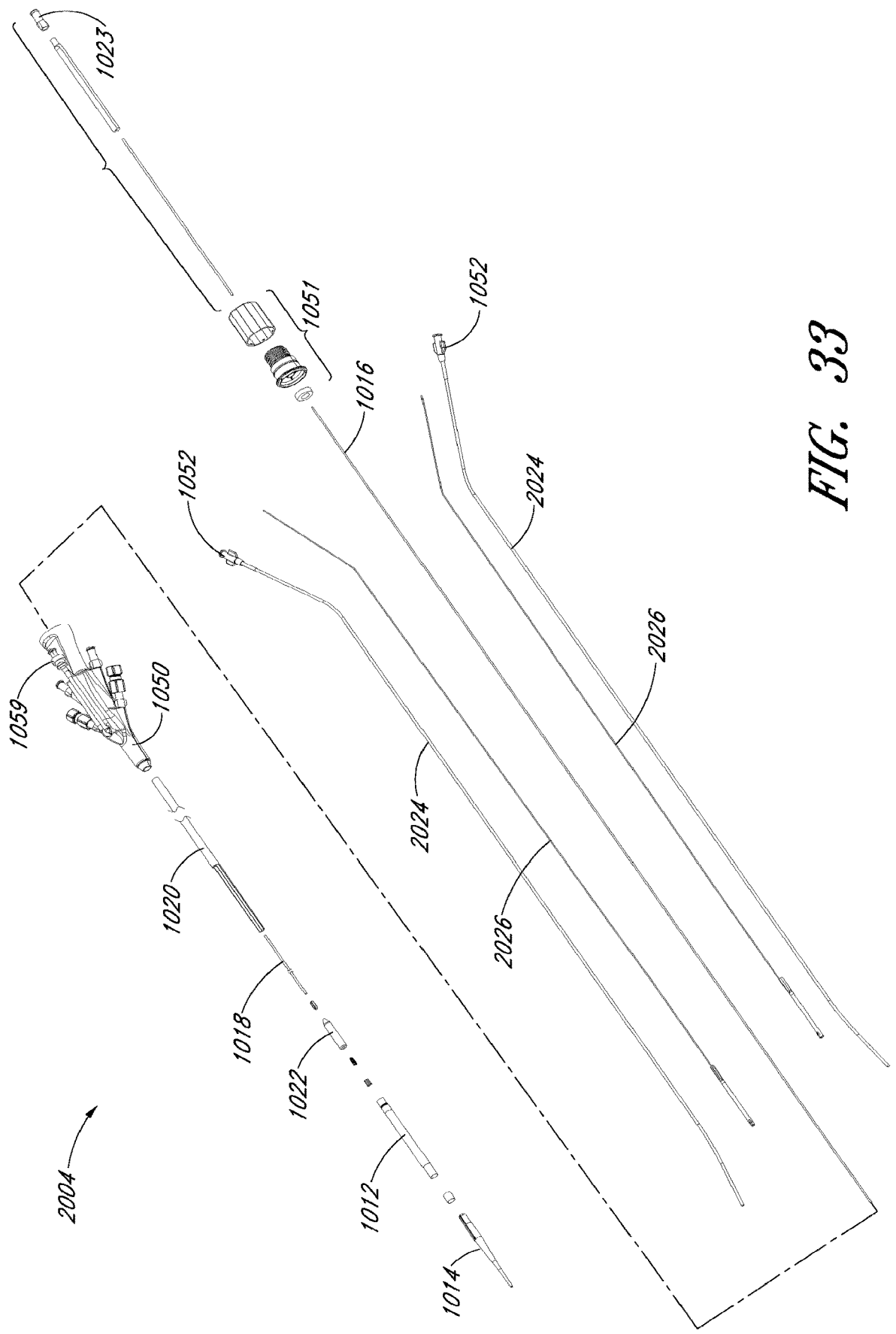
FIG. 33 is an exploded view of the delivery catheter shown in FIG. 32.

FIGS. 29-31 are oblique, side, and end views, respectively, of a fenestration alignment component 2026 (also referred to as a push member or alignment device) that can be used in any of the delivery catheter embodiments disclosed herein. FIG. 32 is an oblique view of a delivery catheter 2004 having the fenestration alignment component 2026 of FIG. 29. FIG. 33 is an exploded view of the delivery catheter 2004 shown in FIG. 32. In some delivery catheter embodiments, one or more fenestration alignment components 2026 can be used in place of or in conjunction with one or more fenestration alignment components 1026 described above in any of the delivery catheter embodiments disclosed herein.

Therefore, the fenestration alignment component 2026 can serve the same or similar function or be used for the same or similar procedural step or steps as with the embodiments of the fenestration alignment component 1026 described above. Therefore, the fenestration alignment component 2026 can be used in any of the procedures, steps, or methods as described above for the fenestration alignment component 1026. For example, after the main body of a prosthesis (such as prosthesis 1010) has been released from the outer sheath 1006 and any other radial restraints, a user can independently or collectively axially advance the fenestration alignment component 2026 relative to the guide sheath 2024 (which can be the same as the guide sheath 1024 described above) supporting the fenestration alignment component 2026 such that a portion of the fenestration alignment component 2026 engages the fenestration or branch graft of the prosthesis 1010 and pushes the fenestration or branch graft toward an ostium of the target branch vessel of the patient's vasculature.

A body portion 2027 of the fenestration alignment component 2026 can be slidably positioned around or over an outside surface of the guide sheath 2024. As illustrated in FIGS. 29, 31, and 32, the body portion 2027 can be cylindrical or tubular. The body portion 2027 can have an inside diameter or size that is greater than an outside diameter or size of the guide sheath 1024 so that the fenestration alignment component 2026 can axially translate relative to the guide sheath 1024. The body portion 2027 can have in inner diameter or cross-sectional size of approximately 0.114 in, or from approximately 0.10 in or less to approximately 0.125 inches or more. The body portion 2027 can have in outer diameter or cross-sectional size of approximately 0.126 in, or from approximately 0.110 in or less to approximately 0.15 inches or more.

The body portion 2027 can have a length of approximately 7.1 cm (2.80 in), or from approximately 5 cm (1.97 in) or less to approximately 10 cm (3.94 in), or between any values within the foregoing range. The body portion 2027 can be formed from a PEBAX covered alloy coil. For example, the body portion 2027 can have a stainless steel coil with a PEBAX tube surrounding the coil. The PEBAX can have varying hardness. The body portion 2027 can have a PTFE liner surrounding all or a portion of the body portion 2027. Additionally, the body portion 2027 can have a radiopaque marker or band supported thereon, or have portions or components thereof that are made from a radiopaque material. For example, a radiopaque band having a length of approximately 0.020 in to approximately 0.060 in can be supported by the body portion 2037.

As will be described in greater detail, the fenestration alignment component 2026 can have a snare, tab, protrusion, or other similar feature supported by the body portion to engage a portion of the prosthesis adjacent to the fenestration. For example, with reference to the illustrated embodiments, the fenestration alignment component 2026 can have a tab or protruding portion 2028 (also referred to as a protrusion or projection) projecting from the body portion 2027. The protruding portion 2028 can project away from the outside surface of the body portion 2027 by approximately 0.036 in, or from approximately 0.025 in to approximately 0.050 in, or from approximately 0.030 in to approximately 0.045 in, or between any values within any of the foregoing ranges. The protruding portion 2028 can define a cross-sectional size (in at least one direction) or diameter that is from approximately 20% or less to approximately 40% or more greater than a cross-sectional size or diameter of the body portion 2027 and/or the fenestration, or between any values within this range.

In some embodiments, the protruding portion or other component or element supported at an end of the body portion 2027 can be inflatable or otherwise moveable between a first position and a second position wherein, in the second position, such component or element projects away from the body portion 2027 more than in the first position. For example, without limitation, the component or element can be a small inflatable balloon positioned at an end of the body portion having a hollow wire in fluid communication with an inner volume thereof. The positioning wire 2030 could be made hollow to allow for inflation of the inflatable component or element.

The protruding portion 2028 can be integrally formed with the body portion 2027, or can be formed separately and adhered to, supported by, or otherwise coupled with the body portion 2027. The protruding portion 2028 can have a length of approximately 7 mm (0.276 in) or from approximately 5 mm (0.197 in) or less to approximately 10 mm (0.394 in) or more, or between any values within the foregoing range. The protruding portion 2028 can be made from PEBAX. The protruding portion 2028 can be made from a PEBAX material having a higher hardness value than the PEBAX material used to form the body portion 2027.

As mentioned, the fenestration alignment component 2026 can be configured to engage a fenestration of a prosthesis deployable by the delivery catheter 2004. For example, the enlarged or protruding portion 2028 can have a size or profile that is greater than a size or profile of the guide sheath 2024 or of the body portion 2027 of the fenestration alignment component 2026 so that, while the guide sheath 2024 can be advanced through the fenestration, the protruding portion 2028 can be sized and configured to be larger than the size or diameter of the fenestration so that the protruding portion 2028 does not pass through the fenestration.

The enlarged portion 2028 of the fenestration alignment component 2026 can have a circular cross-sectional shape or, as illustrated in FIGS. 29-31A, a non-circular cross-sectional shape. For example, the enlarged portion 2028 can have an approximately triangular or pointed shape with a rounded upper surface or portion 2028a. The enlarged portion 2028 can have a circular cross-sectional shape or a pointed shape with more than one pointed or protruding portion, or any other suitable shape.

With reference to FIGS. 29-30, the enlarged portion 2028 can have a tapered surface 2028b at the trailing end of the enlarged portion 2028. The tapered surface 2028b can facilitate the removability of the fenestration alignment component 2026 if the enlarged portion 2028 of the fenestration alignment component 2026 is inadvertently advanced through a fenestration.

The fenestration alignment components 2026 can each be attached to positioning wires 2030 such that axially advancing or retracting the positioning wires 2030 will advance or retract the fenestration alignment components 2026. The positioning wires 2030 can each define a tapering cross-sectional size that decreases toward a distal end of the positioning wire 2030 such that a cross-sectional size of the positioning wire 2030 near the body portion 2027 is smaller than a cross-sectional size of the positioning wire 2030 near the catheter handle. The positioning wire 2030 can made from a PTFE coated stainless steel, such as 304, or from any other suitable material or combination of materials. The positioning wire 2030 can have a diameter or cross-sectional size as large as approximately 0.0345 in, tapering down to a diameter or cross-sectional size of approximately 0.0200 in. The positioning wire 2030 can have a uniform diameter or cross-sectional size along the length thereof.

With reference to FIG. 31B, an end portion 2030a of the positioning wire 2030 can overlap and be affixed to the body portion 2037 of the fenestration alignment component 2026. For example, between approximately 1.0 cm (0.394 in) or less and 1.5 cm (0.591 in) or more of the positioning wire 2030 can overlap the body portion 2037. The end portion 2030a can be bonded to the body portion 2037 using any suitable technique or process. For example, the end portion 2030a can be thermally bonded to the body portion 2037 using one or more PET sleeves. A portion of the end portion 2030a can be coined or flattened. The end portion can have a greater surface area than a remainder of the end portion 2030a. For example, approximately half of the end portion 2030a can be coined or flattened.

FIG. 32 is an oblique view of a delivery catheter 2004 having the fenestration alignment component 2026 of FIG. 29. FIG. 33 is an exploded view of the delivery catheter 2004 shown in FIG. 32. FIG. 32 illustrates a handle portion 2050 of the delivery catheter 2004, which can provide an entry point for the guide sheaths 2024 and the positioning wires 2030 so as to provide an orifice or access port for these components into the main body of the delivery catheter 2004. In this configuration, a surgeon or user can manipulate the guide sheaths 2024 and fenestration alignment components 2026 by manipulating the end portions of the guide sheaths 2024 and positioning wires 2030 that extend proximally from the end of the handle portion 2050 of the delivery catheter.

The catheter 2004 can have two or more guide sheaths 2024 and two or more fenestration alignment components 2026, or the same number of guide sheaths 2024 and fenestration alignment components 2026 as the number of fenestrations in the prosthesis. The catheter 2004 having guide sheaths 2024 with fenestration alignment components 2026 as described herein can be configured such that the guide sheaths 2024, fenestration alignment components 2026, and/or positioning wires 2030 are advanceable within standard lumen formed in the delivery catheter 2004. The lumen of the delivery catheter 2004 may be enlarged or sized and configured to accommodate such guide sheaths 2024 with fenestration alignment components 2026.

Figure 34:
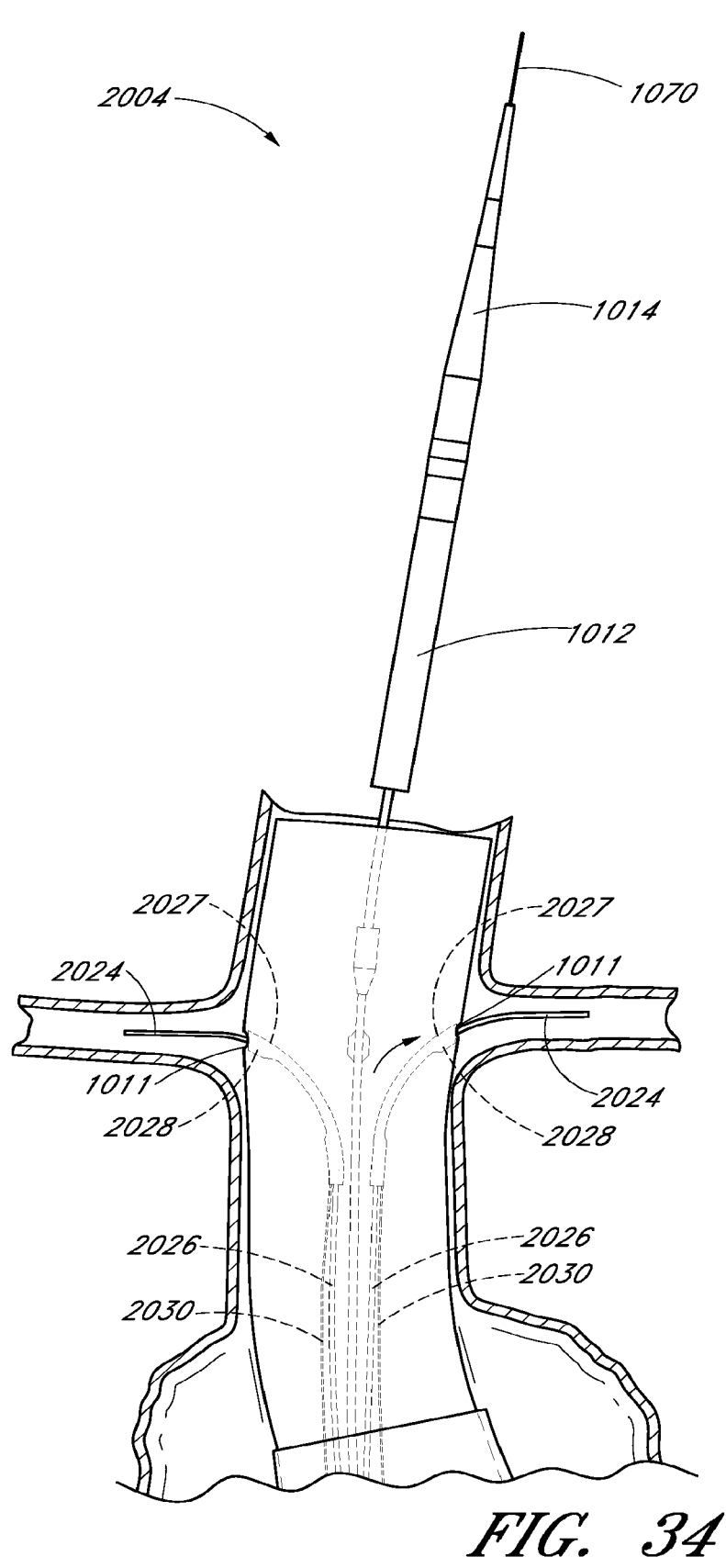
FIG. 34 is a sectional view of a portion of a patient's vasculature, showing the fenestration alignment component illustrated in FIG. 29 advancing an inner wall of the prosthesis adjacent to a fenestration toward an ostium of the target branch vessel.

FIG. 34 is a sectional view of a portion of a patient's vasculature, showing the fenestration alignment component 2026 illustrated in FIG. 29 advancing an inner wall of the prosthesis adjacent to a fenestration toward an ostium of the target branch vessel. As illustrated, the fenestration alignment component 2026 of the catheter 2004 can be axially advanced relative to the guide sheath 2024 (which can be the same as any other guide sheath embodiments disclosed herein, including without limitation guide sheath 1024) by advancing the positioning wire 2030 distally to push the fenestration 1011 of the prosthesis 1010 over the branch sheath 2024 and into approximate alignment with the ostium of the branch vessel. The catheter system 2004 can be configured to not have a fenestration alignment component 2026, and can accordingly be configured to deploy a fenestrated graft without the use of such a component. As will be described below, snares, protrusions, tabs, or other features can be formed on the sheaths 1024 to push the fenestrations toward the branch vessel ostium.

Figure 35:
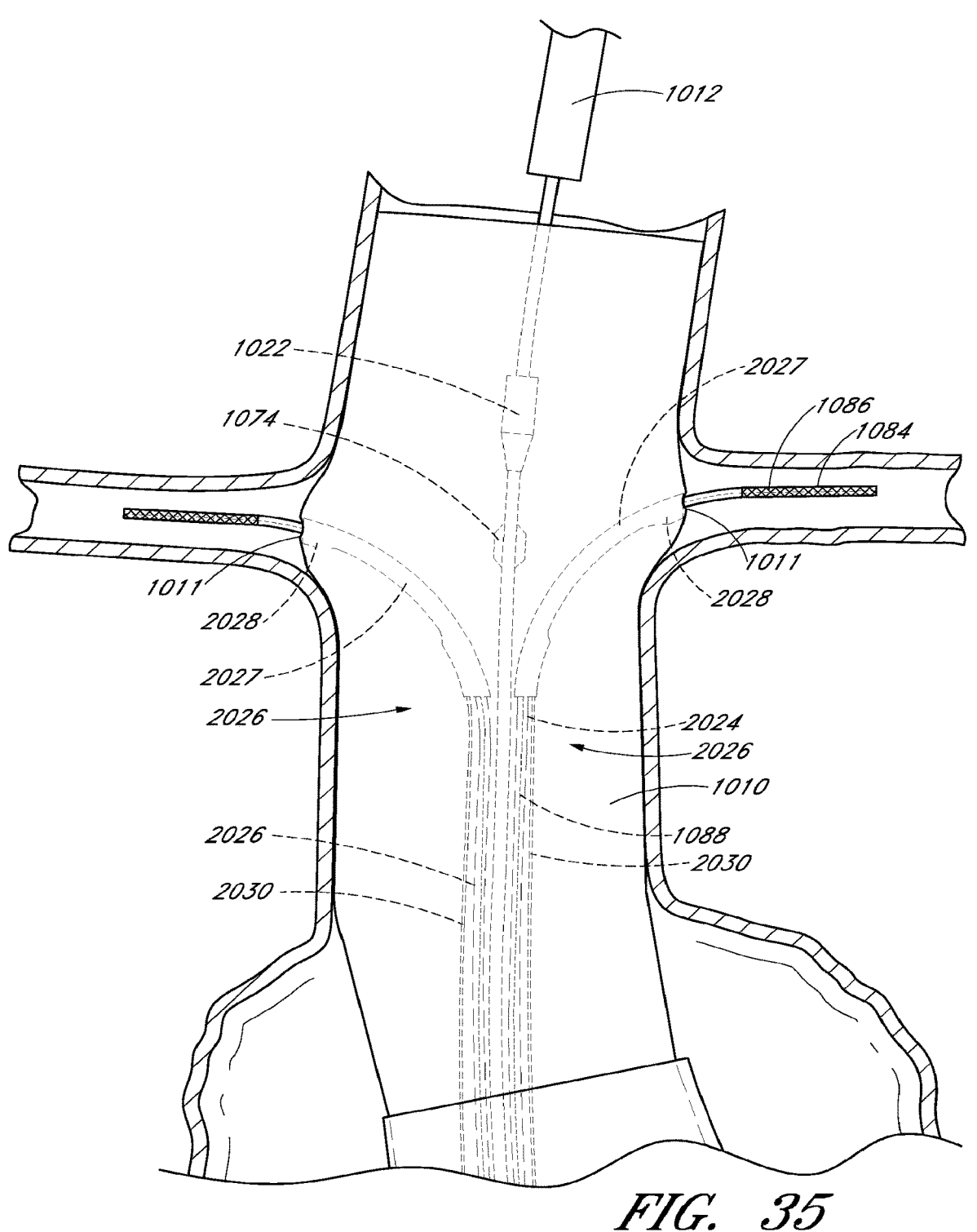
FIG. 35 is a sectional view of a portion of a patient's vasculature, showing a branch stent being advanced into the target branch vessel while the fenestration alignment component illustrated in FIG. 29 can be used to maintain the inner wall of the prosthesis adjacent to a fenestration in the prosthesis in the desired position relative to the ostium of the target branch vessel.

FIG. 35 is a sectional view of a portion of a patient's vasculature, showing a branch stent being advanced into the target branch vessel while the fenestration alignment component 2026 can be used to maintain the inner wall of the prosthesis adjacent to a fenestration in the prosthesis in the desired position relative to the ostium of the target branch vessel. As illustrated in FIG. 35, the fenestration alignment components 2026 have been advanced to a second position, the second position being defined as the position where the fenestrations 1011 are approximately aligned with the ostium of the target branch vessels. As illustrated in FIG. 35, a covered or uncovered branch stent 1084 can be deployed in the branch vessel by advancing the branch stent 1084 through the branch sheath 2024 using a suitable catheter, such as a renal stent catheter, into the target vessel, after the angiographic catheter has been removed from the branch sheath 2024.

The stent 1084 can be supported on an inflation balloon 1086, which can be supported by a guidewire 1088. The guidewire 1088 can be configured to have an inflation lumen therein, to inflate the balloon 1086 and expand the branch stent 1084 in the target location after the branch sheath 2024 has been at least partially retracted so as to not interfere with the expansion of the branch stent 1084. The fenestration alignment components 2026 may need to be at least partially withdrawn before deploying the stents 1084, to enable the inflation balloon to expand the stents 1084. The inflation balloon 1086 can be configured to expand and flare a portion of the stent 1084 within or to the inside of the fenestration 1011 formed in the prosthesis. Thereafter, the components comprising the delivery catheter 2004 can be withdrawn, and/or additional prostheses can be deployed in the patient's vasculature, including without limitation a suprarenal stent graft, or other desired components.

As mentioned, any embodiments of the delivery catheter 2004 can have any of the same features, materials, components, dimensions, or other details of any other catheter disclosed herein, including without limitation the embodiment(s) of the delivery catheter 1004 described above. Like numbered features shown in the illustrations of the delivery catheter 2004 can be the same or similar to the same numbered features of the delivery catheter 1004 embodiments described herein.

While the above detailed description has shown, described, and pointed out novel features as applied to various embodiments, it will be understood that various omissions, substitutions, and changes in the form and details of the device or process illustrated can be made without departing from the spirit of the disclosure. Additionally, the various features and processes described above can be used independently of one another, or can be combined in various ways. All possible combinations and sub combinations are intended to fall within the scope of this disclosure.

As will be recognized, certain embodiments described herein can be embodied within a form that does not provide all of the features and benefits set forth herein, as some features can be used or practiced separately from others. Unless otherwise defined herein, the term approximate or approximately means values within 10% of the stated value.

Additionally, any embodiments of the fenestration alignment components or devices disclosed herein can be used to deploy any suitable fenestrated prosthesis, with or without modification within the scope of one of ordinary skill in the art. For example and any embodiments of the fenestration alignment components or devices disclosed by the references previously incorporated by reference in their entireties as if fully set forth herein. All such embodiments and combinations of embodiments are hereby incorporated by reference as if fully set forth herein. Further, any embodiments of the fenestration alignment components or devices disclosed herein can be used in combination with any of the delivery devices disclosed in either of the foregoing applications, and such combinations are hereby incorporated by reference as if fully set forth herein.

What is claimed is:

1. A fenestrated graft deployment system, comprising:
a delivery catheter comprising a catheter body; and
a first fenestration alignment device comprising a longitudinal axis and extending through at least a portion of the catheter body, the first fenestration alignment device configured to be axially moveable between a first position and a second position, the first fenestration alignment device being prepositioned within the delivery catheter when the delivery catheter is in a predeployment state;
wherein the first fenestration alignment device comprises a tubular shaped member having a longitudinal axis and a protrusion projecting from an outside surface of a distal portion of the tubular shaped member, the protrusion comprising a non-circular cross section which is perpendicular to the longitudinal axis of the tubular shaped member and being sized and configured to engage a lateral opening of an endoluminal prosthesis when the first fenestration alignment device is advanced toward the second position, and
wherein the protrusion comprises an elongate structure extending along the longitudinal axis of the first fenestration alignment device.

2. The fenestrated graft deployment system of claim 1, further comprising a first guidewire prepositioned within the delivery catheter when the delivery catheter is in the predeployment state.

3. The fenestrated graft deployment system of claim 2, wherein the first fenestration alignment device is configured to be axially moveable along the first guidewire between the first position and the second position.

4. The fenestrated graft deployment system of claim 2, wherein the distal portion of the tubular shaped member comprises a wall portion that surrounds at least a portion of the first guidewire.

5. The fenestrated graft deployment system of claim 2, wherein the first guidewire is a hollow guidewire or hollow sheath.

6. The fenestrated graft deployment system of claim 2, wherein a distal end portion of the first guidewire is within a lumen of the catheter body when the first guidewire is prepositioned within the delivery catheter.

7. The fenestrated graft deployment system of claim 1, wherein the first fenestration alignment device is configured to approximately align the lateral opening of the endoluminal prosthesis with an ostium of the first target branch vessel when the first fenestration alignment device is advanced to the second position.

8. The fenestrated graft deployment system of claim 1, further comprising a second fenestration alignment device.

9. The fenestrated graft deployment system of claim 1, wherein in the predeployment state, an end portion of the first fenestration alignment device is configured to be positioned within a lumen of the endoluminal prosthesis.

10. The fenestrated graft deployment system of claim 1, further comprising an inner core at least partially extending through the catheter body.

11. The fenestrated graft deployment system of claim 10, wherein in the predeployment state, an end portion of the first fenestration alignment device is positioned distal to the inner core.

12. The fenestrated graft deployment system of claim 11, wherein the protrusion comprises a tapered surface.

13. The fenestrated graft deployment system of claim 11, further comprising the endoluminal prosthesis.

* * * * *